(12) United States Patent
Vezina et al.

(10) Patent No.: US 11,826,419 B2
(45) Date of Patent: *Nov. 28, 2023

(54) METHOD OF PREPARING PLANT-DERIVED VLPS

(75) Inventors: Louis-Philippe Vezina, Neuville (CA); Manon Couture, St. Augustin de Desmaures (CA); Dany Paquet, St. Jean Chrysostome (CA); Michele Dargis, Quebec (CA); Marc-Andre D'Aoust, Quebec (CA)

(73) Assignee: MEDICAGO INC., Quebec (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/497,757

(22) PCT Filed: Sep. 21, 2010

(86) PCT No.: PCT/CA2010/001488
§ 371 (c)(1),
(2), (4) Date: Mar. 22, 2012

(87) PCT Pub. No.: WO2011/035422
PCT Pub. Date: Mar. 31, 2011

(65) Prior Publication Data
US 2012/0178149 A1    Jul. 12, 2012

Related U.S. Application Data

(60) Provisional application No. 61/244,786, filed on Sep. 22, 2009.

(51) Int. Cl.
| | | |
|---|---|---|
| *C12N 7/00* | (2006.01) | |
| *C12N 15/82* | (2006.01) | |
| *A61K 39/145* | (2006.01) | |
| *A61K 39/12* | (2006.01) | |
| *A61K 39/00* | (2006.01) | |

(52) U.S. Cl.
CPC ............ *A61K 39/145* (2013.01); *A61K 39/12* (2013.01); *C12N 7/00* (2013.01); *C12N 15/8203* (2013.01); *C12N 15/8257* (2013.01); *C12N 15/8258* (2013.01); *A61K 2039/517* (2013.01); *A61K 2039/5258* (2013.01); *C12N 2760/16123* (2013.01); *C12N 2760/16134* (2013.01)

(58) Field of Classification Search
None
See application file for complete search history.

(56) References Cited

U.S. PATENT DOCUMENTS

| | | | |
|---|---|---|---|
| 4,945,050 A | 7/1990 | Sanford | |
| 5,036,006 A | 7/1991 | Sanford | |
| 5,100,792 A | 3/1992 | Sanford | |
| 5,166,068 A * | 11/1992 | Fujimura | A01H 4/00 435/421 |
| 5,232,833 A | 8/1993 | Sanders | |
| 5,486,510 A | 1/1996 | Bouic | |
| 5,625,136 A | 4/1997 | Koziel | |
| 5,762,939 A | 6/1998 | Smith | |
| 5,773,695 A * | 6/1998 | Thompson | C07K 14/415 435/320.1 |
| 5,858,368 A | 1/1999 | Smith | |
| 5,958,422 A | 9/1999 | Lomonossoff | 424/199 |
| 6,020,169 A | 2/2000 | Lee | 435/70.1 |
| 6,042,832 A | 3/2000 | Koprowski et al. | |
| 6,284,875 B1 * | 9/2001 | Turpen | C07K 14/415 530/427 |
| 6,287,570 B1 | 9/2001 | Foley | 424/199.1 |
| 6,326,470 B1 | 12/2001 | Cosgrove | 530/3.7 |
| 6,403,865 B1 | 6/2002 | Koziel | |
| 6,489,537 B1 | 12/2002 | Rea | |
| 7,125,978 B1 | 10/2006 | Vezina | |
| 7,132,291 B2 | 11/2006 | Cardineau | |
| 7,897,842 B2 | 3/2011 | Bakker | |
| 8,124,103 B2 | 2/2012 | Yusibov et al. | |
| 9,452,210 B2 | 9/2016 | D'Aoust et al. | |
| 9,458,470 B2 | 10/2016 | D'Aoust et al. | |
| 9,492,528 B2 | 11/2016 | D'Aoust et al. | |
| 2001/0006950 A1 | 7/2001 | Punnonen | |
| 2004/0002061 A1 | 1/2004 | Kawaoka | |

(Continued)

FOREIGN PATENT DOCUMENTS

| | | |
|---|---|---|
| AU | 2008278222 A1 | 1/2009 |
| AU | 2009202819 | 6/2009 |

(Continued)

OTHER PUBLICATIONS

Biemelt et al (J. Virol., 77(17), pp. 9211-9220).*
Webby et al (Plant Disease, 76(11), pp. 1125-1132, 1992).*
Wickramasinghe et al (Biotechnology and Bioengineering, 92(2), pp. 199-208, 2005).*
Firek et al (Plant Molecular Biology, 23, pp. 861-870, 1993; cited on IDS).*

(Continued)

*Primary Examiner* — Charles Logsdon
(74) *Attorney, Agent, or Firm* — BALLARD SPAHR LLP

(57) ABSTRACT

Methods of preparing plant-derived virus like particles (VLPs) are provided. The method may comprise obtaining a plant, or plant matter comprising apoplast-localized VLPs, producing a protoplast/spheroplast fraction and apoplast fraction from the plant or plant matter, and recovering the apoplast fraction. The apoplast fraction comprises plant-derived VLPs. Alternatively, VLPs may be obtained from plant or plant matter comprising plant-derived VLPs by digesting the plant matter using a cell wall degrading enzyme composition to produced a digested fraction. The digested fraction is filtered to produced a filtered fraction, and the plant-derived VLPs are recovered from the filtered fraction.

Figure 1:
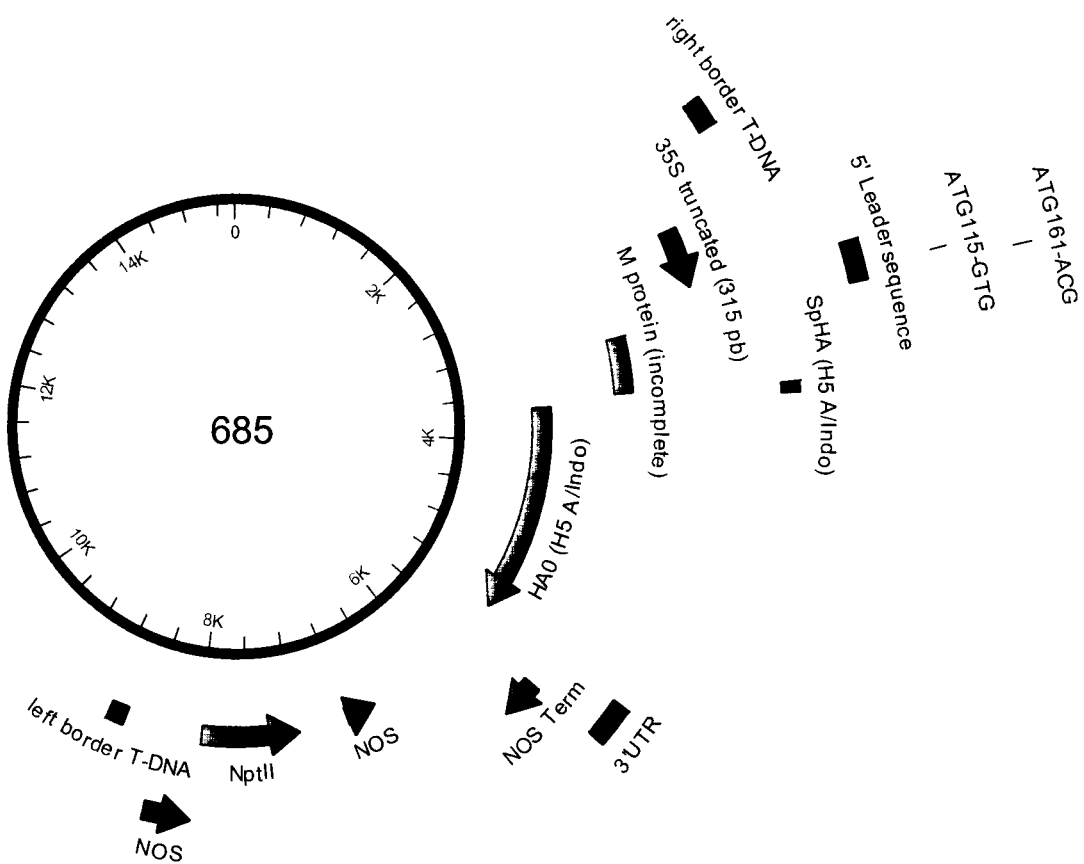

34 Claims, 11 Drawing Sheets
Specification includes a Sequence Listing.

(56) References Cited

U.S. PATENT DOCUMENTS

| | | |
|---|---|---|
| 2004/0268442 A1 | 12/2004 | Miller |
| 2005/0048074 A1 | 3/2005 | Cardineau |
| 2006/0252132 A1 | 11/2006 | Yang |
| 2006/0263804 A1 | 11/2006 | Robinson et al. |
| 2007/0207526 A1* | 9/2007 | Coit et al. |
| 2007/0286873 A1 | 12/2007 | Williams |
| 2009/0117144 A1 | 5/2009 | Rasochova |
| 2009/0191309 A1* | 7/2009 | Rastogi et al. |
| 2009/0311669 A1 | 12/2009 | Kawaoka |
| 2010/0167376 A1* | 7/2010 | Hogan .................... C12P 19/14 435/209 |
| 2010/0239610 A1 | 9/2010 | D'Aoust |
| 2010/0310604 A1 | 12/2010 | D'Aoust |
| 2011/0191915 A1 | 8/2011 | Couture |
| 2011/0293650 A1 | 12/2011 | D'Aoust |
| 2012/0178149 A1 | 7/2012 | Vezina |
| 2012/0189658 A1 | 7/2012 | Couture |
| 2013/0067807 A1 | 3/2013 | Vezina |
| 2013/0142826 A1 | 6/2013 | D'Aoust |
| 2013/0183341 A1 | 7/2013 | D'Aoust |
| 2013/0295609 A1 | 11/2013 | D'Aoust et al. |

FOREIGN PATENT DOCUMENTS

| | | |
|---|---|---|
| AU | 2009202819 A1 | 6/2009 |
| AU | 2008278222 | 1/2010 |
| AU | 2009267759 | 1/2010 |
| AU | 2009267759 A1 | 1/2010 |
| AU | 2010265766 | 6/2010 |
| AU | 2010265766 | 2/2012 |
| AU | 2010300033 | 3/2012 |
| AU | 2010300033 A1 | 3/2012 |
| AU | 2010300034 | 3/2012 |
| AU | 2010300034 A1 | 3/2012 |
| AU | 2012231717 | 9/2013 |
| CA | 2615372 A1 | 1/2009 |
| CA | 2693956 | 1/2009 |
| CA | 2693956 A1 | 1/2009 |
| CA | 2707235 | 6/2009 |
| CA | 2707235 A1 | 6/2009 |
| CA | 2615372 | 1/2010 |
| CA | 2730185 | 1/2010 |
| CA | 2730185 A1 | 1/2010 |
| CA | 2772962 | 1/2010 |
| CA | 2762042 | 6/2010 |
| CA | 2772962 A1 | 3/2011 |
| CA | 2772964 | 3/2011 |
| CA | 2772964 A1 | 3/2011 |
| CN | 1861793 A | 5/2005 |
| CN | 200880107072.9 | 6/2009 |
| CN | 200980109781.5 | 6/2009 |
| CN | 200980134868.8 | 1/2010 |
| CN | 201080042333.0 | 3/2011 |
| CU | 2010006 | 1/2009 |
| CU | D2010006 | 1/2009 |
| CU | 2010152 | 6/2009 |
| CU | D2010152 | 6/2009 |
| EA | 201001198 | 1/2010 |
| EG | 2010010061 | 1/2009 |
| EG | 1222/2010 | 6/2009 |
| EP | 2009793741 | 1/2009 |
| EP | 20080783201 | 1/2009 |
| EP | 2009700061 | 6/2009 |
| EP | 2173886 | 4/2010 |
| EP | 2010791119 | 6/2010 |
| EP | 2238253 | 10/2010 |
| EP | 2010818190 | 3/2011 |
| EP | 2010818191 | 3/2011 |
| EP | 2307549 | 4/2011 |
| EP | 2010791119 | 5/2012 |
| EP | 2480560 | 8/2012 |
| EP | 2480658 | 8/2012 |
| EP | 2570484 | 3/2013 |
| GE | 11920 | 6/2009 |
| ID | W-002010248 | 6/2009 |
| IL | 203018 | 1/2009 |
| IL | 210215 | 1/2009 |
| IL | 206967 | 6/2009 |
| IL | 210215 | 1/2010 |
| IL | 218393 | 3/2011 |
| IL | 218422 | 3/2011 |
| IL | 218393 | 4/2012 |
| IL | 218422 | 4/2012 |
| JP | 2010-516334 | 1/2009 |
| JP | 2011-516934 | 1/2009 |
| JP | 2010-542486 | 6/2009 |
| JP | 2010-516334 A | 5/2010 |
| JP | 2012516452 | 6/2010 |
| JP | 2012-530059 | 3/2011 |
| JP | 2012-530060 | 3/2011 |
| JP | 2011-516934 A | 5/2011 |
| JP | 2012-530059 A | 11/2012 |
| JP | 2012-530060 A | 11/2012 |
| KR | 1020117001798 | 1/2009 |
| KR | 1020117001798 | 1/2009 |
| KR | 1020107018343 | 6/2009 |
| KR | 1020117001798 | 1/2010 |
| KR | 1020107002538 | 3/2010 |
| KR | 1020107018343 | 11/2010 |
| MA | 2010000142 | 1/2009 |
| MA | 2010003442 | 6/2009 |
| MX | MX/a/2010/000525 | 1/2009 |
| MX | MX/a/2010/007962 | 6/2009 |
| MX | MX/a/2011/000459 | 1/2010 |
| MY | PI 2010000142 | 1/2009 |
| MY | PI 2010003442 | 6/2009 |
| NZ | 582360 | 1/2009 |
| NZ | 590144 | 1/2009 |
| NZ | 587108 | 6/2009 |
| NZ | 598481 | 3/2011 |
| NZ | 598508 | 3/2011 |
| NZ | 582360 A | 4/2012 |
| NZ | 590144 A | 11/2012 |
| NZ | 587108 A | 4/2013 |
| PH | 12012500565 | 3/2011 |
| PH | 12012500566 | 3/2011 |
| RU | 2011-105073 | 1/2010 |
| RU | 2012101946 | 6/2010 |
| RU | 2012-115661 | 3/2011 |
| RU | 2012-115996 | 3/2011 |
| RU | 2012-115996 | 10/2013 |
| SG | 201000090-9 | 1/2009 |
| SG | 201009568-5 | 1/2009 |
| SG | 158301 | 4/2012 |
| TH | 1201001223 | 3/2011 |
| TH | 1201001239 | 3/2011 |
| WO | WO 1986/003224 | 6/1986 |
| WO | WO-1986/003224 A1 | 6/1986 |
| WO | WO 2000/009725 | 2/2000 |
| WO | WO-2000/009725 A2 | 2/2000 |
| WO | WO 2000/037663 | 6/2000 |
| WO | WO-2000/037663 A2 | 6/2000 |
| WO | WO 2000/056906 | 9/2000 |
| WO | WO-2000/056906 A1 | 9/2000 |
| WO | WO 2000/063400 | 10/2000 |
| WO | WO-2000/063400 A2 | 10/2000 |
| WO | WO 2002/074795 | 9/2002 |
| WO | WO-2002/074795 A2 | 9/2002 |
| WO | WO 2003/025124 | 3/2003 |
| WO | WO-2003/025124 A2 | 3/2003 |
| WO | WO 2003/068163 | 8/2003 |
| WO | WO-2003/068163 A2 | 8/2003 |
| WO | WO 2003/068993 | 8/2003 |
| WO | WO-2003/068993 A1 | 8/2003 |
| WO | WO 2004/098530 | 11/2004 |
| WO | WO-2004/098530 A2 | 11/2004 |
| WO | WO 2004/098533 | 11/2004 |
| WO | WO-2004/098533 A2 | 11/2004 |
| WO | WO 2005/020889 | 3/2005 |
| WO | WO-2005/020889 A2 | 3/2005 |
| WO | WO 2006/016380 | 2/2006 |
| WO | WO-2006/016380 A2 | 2/2006 |
| WO | WO 2006/119516 | 11/2006 |

(56) References Cited

FOREIGN PATENT DOCUMENTS

| WO | WO-2006/119516 A2 | 11/2006 |
|---|---|---|
| WO | WO 2007/011904 | 1/2007 |
| WO | WO-2007/011904 A2 | 1/2007 |
| WO | WO 2007/019094 | 2/2007 |
| WO | WO-2007/019094 A2 | 2/2007 |
| WO | WO 2007/047831 | 4/2007 |
| WO | WO-2007/047831 A2 | 4/2007 |
| WO | WO 2007/095318 | 8/2007 |
| WO | WO-2007/095318 A2 | 8/2007 |
| WO | WO 2007/130327 | 11/2007 |
| WO | WO-2007/130327 A2 | 11/2007 |
| WO | WO 2007/135480 | 11/2007 |
| WO | WO-2007/135480 A1 | 11/2007 |
| WO | WO 2008/054540 | 5/2008 |
| WO | WO-2008/054540 A2 | 5/2008 |
| WO | WO 2008/060669 | 5/2008 |
| WO | WO-2008/060669 A2 | 5/2008 |
| WO | WO 2008/087391 | 7/2008 |
| WO | WO-2008/087391 A1 | 7/2008 |
| WO | WO 2008/151440 | 12/2008 |
| WO | WO-2008/151440 A1 | 12/2008 |
| WO | WO 2009/008573 | 1/2009 |
| WO | WO-2009/008573 A1 | 1/2009 |
| WO | WO 2009/009876 | 1/2009 |
| WO | WO-2009/009876 A1 | 1/2009 |
| WO | WO 2009/026397 | 2/2009 |
| WO | WO-2009/026397 A2 | 2/2009 |
| WO | WO 2009/076778 | 6/2009 |
| WO | WO-2009/076778 A1 | 6/2009 |
| WO | WO 2010/003225 | 1/2010 |
| WO | WO-2010/003225 A1 | 1/2010 |
| WO | WO 2010/003235 | 1/2010 |
| WO | WO 2010/006452 | 1/2010 |
| WO | WO-2010/006452 A1 | 1/2010 |
| WO | WO 2010/025285 | 3/2010 |
| WO | WO-2010/025285 A1 | 3/2010 |
| WO | PCT/CA2010/000983 | 6/2010 |
| WO | WO 2010/077712 | 7/2010 |
| WO | WO-2010/077712 A1 | 7/2010 |
| WO | WO 2010/148511 | 12/2010 |
| WO | WO-2010/148511 A1 | 12/2010 |
| WO | WO 2011/035422 | 3/2011 |
| WO | WO-2011/035422 A1 | 3/2011 |
| WO | WO 2011/035423 | 3/2011 |
| WO | WO-2011/035423 A1 | 3/2011 |
| WO | PCT/CA2012/050180 | 3/2012 |
| WO | WO 2012/061815 | 5/2012 |
| WO | WO-2012/061815 A2 | 5/2012 |
| WO | WO 2012/083445 | 6/2012 |
| WO | WO-2012/083445 A1 | 6/2012 |
| WO | WO 2012/126123 | 9/2012 |

OTHER PUBLICATIONS

Santi et al (Vaccine, 26(15), pp. 1846-1854, 2008; cited on IDS).*
D'Auost et al (Plant Biotechnology Journal, 6, pp. 930-940, 2008; cited on IDS).*
Abdel-Salam et al (Arab J. Biotech, 7(1), pp. 141-155, 2004).*
Fischer et al (Journal of Immunological Methods, 1999, 226(1-2):1-10).*
Santi et al (Vaccine, 2008, 26: 1846-1854).*
Waterhouse et al (Journal of Virological Methods, 1984, 8: 321-329).*
Takebe et al (Plant & Cell Physiol., 1968, 9:115-124).*
Valat et al (Plant Science, 2006, 170: 739-747).*
Riazunnisa et al (Physiologia Plantarum, 2007, 129: 679-686).*
Abtahl et al (J. Agric. Food Chem, 1997, 45: 4768-4772).*
Facchini et al (Plant Physiology, 1999, 120: 653-663).*
Prakash et al (J. Biosci., 1997, 3:339-344).*
Fido et al (2004, Protein Extraction from Plant Tissues. In: Cutler P. (eds) Protein Purification protocols, vol. 244, pp. 21-27).*
Shoji, Yoko, et al. (Vaccine 26.23 (2008): 2930-2934). (Year: 2008).*

Requirement for Restriction/Election dated Sep. 27, 2012 by the USPTO for U.S. Appl. No. 12/863,772, filed Aug. 26, 2010 (1st Named Inventor—D'Aoust) (9 pages).
Non-final Rejection dated Dec. 14, 2012 by the USPTO for U.S. Appl. No. 12/863,772, filed Aug. 26, 2010 (1st Named Inventor—D'Aoust) (8 pages).
Non-final Rejection dated Oct. 4, 2012 by the USPTO for U.S. Appl. No. 12/669,033, filed Jun. 11, 2010 (1st Named Inventor—D'Aoust) (10 pages).
Requirement for Restriction/Election dated Mar. 25, 2013 by the USPTO for U.S. Appl. No. 13/748,531, filed Jan. 23, 2013 (1st Named Inventor—D'Aoust) (9 pages).
Garten. Influenza A Virus (A/California/04/2009 H1N1) segment 4 hamegglutinin (HA) gene, Genbank Acces. FJ966082 (2009).
U.S. Appl. No. 61/220,161, filed Jun. 24, 2009, M. Couture.
U.S. Appl. No. 13/380,346, filed Apr. 17, 2012, M. Couture.
U.S. Appl. No. 61/446,889, filed Mar. 23, 2011, M. Couture.
Preliminary Amendment filed Sep. 20, 2013 for U.S. Appl. No. 14/006,552, filed Mar. 22, 2012 (D'Aoust et al.) (5 pages).
Decision regarding Petition mailed Nov. 26, 2013 for U.S. Appl. No. 13/380,346, filed Apr. 17, 2012 (Couture et al.) (3 pages).
Amendment in Response to Decision regarding Petition with renewed Petition filed Nov. 16, 2013 for U.S. Appl. No. 13/380,346, filed Apr. 17, 2012 (Couture et al.) (13 pages).
Non-Final Office Action dated Nov. 5, 2013 for U.S. Appl. No. 13/380,346, filed Apr. 17, 2012 (Couture et al.) (12 pages).
Decision regarding Petition mailed Oct. 10, 2013 for U.S. Appl. No. 13/380,346, filed Apr. 17, 2012 (Couture et al.) (3 pages).
Preliminary Amendment filed Aug. 20, 2013 for U.S. Appl. No. 13/380,346, filed Apr. 17, 2012 (Couture et al.) (26 pages).
Request for Participation in PPH Program filed Aug. 20, 2013 for U.S. Appl. No. 13/380,346, filed Aug. 17, 2012 (Couture et al.) (2 pages).
Preliminary Amendment filed Mar. 20, 2012 for U.S. Appl. No. 13/380,346, filed Apr. 17, 2012 (Couture et al.) (4 pages).
International Preliminary Report on Patentability dated Jan. 4, 2012 for PCT/CA2010/000983 filed Jun. 25, 2010 and published as WO 2010/148511 on Dec. 29, 2010 (Medicago, Inc. // Couture et al.) (9 pages).
International Search Report dated Dec. 29, 2010 for PCT/CA2010/000983 filed Jun. 25, 2010 and published as WO 2010/148511 on Dec. 29, 2010 (Medicago, Inc. // Couture et al.) (5 pages).
Written Opinion dated Sep. 14, 2010 for PCT/CA2010/000983 filed Jun. 25, 2010 and published as WO 2010/148511 on Dec. 29, 2010 (Medicago, Inc. // Couture et al.) (8 pages).
International Preliminary Report on Patentability dated Sep. 24, 2013 for PCT/CA2012/050180 filed Mar. 23, 2012 and published as WO 2012/126123 on Sep. 27, 2012 (Medicago, Inc. // Couture et al.) (8 pages).
International Search Report dated Sep. 27, 2012 for PCT/CA2012/050180 filed Mar. 23, 2012 and published as WO 2012/126123 on Sep. 27, 2012 (Medicago, Inc. // Couture et al.) (5 pages).
Written Opinion dated Jun. 11, 2012 for PCT/CA2012/050180 filed Mar. 23, 2012 and published as WO 2012/126123 on Sep. 27, 2012 (Medicago, Inc. // Couture et al.) (7 pages).
Anonymous: Protoplast preparation (from plant tissue), Dec. 1, 2006 (URL: http://www.ivaan.com/protocols/128.html) (1 page).
Ellis, R.J. The molecular chaperone concept. Seminars in Cell Biology, 1990 (1):1-9 (abstract only).
Influenza A Virus (A/Caledonia/20/99(H1N1)) hemagglutinin (HA) gene. Genbank Accession No. AY289929, 2003. (2 pages).
Klopfleisch, R., et al. Neurotropism of Highly Pathogenic Avian Influenza Virus A/Chicken/Indonesia/2003 (H5N1) in Experimentally Infected Pigeons (*Columbia livia* f. domestica). Vet Pathol. vol. 43, pp. 463-470, 2006.
Sorensen, Hans Peter. Advanced genetic strategies for recombinant protein expression in *Escherichia coli*. Journal of Biotechnology 115 (2005) pp. 113-128.
Wang, W et al. Role of plant heat-shock proteins and molecular chaperones in the abiotic stress response. TRENDS in Plant Science, vol. 9:5, 2004, pp. 244-252.
Whitelam, G. The Production of Recombinant Proteins in Plants. (J Sci Food Agric, 68, pp. 1-9, 1995).

(56) References Cited

OTHER PUBLICATIONS

Yigzaw, Y., et al. Exploitation of the Adsorptive Properties of Depth Filters for Host Cell Protein Removal during Monoclonal Antibody Purification. Biotechnol. Prog. 2006, vol. 22, pp. 288-296.
Yokoyama, Naoaki, et al. Co-expression of human chaperone Hsp70 and Hsdj or Hsp40 co-factor increases solubility of overexpressed target proteins in insect cells. Biohimica et Biophysica Acta 1493 (2000) pp. 119-124.
Notice of Acceptance dated Dec. 17, 2014 2014 by the Australian Patent Office for AU 2010/300033 (1st Named Inventor—Couture; Applicant—Medicago Inc.) (3 pages).
Examination Report dated Dec. 17, 2014 by the Australian Patent Office for AU 2010/300034 filed on Sep. 21, 2010 (1st Named Inventor—Couture; Applicant—Medicago Inc.) (4 pages).
Examination Report dated Jun. 13, 2013 by the Australian Patent Office for AU 2009/202819 filed on Jan. 12, 2009 (1st Named Inventor—Couture; Applicant—Medicago Inc.) (3 pages).
Examination Report dated Nov. 6, 2013 by the Australian Patent Office for AU 2010/300034 filed on Sep. 21, 2010 (1st Named Inventor—Couture; Applicant—Medicago Inc.) (4 pages).
Notice of Allowance dated Aug. 14, 2013 for CA 2,707,235 by the Canadian Intellectual Property Office filed Jan. 12, 2009 (1st Named Inventor—D'Aoust; Applicant—Medicago Inc.) (1 page).
Office Action dated Jun. 2, 2014 for CA 2,730,185 by the Canadian Intellectual Property Office filed Jan. 12, 2009 (1st Named Inventor—D'Aoust; Applicant—Medicago Inc.) (2 pages).
Office Action dated Sep. 26, 2013 for CA 2,615,372 by the Canadian Intellectual Property Office filed Jan. 21, 2008 (1st Named Inventor—D'Aoust; Applicant—Medicago Inc.) (3 pages).
Decision on Rejection dated Feb. 20, 2014 by the State IP Office of China for CN 200980134868.8 (Applicant—Medicago, Inc.) (5 pages).
Decision on Rejection dated May 28, 2014 by the State IP Office of China for CN 20108004233.0. (Applicant—Medicago, Inc.) (13 pages).
Office Action dated Jul. 29, 2013 by the State IP Office of China for CN 201080042336.4 (Applicant—Medicago, Inc.) (18 pages).
Office Action issued Nov. 19, 2013 by the State IP Office of China for CN 20108004233.0. (Applicant - Medicago, Inc.) (17 pages).
Office Action dated Sep. 23, 2014 by the State IP Office of China for CN 201310021693.8. (Applicant—Medicago, Inc.) (16 pages).
Second Office Action dated Apr. 24, 2014 by the State IP Office of China for CN 201080042336.4. (Applicant—Medicago, Inc.) (10 pages).
Office Action dated Nov. 15, 2014 by the State IP Office of China for CN 201080042336.4. (Applicant—Medicago, Inc.) (18 pages).
Office Action dated Jan. 13, 2014 by the State IP Office of China for CN 201310021693.8. (Applicant—Medicago, Inc.) (9 pages).
Office Action dated Dec. 26, 2013 by the Eurasian Patent Organization for application EA 201001198 (Applicant—Medicago Inc.) (2 pages).
Office Action dated Sep. 3, 2014 by the Eurasian Patent Organization for application EA 201001198 (Applicant—Medicago Inc.) (3 pages).
Office Action dated Aug. 27, 2013 for Egyptian application EG PCT 61/2010 (Applicant—Medicago, Inc.) (12 pages).
Office Action dated Sep. 3, 2014 for Egyptian application EG PCT 61/2010 (Applicant—Medicago, Inc.) (15 pages).
Supplemental Examination Report dated Oct. 6, 2014 by the European Patent Office for EP 10818190.0 which was filed Sep. 21, 2010 and published as WO 2011/035422 on Mar. 31, 2011 (1st Named Inventor—Vezina; Applicant Medicago, Inc.) (5 pages).
Exam Report dated Oct. 23, 2013 by the European Patent Office for EP 10818190.0 which was filed Sep. 21, 2010 and published as WO 2011/035422 on Mar. 31, 2011 (1st Named Inventor—Vezina; Applicant—Medicago, Inc.) (4 pages).
Supplemental Examination Report dated Aug. 18, 2014 by the European Patent Office for EP 10818191.8 which was filed Sep. 21, 2010 and published as WO 2011/035423 on Mar. 31, 2011 (1st Named Inventor—Vezina; Applicant Medicago, Inc.) (5 pages).
Exam Report dated Oct. 23, 2013 by the European Patent Office for EP 10818191.8 which was filed Sep. 21, 2010 and published as WO 2011/035423 on Mar. 31, 2011 (1st Named Inventor—Vezina; Applicant—Medicago, Inc.) (4 pages).
Office Action dated Sep. 22, 2014 for Indonesian application ID W-0020102481 (Applicant—Medicago Inc.) (3 pages).
Office Action dated May 10, 2013 for Indonesian application ID W-0020102481 (Applicant—Medicago Inc.) (4 pages).
Office Action dated Jan. 9, 2015 for Indonesian application ID W-0020102481 (Applicant—Medicago Inc.) (3 pages).
Office Action dated Sep. 28, 2014 by the Israeli Registrar of Patents for application IL 218393 (Applicant—Medicago Inc.) (2 pages).
Office Action dated Oct. 21, 2014 by the Israeli Registrar of Patents for application IL 218422 (Applicant—Medicago Inc.) (2 pages).
Office Action dated Aug. 18, 2013 by the Israeli Registrar of Patents for application IL 203018. (Applicant—Medicago Inc.) (3 pages).
Final Office Action dated Jan. 16, 2014 by the Japanese Patent Office for application JP 2011-516934 (1st Named Inventor—Couture; Applicant—Medicago, Inc.) (3 pages).
Patent No. 5551780 granted to by the Japanese Patent Office for application No. 2012-530060 on May 30, 2014. (Applicant—Medicago, Inc.) (1 page).
Office Action dated Aug. 30, 2013 by the Japanese Patent Office for application JP 2010-542486 (1st Named Inventor—Couture; Applicant—Medicago, Inc.) (6 pages).
Office Action dated Jul. 17, 2013 by the Japanese Patent Office for application JP 2010-516334 (1st Named Inventor—Couture; Applicant—Medicago, Inc.) (8 pages).
Office Action dated Jun. 11, 2013 by the Japanese Patent Office for JP 2012-530059 filed Jan. 12, 2009 (1st Named Inventor—D'Aoust; Applicant—Medicago Inc.) (2 pages).
Office Action dated Oct. 22, 2014 for JP 2012-530059 by the Japanese Patent Office filed Jan. 12, 2009 (1st Named Inventor—D'Aoust; Applicant—Medicago Inc.) (6 pages).
Office Action dated Oct. 29, 2014 for JP 2012-530060 by the Japanese Patent Office filed Jan. 12, 2009 (1st Named Inventor—D'Aoust; Applicant—Medicago Inc.) (9 pages).
Office Action dated Jan. 15, 2015 by the Japanese Patent Office for application JP 2011-516934 (1st Named Inventor—Couture; Applicant—Medicago, Inc.) (10 pages).
Notice of Ground for Preliminary Rejection dated Dec. 22, 2014 but the Korean Intellectual Property Office for Application No. 10-2010-7002538 1st Named Inventor—D'Aoust; Applicant—Medicago Inc.) (14 pages).
Office Action dated Dec. 5, 2013 by the Mexican Institute of Industrial Property for MX/a/2010/007962 (Applicant—Medicago, Inc.) (5 pages).
Office Action dated Aug. 27, 2014 by the Mexican Institute of Industrial Property for MX/a/2012/003372 (Applicant—Medicago, Inc.) (6 pages).
Office Action dated Feb. 16, 2015 by the Mexican Institute of Industrial Property for MX/a/2012/003373 (Applicant—Medicago, Inc.) (4 pages).
Office Action dated Jul. 14, 2014 by the Mexican Institute of Industrial Property for MX/a/2012/003373 (Applicant—Medicago, Inc.) (2 pages).
Office Action dated Sep. 15, 2014 for Malaysian application PI2010000142 (Applicant—Medicago, Inc.) (3 pages).
Letters Patent 598508 dated Jun. 4, 2014 by the Intellectual Property Office of New Zealand (Applicant—Medicago, Inc.) (1 page).
Letters Patent 598481 issued Jun. 4, 2014 by the Intellectual Property Office of New Zealand (Applicant—Medicago, Inc.) (1 page).
Office Action dated Nov. 12, 2014 by the Russian Patent Office for Russian App. 2012115996 (Applicant—Medicago, Inc.) (3 pages).
Office Action dated Sep. 29, 2014 by the Russian Patent Office for Russian App. 2012115996 (Applicant—Medicago, Inc.) (8 pages).
Office Action dated Jun. 19, 2014 by the Russian Patent Office for Russian App. 2012115996 (Applicant—Medicago, Inc.) (4 pages).
Office Action dated Oct. 21, 2013 by the Russian Patent Office for Russian application 2011105073/10 (Applicant—Medicago, Inc.) (10 pages).

(56) References Cited

OTHER PUBLICATIONS

Certificate of Grant of Patent 187500 issued Aug. 26, 2014 by the Singapore Registry of Patents for SG Application No. 2013004577 (Applicant—Medicago, Inc.) (2 pages).
Search Report and Written Opinion dated Apr. 16, 2014 by the Hungarian Intellectual Property Office for SG 2012/014,718 filed Sep. 19, 2010 (1st Named Inventor—D'Aoust; Applicant—Medicago Inc.) (13 pages).
Final Office Action dated Jun. 18, 2014 for U.S. Appl. No. 13/748,531, filed Jan. 23, 2013 and published as US 2013/0142826 on Jun. 6, 2013 (1st Named Inventor—D'aoust; Applicant—Medicago, Inc.) (29 pages).
Final Office Action dated Dec. 5, 2014 for U.S. Appl. No. 13/734,886, filed Jan. 23, 2013 and published as US 2013/0183341 on Jul. 18, 2013 (1st Named Inventor—D'aoust; Applicant—Medicago, Inc.) (12 pages).
Final Office Action dated Mar. 20, 2014 for U.S. Appl. No. 13/734,886, filed Jan. 23, 2013 and published as US 2013/0183341 on Jul. 18, 2013 (1st Named Inventor—D'aoust; Applicant—Medicago, Inc.) (14 pages).
Non-Final Office Action dated Feb. 11, 2015 for U.S. Appl. No. 13/003,570, filed Apr. 26, 2011 and published as US 2011/0293650 on Dec. 1, 2011 (1st Named Inventor—D'aoust; Applicant—Medicago, Inc.) (21 pages).
Final Office Action dated May 8, 2014 for U.S. Appl. No. 13/003,570, filed Apr. 26, 2011 and published as US 2011/0293650 on Dec. 1, 2011 (1st Named Inventor—D'aoust; Applicant—Medicago, Inc.) (30 pages).
Non-Final Office Action dated Jul. 17, 2013 for U.S. Appl. No. 13/003,570, filed Apr. 26, 2011 and published as US 2011/0293650 on Dec. 1, 2011 (1st Named Inventor—D'aoust; Applicant—Medicago, Inc.) (33 pages).
Non-Final Office Action dated Nov. 25, 2013 for U.S. Appl. No. 13/734,886, filed Jan. 23, 2013 and published as US 2013/0183341 on Jul. 18, 2013 (1st Named Inventor—D'aoust; Applicant—Medicago, Inc.) (72 pages).
Non-Final Office Action dated Jan. 5, 2015 for U.S. Appl. No. 13/748,531, filed Jan. 23, 2013 and published as US 2013/0142826 on Jun. 6, 2013 (1st Named Inventor—D'aoust; Applicant—Medicago, Inc.) (21 pages).
Non-Final Office Action dated Sep. 12, 2013 for U.S. Appl. No. 13/748,531, filed Jan. 23, 2013 and published as US 2013/0142826 on Jun. 6, 2013 (1st Named Inventor—D'aoust; Applicant—Medicago, Inc.) (47 pages).
Letters Patent issued Oct. 30, 2013 by the South African Patent Office for 2010/05917 (Applicant—Medicago, Inc.) (1 page).
Power, et al., "A Simple Method for the Isolation of Very Large Numbers of Leaf Protoplasts by using Mixtures of Cellulase and Pectinase", Biochem J., 111(5) (1969) p. 33P.
Takahashi, et al., "A high-throughput screen of cell-death-inducing factors in Nitotiana benthamiana identifies a novel MAPKK that mediates INF1-induced cell death signaling and non-host resistance to Pseudomonas cichorii", The Plant Journal (2007) 49, pp. 1030-1040.
Notice of Allowance dated Jun. 1, 2015 by the Canadian Intellectual Property Office for application CA 2,730,185, filed on Jan. 12, 2009 (1st Named Inventor—D'Aoust; Applicant—Medicago Inc.) (2 pages).
Third Office Action dated May 26, 2015 by the State Intellectual Property Office of the People's Republic of China for application CN 201310021693.8 (Applicant—Medicago, Inc. (5 pages—English Translation).
Decision on Rejection dated May 28, 2015 by the State Intellectual Property Office of the People's Republic of China for application CN 201080042336.4 (Applicant—Medicago, Inc. (7 pages—English Translation).
Communication Pursuant to Article 94(3) EPC issued Sep. 25, 2015 by the European Patent Office for EP 10818190.0 which was filed Sep. 21, 2010 and published as WO 2011/035422 on Mar. 31, 2011 (1st Named Inventor—Vezina; Applicant—Medicago, Inc.) (6 pages).

Certificate of Grant dated May 27, 2015 by the Israeli Registrar of Patents for application IL 203018. (Applicant—Medicago Inc.) (5 pages).
Exam Report dated Aug. 6, 2015 by the Patent Office of India for application 212/DELNP/2010, filed on Jan. 12, 2010 (Applicant—Medicago, Inc.) (2 pages).
Office Action dated May 27, 2015 by the Patent Office of Japan for application JP 2014-039035 (Applicant—Medicago, Inc.) (7 pages—English Translation).
Decision to Grant dated Jul. 20, 2015 by the Korean Intellectual Property Office for Application No. 10-2010-7002538 (Inventor—D'Aoust // Applicant—Medicago Inc.) (4 pages—Korean Original and English Translation).
Notice of Grounds for Refusal dated May 21, 2015 by the Korean Intellectual Property Office for Application No. 10-2010-7018343 (Inventor—D'Aoust // Applicant—Medicago Inc.) (30 pages—Korean Original and English Translation).
Office Action dated Jun. 24, 2015 by the Federal Service for Intellectual Property of the Russian Federation for application RU 2012115661 (2 pages—English Translation).
Notice of Allowance dated May 5, 2015 by the Federal Service for Intellectual Property of the Russian Federation for application RU 012115996 (9 pages—Translation).
Final Office Action issued by the USPTO dated Jun. 25, 2015 for U.S. Appl. No. 13/734,886, filed Jan. 23, 2013 and published as US 2013/0183341 on Jul. 18, 2013 (1st Named Inventor—D'Aoust; Applicant—Medicago, Inc.) (34 pages).
Final Office Action issued by the USPTO dated Jun. 23, 2015 for U.S. Appl. No. 13/748,531, filed Jan. 23, 2013 and published as US 2013/0142826 on Jun. 6, 2013 (1st Named Inventor—D'Aoust; Applicant—Medicago, Inc.) (12 pages).
Denis, et al., "Immunogenicity of papaya mosaic virus-like particles fused to a hepatitis C virus epitope: Evidence for the critical function of multimerization," Virology 363 (2007) pp. 59-68.
Liu, et al., "Cowpea mosaic virus-based systems for the production of antigens and antibodies in plants," Vaccine 23 (2005) pp. 1788-1792.
Novel Swine-Origin Influenza A (H1N1) Virus Investigation Team, "Emergence of a Novel Swine-Origin Influenza A (H1N1) Virus in Humans," New England Journal of Medicine vol. 360, No. 25, (2009) (12 pages).
Certificate of Grant dated Nov. 12, 2015 by the Australian Patent Office for AU 2010/300033 (1st Named Inventor—Couture; Applicant—Medicago Inc.) (1 page).
English Translation of Eurasian Office Action dated Oct. 1, 2015 for application EA 201001198 (1st Named Inventor—Couture; Applicant—Medicago Inc.) (3 pages).
Fourth Office Action dated Nov. 26, 2015 by the State Intellectual Property Office of the People's Republic of China for application CN 201310021693.8 (Applicant—Medicago, Inc.) (7 pages—English Translation).
Translated Summary of Indonesian Office Action dated Dec. 3, 2015 for application W-00201201507 (Applicant—Medicago, Inc.) (1 page).
Notification of Allowability dated Sep. 18, 2015 for Indonesian application ID W-0020102481 (Applicant—Medicago Inc.) (2 pages).
Notice of Final Rejection dated Jan. 22, 2016 by the Korean Intellectual Property Office for Application No. 10-2010-7018343 (Applicant—Medicago Inc.) (4 pages // English Translation).
Advisory Action issued by the USPTO dated Nov. 3, 2015 for U.S. Appl. No. 13/734,886, filed Jan. 4, 2013 and published as US 2013/0183341 on Jul. 18, 2013 (1st Named Inventor—D'Aoust; Applicant—Medicago, Inc.) (3 pages).
Non-Final Office Action issued by the USPTO dated Feb. 12, 2016 for U.S. Appl. No. 13/734,886, filed Jan. 4, 2013 and published as US 2013/0183341 on Jul. 18, 2013 (1st Named Inventor—D'Aoust; Applicant—Medicago, Inc.) (13 pages).
Final Office Action issued by the USPTO dated Oct. 6, 2015 for U.S. Appl. No. 13/748,531, filed Jan. 23, 2013 and published as US 2013/0142826 on Jun. 6, 2013 (1st Named Inventor—D'Aoust; Applicant—Medicago, Inc.) (12 pages).
Non-Final Office Action issued by the USPTO dated Dec. 2, 2015 for U.S. Appl. No. 13/003,570, which was filed on Apr. 26, 2011 and

(56) References Cited

OTHER PUBLICATIONS published as US 2011/10293650 on Dec. 1, 2011 (1st Named Inventor—D'aoust; Applicant—Medicago, Inc.) (15 pages).
Examination Report was dated Oct. 28, 2016 by the Korean Intellectual Property Office for KR Application No. UAE/P/ 0286/2012 which was filed on Mar. 21, 2012 (Applicant—Medicago) (9 pages).
Notice of Reexamination was dated May 26, 2016 by the State Intellectual Property Office of the People's Republic of China for CN Application No. 201080042333.0, which was filed on Sep. 31, 010 and published as 102549148A on Jul. 4, 2012 (Applicant—Medicago Inc.) (4 pages).
Communication pursuant to Article 94(3) EPC was dated Jul. 27, 2016 by the European Patent Office for EP Application No. 10818190.0, which was filed on Sep. 21, 2010 (Applicant—Medicago Inc.) (5 pages).
Notice of Defects in Patent Application was dated Jul. 27, 2016 by the State of Israel Ministry of Justice Registrar of Patents for IL Application No. 218393 (Applicant—Medicago Inc.) (4 pages).
Notice for Grounds of Refusal was dated Sep. 29, 2016 by the Korean Intellectual Property Office for KR Application No. 10-2012-7009357, which was filed on Apr. 12, 2012 (Applicant—Medicago Inc.) (8 pages).
Examination Report was dated Mar. 31, 2016 by the Intellectual Property Corporation of Malaysia for MY Application No. PI2012001251, which was filed on Sep. 21, 2010 (Applicant—Medicago Inc.) (3 pages).
Office Action dated Jun. 28, 2016 by the Intellectual Property Office of the Philippines Bureau of Patents for PH Application No. 1/2012/500566, which was filed on Mar. 20, 2012(Applicant—Medicago Inc.) (4 pages).
Examination Report was dated Oct. 28, 2016 by the Korean Intellectual Property Office for KR Application No. UAE/P/ 0287/2012 which was filed on Mar. 21, 2012 (Applicant—Medicago) (6 pages).
Office Action was dated Oct. 4, 2016 by the Canadian Patent Office for CA Application No. CA 2,772,964, which was filed on Sep. 21, 2010 and published as 2,772,964 on Mar. 31, 2011 (Applicant—Medicago) (4 pages).
Notice of Reexamination was dated May 26, 2016 by the State Intellectual Property Office of the People's Republic of China for CN Application No. 201080042336.4, which was filed on Sep. 21, 010 and published as 102549008A on Jul. 4, 2012 (Applicant—Medicago Inc.) (11 pages).
Communication pursuant to Article 94(3) EPC was dated Nov. 17, 2015 by the European Patent Office for EP Application No. 10818191.8, which was filed on Sep. 21, 2010 (Applicant—Medicago Inc.) (6 pages).
Communication pursuant to Article 94(3) EPC was dated Jul. 26, 2016 by the European Patent Office for EP Application No. 10818191.8, which was filed on Sep. 21, 2010 (Applicant—Medicago Inc.) (4 pages).
Notice of Defects in Patent Application was issued on May 23, 2016 by the State of Israel Ministry of Justice Registrar of Patents for IL Application No. 218422 (Applicant—Medicago Inc.) (2 pages).
Office Action dated Jun. 10, 2016 by the Intellectual Property Office of the Philippines Bureau of Patents for PH Application No. 1/2012/500565, which was filed on Mar. 20, 2012(Applicant—Medicago Inc.) (3 pages).
Examination Report was dated Nov. 10, 2016 by the Intellectual Property Office of Singapore for SG Application No. 201201471-8, which was filed on Sep. 21, 2010 (Applicant—Medicago Inc.) (11 pages).
Written Opinion was dated May 17, 2016 by the Intellectual Property Office of Singapore for SG Application No. 201201471-8, which was filed on Sep. 21, 2010 (Applicant—Medicago Inc.) (11 pages).
Final Rejection was dated Nov. 25, 2016 by the U.S. Patent and Trademark Office for U.S. Appl. No. 13/497,767, which was filed on Mar. 22, 2012 and published as US 2013-0067807 A1 on Mar. 21, 2013 (Inventor—Louis-Philippe Vezina et al.) (12 pages).
Examination Report was dated Oct. 28, 2016 by the Korean Intellectual Property Office for KR Application No. UAE/P/ 0043/2010 which was filed on Jan. 13, 2010 (Applicant—Medicago) (7 pages).
Fifth Office Action was dated Aug. 12, 2016 by the State Intellectual Property Office of the People's Republic of China for CN Application No. 201310021693.8, which was filed on Jan. 12, 2009 and published as 103122354A on May 29, 2013(Applicant—Medicago Inc.) (6 pages).
Office Action was issued on May 18, 2016 by the Intellectual Property Office of Egypt for EG Application No. PCT/ 61/2010 (Applicant—Medicago Inc.) (4 pages).
Office Action was dated Jul. 25, 2016 by the Intellectual Property Office of Indonesia for IN Application No. W-00201000109 (Applicant—Medicago Inc.) (1 page).
Notice for Grounds of Refusal was dated Jun. 2, 2016 by the Korean Intellectual Property Office for KR Application No. 10-2010-7018343, which was filed on Aug. 18, 2010 (Applicant—Medicago Inc.) (18 pages).
Notice of Allowance was dated May 31, 2016 by the U.S. Patent and Trademark Office for U.S. Appl. No. 13/734,886, filed Jan. 4, 2013 and granted as U.S. Pat. No. 9,452,210 on Sep. 27, 2016 (Applicant—Medicago Inc.) (5 pages).
Issue Notification was dated Sep. 7, 2016 by the U.S. Patent and Trademark Office for U.S. Appl. No. 13/734,886, filed Jan. 4, 2013 and granted as U.S. Pat. No. 9,452,210 on Sep. 27, 2016 (Applicant—Medicago Inc.) (1 page).
Notice of Allowance was dated May 26, 2016 by the U.S. Patent and Trademark Office for U.S. Appl. No. 13/748,531, filed Jan. 23, 2013 and granted as U.S. Pat. No. 9,458,470 on Oct. 4, 2016 (Applicant—Medicago Inc.) (8 pages).
Issue Notification was dated Sep. 14, 2016 by the U.S. Patent and Trademark Office for U.S. Appl. No. 13/748,531, filed Jan. 23, 2013 and granted as U.S. Pat. No. 9,458,470 on Oct. 4, 2016 (Applicant—Medicago Inc.) (1 page).
Notice of Allowance was dated Jun. 29, 2016 by the U.S. Patent and Trademark Office for U.S. Appl. No. 13/003,570, filed Apr. 26, 2011 and granted as U.S. Pat. No. 9,492,528 on Nov. 15, 2016 (Applicant—Medicago Inc.) (7 pages).
Issue Notification was dated Oct. 26, 2016 by the U.S. Patent and Trademark Office for U.S. Appl. No. 13/003,570, filed Apr. 26, 2011 and granted as U.S. Pat. No. 9,492,528 on Nov. 15, 2016 (Applicant—Medicago Inc.) (1 page).
Naito, Tadasuke, et al. "Involvement of Hsp90 in Assembly and Nuclear Import of Influenza Virus RNA Polymerase Subunits", Journal of Virology, (2007), 81(3):1339-1349.
GenBank Accession EF541394.1 "Influenza A virus (A/Indonesia/5/05(H5N1)) segment 4 hemagglutinin (HA) gene, complete cds" (2 pages).
Decision for Re-exmination was dated Dec. 21, 2016 by the SIPO for CN Application No. 201080042333.0, which was filed on Sep. 21, 2010 and published as CN 102549148A on Jul. 4, 2012 (Applicant—Medicago Inc.) (1 page).
Communication under Rule 71(3) EPC was dated Apr. 6, 2017 by the European Patent Office for EP Application No. EP10818190.0, which was filed on Sep. 21, 2010 and published as EP 2480658 A1 on Aug. 1, 2012 (Applicant—Medicago Inc.) (5 pages).
Decision to Grant a European patent pursuant to Article 97(1) EPC was dated Aug. 10, 2017 by the European Patent Office for EP Application No. EP10818190.0, which was filed on Sep. 21, 2010 and published as EP 2480658 A1 on Aug. 1, 2012 (Applicant—Medicago Inc.) (5 pages).
Notice of Grounds for Refusal was dated Mar. 15, 2017 by the Korean Patent Office for KR Application No. KR 20127010044, which was filed on Sep. 21, 2010 and published as KR 20120093223 A on Aug. 22, 2012 (Applicant—Medicago Inc.) (Original—5 pages // Translation—8 pages).
Non Final Rejection was dated Jun. 30, 2017 by the USPTO for U.S. Appl. No. 13/497,767, filed Mar. 22, 2012 and published as US 2013-0067807 A1 on Mar. 21, 2013(Inventor—Louis-Philippe Vezina) (14 pages).

(56) References Cited

OTHER PUBLICATIONS

Sixth Office Action was dated Mar. 28, 2017 by the SIPO for CN Application No. 201310021693, which was filed on Jan. 12, 2009 and published as CN 103122354 A on May 29, 2013 (Applicant—Medicago Inc.) (Original—5 pages // Translation—5 pages).
Notification of Reasons for Refusal was dated Dec. 26, 2016 by the Japanese Patent Office for JP Application No. 2016000233, which was filed on Jan. 4, 2016 and published as JP 2016052331 A on Apr. 14, 2016 (Applicant—Medicago Inc.) (Original—5 pages // Translation—3 pages).
Non Final Rejection was dated Apr. 6, 2017 by the USPTO for U.S. Appl. No. 15/256,119, filed Sep. 2, 2016 and published as US 2017-0088848 A1 on Mar. 30, 2017 (Applicant—Medicago Inc .; Inventor—Marc-Andre D'Aoust) (8 pages).
Attwood, T.K., Genomics: The Babel of Bioinformatics. Science. 2000; 290(5491):471-3.
Baker, D. and Sali, A., Protein Structure Prediction and Structural Genomics. Science. 2001; 294(5540):93-6 (24 pages).
Park, K.-H., Microbial Production of Yeast and Plant Cell Wall Lytic Enzyme. Research Report from the University of Seoul. 1988 (Only Summary in English) (64 pages).
Siminis, C.I. et al., Catalase is Differentially Expressed in Dividing and Nondividing Protoplasts. Plant Physiol. 1994; 105:1375-83.
Communication Under Rule 71(3) EPC dated Apr. 10, 2017 by the European Patent Office for Patent Application No. 10818191.8 (Inventor—Vezina et al.; Applicant—Medicago, Inc.) (6 pages).
Notice of Allowance dated Aug. 1, 2017 by the Intellectual Property Office of the Philippines for Patent Application No. 1/2012/500565, which was filed on Mar. 20, 2012 (Inventor—Vezina et al.; Applicant—Medicago, Inc.) (1 page).
Office Action dated Oct. 13, 2017 by the Canadian Intellectual Property Office for Patent Application No. 2,772,964 (Inventor—Vezina et al.; Applicant—Medicago, Inc.) (5 pages).
Office Action dated Oct. 13, 2017 by the Eurasian Intellectual Property Office for Patent Application No. 201001198 (Inventor—Vezina et al.; Applicant—Medicago, Inc.) (Translation Only—2 pages).
Office Action dated Nov. 13, 2017 by the Intellectual Property Office of India for Patent Application No. 2637/DELNP/2012 (Inventor—Vezina et al.; Applicant—Medicago, Inc.) (8 pages).
Office Action dated Nov. 14, 2017 by the Intellectual Property Office of Egypt for Patent Application PCT 61/2010 (Inventor—Vezina et al.; Applicant—Medicago, Inc.) (Translation Summary Only—1 page).
Office Action dated Jan. 18, 2018 by the Intellectual Property Office of India for Patent Application No. 2591/DELNP/2012 (Inventor—Vezina et al.; Applicant—Medicago, Inc.) (6 pages).
Decision of Final Rejection dated Jan. 26, 2018 by the Korean Intellectual Property Office for Patent Application No. 10-2012-7010044 (Inventor—Vezina et al.; Applicant—Medicago, Inc.) (Translation Only—7 pages).
Decision of Final Rejection dated Jan. 30, 2018 by the Korean Intellectual Property Office for Patent Application No. 10-2016-7010959 (Inventor—Vezina et al.; Applicant—Medicago, Inc.) (Translation Only—6 pages).
Notice of Allowance dated Feb. 28, 2018 by the Intellectual Property Office of the Philippines for Patent Application No. 1/2012/500566, which was filed on Mar. 20, 2012 (Inventor—Vezina et al.; Applicant—Medicago, Inc.) (1 page).
Examination Report dated Mar. 16, 2018 by the Korean Intellectual Property Office for Patent Application No. UAE/P/0768/2010 (Inventor—Vezina et al.; Applicant—Medicago, Inc.) (10 pages).
Notice of Grounds for Preliminary Rejection dated April 5, 3018 by the Korean Intellectual Property Office for Patent Application No. 10-2018-7005775, whihc was filed on Feb. 27, 2018 (Inventor—Vezina et al.; Applicant—Medicago, Inc.) (Translation Only—8 pages).
Final Office Action dated Apr. 6, 2018 by the U.S. Patent and Trademark Office for U.S. Appl. No. 13/497,767, which was filed on Mar. 22, 2012 and published as US 2013/0067807 on Mar. 21, 2013 (Inventor—Vezina et al.; Applicant—Medicago, Inc.) (12 pages).
Martin, P.A.W. et al., Transformation of *Bacillus thuringiensis* Protoplasts by Plasmid Deoxyribonucleic Acid. J Bacteriol. 1981; 145(2):980-3.
Prakash, A.H. et al., Plant Regeneration from Protoplasts of *Capsicum annuum* L. cv. California Wonder. J Biosci. 1997; 22(3):339-44.
Schmidt, R. and Poole, R.J., Isolation of Protoplasts and Vaculoes from Storage Tissue of Red Beet. Plant Physiol. 1980; 66:25-8.
Twyman, R.M. et al., Molecular Farming in Plants: Host Systems and Expression Technology. Trends in Biotechnol. 2003; 21(12): 570-8.
Non-Final Office Action dated Oct. 5, 2018 by the U.S. Patent and Trademark Office for U.S. Appl. No. 13/497,767, filed Mar. 22, 2012 and published as US 2013/0067807 on Mar. 21, 2013 (Inventor—Vezina et al.; Applicant—Medicago, Inc. et al.; (19 pages).
Final Rejection was dated Jul. 29, 2019 by the USPTO for U.S. Appl. No. 13/497,767, filed Mar. 22, 2012 and published as US 2013/0067807 A1 on Mar. 21, 2013 (Inventor—Louis-Philippe Vezina) ( Pages).
Non-Final Office Action dated Jun. 1, 2020 by the U.S. Patent and Trademark Office for U.S. Appl. No. 13/497,767, which was filed on Mar. 22, 2012 and published as US 2013/0067807 A1 on Jul. 12, 2012 (Inventor—Louis-Philippe Vezina) (23 pages).
U.S. Appl. No. 61/220,161, filed Jun. 24, 2009, Couture.
International Preliminary Report on Patentability dated Nov. 12, 2009 for PCT/CA2008/001281 filed Jul. 11, 2008 and published as WO 2009/009876 on Jan. 22, 2009 (Medicago, Inc. // D'Aoust et al.) (11 pages).
International Search Report and Written Opinion dated Oct. 7, 2008 for PCT/CA2008/001281 filed Jul. 11, 2008 and published as WO 2009/009876 on Jan. 22, 2009 (Medicago, Inc. // D'Aoust et al.) (15 pages).
International Preliminary Report on Patentability dated Jan. 11, 2011 for PCT/CA2009/000941 filed Jul. 7, 2009 and published as WO 2010/003235 on Jan. 14, 2010 (Medicago, Inc. // Couture et al.) (1 pages).
International Search Report and Written Opinion dated Sep. 10, 2009 for PCT/CA2009/000941 filed Jul. 7, 2009 and published as WO 2010/003235 on Jan. 14, 2010 (Medicago, Inc. // Couture et al.) (13 pages).
International Preliminary Report on Patentability dated Nov. 5, 2010 for application PCT/CA2009/001040 filed Jul. 15, 2009 and published as WO 2010/006452 (Medicago, Inc. // Couture et al.) (14 pages).
International Search Report and Written Opinion dated Nov. 10, 2009 for PCT/CA2009/001040 filed Jul. 15, 2009 and published as WO 2010/006452 on Jan. 14, 2010 (Medicago, Inc. // Couture et al.) (13 pages).
International Preliminary Report on Patentability dated Jul. 27, 2010 for PCT/CA2009/000032 filed Jan. 12, 2009 and published as WO 2009/076778 on Jun. 25, 2009 (Medicago, Inc. // D'Aoust et al.) (9 pages).
International Search Report and Written Opinion dated Apr. 30, 2009 for PCT/CA2009/000032 filed Jan. 12, 2009 and published as WO 2009/076778 on Jun. 25, 2009 (Medicago, Inc. // D'Aoust et al.) (17 pages).
International Preliminary Report on Patentability dated Nov. 5, 2010 for PCT/CA2009/000926 filed Jul. 2, 2009 and published as WO 2010/003225 on Jan. 14, 2010 (Medicago, Inc. // D'Aoust et al.) (15 pages).
International Search Report and Written Opinion dated Oct. 1, 2009 for PCT/CA2009/000926 filed Jul. 2, 2009 and published as WO 2010/003225 on Jan. 14, 2010 (Medicago, Inc. // D'Aoust et al.) (17 pages).
International Search Report dated Jan. 6, 2011 for PCT/CA2010/001488 filed Sep. 21, 2010 and published as WO 2011/035422 on Mar. 31, 2011 (Medicago, Inc. // Vezina et al.) (5 pages).
Written Opinion dated Jan. 6, 2011 for PCT/CA2010/001488 filed Sep. 21, 2010 and published as WO 2011/035422 on Mar. 31, 2011 (Medicago, Inc. // Vezina et al.) (6 pages).

(56) References Cited

OTHER PUBLICATIONS

International Preliminary Report on Patentability dated Mar. 27, 2012 for PCT/CA2010/001488 filed 09/21/10 and published as WO 2011/035422 on Mar. 31, 2011 (Medicago, Inc. // Vezina et al.) (7 pages).
International Search Report dated Nov. 30, 2010 for PCT/CA2010/001489 filed Sep. 21, 2010 and published as WO 2011/035423 on Mar. 31, 2011 (Medicago, Inc. // Vezina et al.) (4 pages).
Written Opinion dated Nov. 30, 2010 for PCT/CA2010/001489 filed 09/21/10 and published as WO 2011/035423 on Mar. 31, 2011 (Medicago, Inc. // Vezina et al.) (6 pages).
International Preliminary Report on Patentability dated Mar. 27, 2012 for PCT/CA2010/001489 filed Sep. 21, 2010 and published as WO 2011/035423 on Mar. 31, 2011 (Medicago, Inc. // Vezina et al.) (7 pages).
Air GM. Sequence relationships among the hemagglutinin genes of 12 subtypes of influenza A Virus, Proc Natl Acad Sci USA 78, pp. 7639-7643 (1981).
Amtzen, et al. Plant-derived vaccines and antibodies: potential and limitations, Vaccine 23, pp. 1753-1756 (2005).
Ausubel, et al. Chapter 9: Transfection by Electroporation, Current Protocols in Molecular Biology, John Wiley & Sons, New York (1998 and Supplements in 2001).
Aymard-Henry M, et al. InfluenzaVirus neuraminidase and neuraminidase-inhibition test procedures. Bull. Org. mond. Sante. Bull. Wld Hlth Org. 48, pp. 199-202 (1973).
Bao, et al. The influenza virus resource at the National Center for Biotechnology Information, J Virol 82, pp. 596-601 (2008).
Berger, et al. Plant sterols: factors affecting their efficacy and safety as functional food ingredients, Lipids in Health and Disease 3, pp. 1-19 (2004).
Berman, et al. Correspondence: announcing the worldwide Protein Data Bank, Nat Struct Biol 10, p. 980 (2003).
Bilang, et al. The 3'-terminal region of the hygromycin-B-resistance gene is important for its activity in *Escherichia coli* and Nicotiana tabacum, Gene 100, pp. 247-250 (1991).
Bollag, et al. Purified JC virus T antigen derived from insect cells preferentially interacts with binding site II of the viral core origin under replication conditions, Virology 218, pp. 81-93 (1996).
Borisjuk, et al. Expression of avian flu antigen for bird immunization, Plant Biology & Botany Abstract Search (1 page) (2007).
Bouic PJD, et al. Plant sterols and sterolins: a review of their immune-modulating properties, Alt Med Rev 4, pp. 170-177 (1999).
Bouic PJD. Sterols and sterolins: new drugs for the immune system?, Drug Discovery Today 7, pp. 775-778 (2002).
Bouic PJD. The role of phytosterols and phytosterolins in immune modulation: a review of the past 10 years, Curr Opin Clin Nutrition Metabolic Care 4, pp. 471-475 (2001).
Bright RA, et al. Impact of glycosylation on the immunogenicity of a DNA-based influenza H5 HA vaccine, Virology 308, pp. 270-278 (2003).
Bright RA, et al. Influenza virus-like particles elicit broader immune responses than whole virion inactivated influenza virus or recombinant hemagglutinin, Vaccine 25, pp. 3871-3878 (2007).
Brigneti, et al. Viral pathogenicity determinants are suppressors of transgene silencing in Nicotiana benthamiana, EMBO J 17, pp. 6739-6746 (1998).
Chandler GL. Influenza hemagglutinin expression in Nicotiana tabacum and Nicotiana benthamiana, Dissertation, Baylor University (70 pages) (2007).
Chandrasekaran, et al. Glycan topology determines human adaptation of avian H5N1 virus hemagglutinin, Nat Biotechnol 26, pp. 107-113 (2008).
Charland N, et al. An innovative VLP-based technology to respond to global influenza vaccine needs, Seasonal and Pandemic Influenza Conference (2 pages) (2008).
Chen BJ, et al. Influenza virus hemagglutinin and neuraminidase, but not the matrix protein, are required for assembly and budding of plasmid-derived virus-like particles, J Virol 81, pp. 7111-7123 (2007).

Chen, et al. Stabilizing the glycosylation pattern of influenza B hemagglutinin following adaptation to growth in eggs, Vaccine 26, pp. 361-371 (2008).
Chiba M, et al. Diverse suppressors of RNA silencing enhance agroinfection by a viral replicon, Virology 346, pp. 7-14 (2006).
Cosgrove, D. Loosening of Plant Cell Walls by Expansins, Nature, vol. 407, pp. 321-326 (2000).
Crawford, et al. Baculovirus-derived hemagglutinin vaccines protect against lethal influenza infections by avian H5 and H7 subtypes, Vaccine 17, pp. 2265-2274 (1999).
Cross, et al. Studies on influenza haemagglutinin fusion peptide mutants generated by reverse genetics, EMBO J 20, pp. 4432-4442 (2001).
D'Aoust MA, et al. Influenza virus-like particles produced by transient 1-38 expression in Nicotiana benthamiana induce a protective immune response against a lethal viral challenge in mice, Plant Biotechnol J 6, pp. 930-940 (2008).
D'Aoust MA, et al. The production of hemagglutinin-based virus-like 1-38 particles in plants: a rapid, efficient and safe response to pandemic influenza, Plant Biotechnol J 8, pp. 607-619 (2010).
Davey MR, et al. Plant protoplasts: status and biotechnological perspectives, Biotechnology Advances 23, pp. 131-171 (2005).
DeBlock M, et al. Transformation of Brassica napus and Brassica oleracea using Agrobacterium tumefaciens and the expression of the bar and neo genes in the transgenic plants, Plant Physiology 91, pp. 694-701 (1989).
Diaz-Vivancos P, et al. The apoplastic antioxidant system in Prunus: response to long-term plum pox virus infection, J Exp Bot 57, pp. 3813-3 824 (2006).
Firek et al. Secretion of a functional single-chain Fv protein in transgenic tobacco plants and cell suspension cultures, Plant Molecular Biology, vol. 23, Issue 4, pp. 861-870 (1993).
Fischer R, et al. Affinity-purification of a TMV-specific recombinant full-size antibody from a transgenic tobacco suspension culture, J Immunol Meth 226, pp. 1-10 (1999).
Fischer, et al. Towards molecular farming in the future: moving form diagnostic protein and antibody production in microbes to plants, Biotechnology and Applied Biochemistry, vol. 30, pp. 101-108 (1999).
Flandorfer, et al. Chimeric influenza A viruses with a functional influenza B virus neuraminidase or hemagglutinin, J Virol 77, pp. 9116-9123 (2003).
Frugis G, et al. MsJ1, an alfalfa DnaJ-like gene, is tissue-specific and transcriptionally regulated during cell cycle, Plant Mol Biol 40, pp. 397-408 (1999).
Galarza, et al. Virus-like particle (VLP) vaccine conferred complete protection against a lethal influenza virus challenge, Viral Immunol 18, pp. 244-251 (2005).
Gallagher, et al. Addition of carbohydrate side chains at novel sites on influenza virus hemagglutinin can modulate the folding, transport, and activity of the molecule, J Cell Biol 107, pp. 2059-2073 (1988).
Gallagher, et al. Glycosylation requirements for intracellular transport and function of the hemagglutinin of influenza virus, J Virol 66, pp. 7136-7145 (1992).
Gamblin, et al. The structure and receptor binding properties of the 1918 influenza hemagglutinin, Science 303, pp. 1838-1842 (2004).
Garcea & Gissmann. Virus-like particles as vaccines and vessels for the delivery of small molecules, Pharmaceut Biotechnol 15, pp. 513-517 (2004).
Garten R, et al. Emergence of a novel swine-origin influenza A (H1N1) virus in humans, New Eng J Med 361, pp. 1-10 (2009).
Garten, et al. Antigenic and genetic characteristics of swine-origin 2009 A(H1N1) Influenza viruses circulating in Humans. Science, vol. 325, pp. 197-201 (2009).
Garten, et al. Emergence of a Novel Swine-Origin Influenza A (H1N1) Virus in Humans. New England Journal of Medicine, vol. 360, No. 25 (2009).
Garten. Influenza A Virus (A/Califomia/04/2009 H1N1) segment 4 hamegglutinin (HA) gene, Genbank Acces. FJ966082 (2009).
Gillim-Ross, et al. Emerging respiratory viruses: challenges and vaccine strategies, Clin Microbiol Rev 19, pp. 614-636 (2006).

(56) References Cited

OTHER PUBLICATIONS

Giridhar G, et al. Increased protoplast yield from oat leaves and bean internodes by non-injurious mechanical perturbation, Protoplasma 151, pp. 151-157 (1989).
Giritch, et al. Rapid High-Yield Expression of Full-Size IgG Antibodies in Plants Coinfected with Noncompeting Viral Vectors, PNAS, vol. 103, No. 40, pp. 14701-14706 (2006).
Golovkin, et al. Expression of avian flu antigen for bird immunization, Plant Biol Bot, 1 page (2007) (Abstract).
Gomez-Puertas, et al. Efficient formation of influeza virus-like particles: dependence on the expression levels of viral proteins, J Gen Virol 80, pp. 1635-1645 (1999).
Gomez-Puertas, et al. Influenza virus matrix protein is the major driving force in virus budding, J Virol 74, pp. 11536-11547 (2000).
Gomord & Faye. Posttranslational modification of therapeutic proteins in plants, Curr Opin Plant Biol 7, pp. 171-181 (2004).
Gomord, et al. Biopharmaceutical Production in Plants: Problems, Solutions and Opportunities, Trends in Biotechnology, vol. 23, No. 11, pp. 559-565 (2005).
Greco R, et al. Production of recombinant HIV-1/HBV virus-like particles in Nicotiana tabacum and *Arabidopsis thaliana* plants for a bivalent plant-based vaccine, Vaccine 25, pp. 8228-8240 (2007).
Grgacic & Anderson. Virus-like particles: Passport to immune recognition, Methods 40, pp. 60-65 (2006).
Grierson & Covey. Chapter 7: Genetic Transformation of Plants by Agrobacterium, in Plant Molecular Biology (19 pages) (1988).
Grierson & Covey. Chapter 8: Plant Viruses, in Plant Molecular Biology (26 pages) (1988). Grierson, et al. Chapter 9: Genetic Engineering of Plants, in Plant Molecular Biology (20 pages) (1988).
Grierson, et al. Chapter 9: Genetic Engineering of Plants, in Plant Molecular Biology (20 pages) (1988).
Guerche, et al. Direct gene transfer by electroporation in Brassica napus, Plant Science 52, pp. 111-116 (1987).
Gupta, et al. O-Glycbase version 4.0: a revised database of O-glycosylated proteins, Nucl Acids Res 27, pp. 370-372 (1999).
Hahn BS, et al. Expression of hemagglutinin-neuraminidase protein of Newcastle disease Virus in transgenic tobacco, Plant Biotechnol Rep 1, pp. 85-92 (2007).
Hamilton A, et al. Two classes of short interfering RNA in RNA silencing, EMBO J 21, pp. 4671-4679 (2002).
Harbury, et al. A switch between the two-, three-, and four-stranded coiled coils in GCN4 leucine zipper mutants, Science 262, pp. 1401-1407 (1993).
Hartl FU. Molecular chaperones in cellular protein folding, Nature 381, pp. 571-580 (1996).
Hellwig, et al. Plant Cell Cultures for the Production of Recombinant Proteins, Nature Biotechnology, vol. 22, No. 11, pp. 1415-1422 (2004).
Horimoto, et al. Generation of influenza A Viruses with chimeric (Type A/B) hemagglutinins, J Virol 77, pp. 8031-8038 (2003).
Horsch, et al. A simple and general method for transferring genes into plants, Science 227, pp. 1229-1231 (1985).
Houston, N., et al. Phylogenetic Analyses Identify 10 Classes of the Protein Disulfide Isomerase Family in Plants, Including Single-Domain Protein Disulfide Isomerase-Related Proteins. Plant Physiology, vol. 137, pp. 762-778 (2005).
Howell, et al. Cloned Cauliflower Mosaic Virus DNA infects turnips (*Brassica rapa*), Science 208, p. 1265 (1980).
Huang Z, et al. Virus-like particle expression and assembly in plants: 1-38 hepatitis Band Norwalk viruses, Vaccine 23, pp. 1851-1858 (2005).
Huang, et al. A DNA replicon system for rapid high-level production of virus-like particles in plants, Biotechnol Bioeng 103, 706-714 (2009).
Huang, et al. High Level Rapid Production of Full-Size Monoclonal Antibodies in Plants by a Single-Vector DNA Replicon System, Biotechnology System, Biotechnology and Bioengineering, vol. 106, No. 1, (19 pages) (2010).
Huang, et al. Plant-derived measles virus hemagglutinin protein induces neutralizing antibodies in mice, Vaccine 19, pp. 2163-2171 (2001).
Hull, et al. Human-Derived, Plant-Produced monoclonal Antibody for the Treatment of Anthrax, Vaccine 23, pp. 2082-2086 (2005).
Influenza A virus (A/California/04/2009(H1N1)) segment 4 hemagglutinin (HA) gene, Complete DNA Sequence, GenBank (2 pages) (Aug. 2010).
Ito T, et al. Receptor specificity of Influenza A viruses correlates with the agglutination of erythrocytes from different animal species, Virology 227, pp. 493-499 (1997).
Johansen, et al. Silencing on the Spot. Induction and Suppression of RNA Silencing in the Agrobacterium-Mediated Transient Expression System, Plant Physiology, vol. 126, No. 3, pp. 930-938 (2001).
Johansson BE. Immunization with influenza A virus hemagglutinin and neuraminidase produced in recombinant baculovirus results in a balanced and broadened immune response superior to conventional vaccine, Vaccine 17, pp. 2073-2080 (1999).
Kanda Y, et al. Comparison of biological activity among nonfucosylated therapeutic IgG1 antibodies with three different N-linked Fc oligosaccharides: the high-mannose, hybrid, and complex types, Glycobiol 17, pp. 104-118 (2007).
Kang SM, et al. Influenza vaccines based on virus-like particles, Virus Res 143, pp. 140-146 (2009).
Kaufman PB, et al. Chapter 16: Gene Tranfer and Expression in Plants, in Handbook of Molecular and Cellular Methods in Biology and Medicine (29 pages) (1995).
Klein, et al. High-velocity microprojectiles for delivering nucleic acids into living cells, Nature 327, pp. 70-73 (1987).
Knossow, et al. Variation and infectivity neutralization in influenza, Immunology 119, pp. 1-7 (2006).
Kobayashi, et al. Chaperones Hsp70 and Hsp40 Suppress Aggregate Formation and Apoptosis in Cultured Neuronal Cells Expressing Truncated Androgen Receptor Protein with Expanded Polyglutamine Tract, J Biol.l Chem., vol. 275, No. 12, pp. 8772-8778 (2000).
Latham, et al. Formation of wild-type and chimeric influenza virus-like particles following simultaneous expression of only four structural proteins, J Virol 75, pp. 6154-6165 (2001).
Lefebvre, et al. Characterization of lipid rafts from Medicago truncatula root plasma membranes: a proteomic study reveals the presence of a raft-associated redox system, Plant Physiol 144, pp. 402-418 (2007).
Lin, et al. Genomic analysis of the Hsp70 superfamily in *Arabidopsis thaliana*, Cell Stress & Chaperones, pp. 201-208 (2001).
Liu & Lomonossoff. Agroinfection as a rapid method for propagating Cowpea mosaic virus-based constructs, J Virol Meth 105, pp. 343-348 (2002).
Low D, et al. Future of antibody purification, J Chromatography B 848, pp. 48-63 (2007).
Ma, et al. The production of recombinant pharmaceutical proteins in plants, Nature Reviews Genetics, vol. 4, pp. 794-805 (2003).
Macala, et al. Analysis of brain lipids by high performance thin-layer chromatography and densitometry, J Lipid Res 24, pp. 1243-1250 (1983).
Macario, AJL. Heat-shock proteins and molecular chaperones: implications for pathogenesis, diagnostics, and therapeutics, Int J Clin Lab Res 25, pp. 59-70 (1995).
Mansour, et al. Plasma membrane lipid alterations induced by NaCI in winter wheat roots, Physiologia Plantarum 92, pp. 473-478 (1994).
Marozin S, et al. Antigenic and genetic diversity among swine influenza A H1N1 and H1N2 Viruses in Europe, J Gen Virol 83, pp. 735-745 (2002).
Mason HS, et al. Expression of hepatitis B surface antigen in transgenic plants, Proc Natl Acad Sci USA 89, pp. 11745-11749 (1992).
Mason HS, et al. Expression of Norwalk Virus capsid protein in transgenic tobacco and potato and its oral immunogenicity in mice, Proc Natl Acad Sci USA 93, pp. 5335-5340 (1996).
Mattanovich, et al. Efficient transformation of *Agrobacterium* spp. by electroporation, Nucl Acids Res 17, p. 6747 (1989).
McCauley & Mahy. Structure and function of the influenza Virus genome, Biochem J 211, pp. 281-294 (1983).

(56) References Cited

OTHER PUBLICATIONS

McCormick AA, et al. Rapid production of specific vaccines for lymphoma by expression of the tumor-derived single-chain Fv epitopes in tobacco plants, Proc Natl Acad Sci USA 96, pp. 703-708 (1999).
Medeiros R, et al. Hemagglutinin residues of recent human A (H3N2) Influenza Viruses that contribute to the inability to agglutinate chicken erythrocytes, Virology 289, pp. 74-85 (2001).
Mena I, et al. Rescue of a synthetic chloramphenicol acetyltransferase RNA into influenza Virus-like particles obtained from recombinant plasmids, J Virol 70, pp. 5016-5024 (1996).
Mett, et al. A plant-produced influenza subunit vaccine protects ferrets against Virus challenge, Influenza and Other Respiratory Viruses 2, pp. 33-40 (2008).
Miki & Iyer. Chapter 35: Fundamentals of Gene Transfer in Plants, in Plant Metabolism (23 pages) (1997).
Moehnke, et al. The expression of a mountain cedar allergen comparing plant-viral apoplastic and yeast expression systems, Biotechnol Lett 30, pp. 1259-1264 (2008).
Mongrand S, et al. Lipid rafts in higher plant cells: purification and characterization of Triton X-100-insoluble microdomains from Tobacco plasma membrane, J Bilo Chem 279, pp. 36277-36286 (2004).
Musiychuk K, et al. A launch vector for the production of vaccine antigens in plants, Influenza Other Resp Vir 1, pp. 19-25 (2007).
Nakahara, et al. Glycoconjugate Data Bank: Structures—an annotated glycan primary structure verification service, Nucl Acids Res 36, pp. D368-D371 (2008).
Nayak & Reichl. Neuraminidase activity assays for monitoring MDCK cell culture derived influenza virus, J Virol Meth 122, pp. 9-15 (2004).
Nemchinov, et al. Transient expression of the ectodomain of matrix protein 2 (M2e) of avian influenza A virus in plants. Protein Expression and Purification, vol. 56, pp. 153-159 (2007).
Neuhause G, et al. Transgenic rapeSeed plants obtained by the microinjection of DNA into microspore-derived embryoids, Theor Appl Genet 75, pp. 30-36 (1987).
Neumann, et al. Plasmid-driven formation of influenza virus-like particles, J Virol 74, pp. 547-551 (2000).
Newell JM, et al. Vacuole development in cultured evacuolated oat mesophyll protoplasts, J Exp Botany 49, pp. 817-827 (1998).
Nishimura, et al. Isolation of intact plastids from protoplasts from Castor Bean endosperm, Plant Physiol 62, pp. 40-43 (1978).
Nuttall, et al. ER-resident chaperone interactions with recombinant antibodies in transgenic plants, Eur J Biochem 269, pp. 6042-6051 (2002).
Olsen, et al. Immunogenicity and efficacy of baculovirus-expressed and DNA-based equine influenza virus hemagglutinin vaccines in mice, Vaccine 15, pp. 1149-1156 (1997).
Parsell DA & Lindquist S. The function of heat-shock proteins in stress tolerance: degradation and reactivation of damaged proteins, Ann Rev Genet 27, pp. 43 7-496 (1993).
Paszkowski & Saul. Direct Gene Transfer to Plants, in Methods for Plant Molecular Biology (19 pages) (1988).
Pereira-Leal JB, et al. The origins and evolution of functional modules: lessons from protein complexes, Philos Trans R Soc Lond B Biol Sci 361, pp. 507-517 (2006).
Petersen & Alfermann. Chapter 17: Plant Cell Cultures. Biotechnology Set, Second Edition, Section 1.3, pp. 578-580 (2008).
Plotkin, et al. Hemagglutinin sequence clusters and the antigenic evolution of influenza A virus, Proc Natl Acad Sci USA 99, pp. 6263-6268 (2002).
Potrykus I, et al. Protoplasts: Isolation, Culture, Plant Regeneration, in Methods for Plant Molecular Biology (31 pages) (1988).
Potter & Heller. Transfection by electroporation, Curr Prot Mol Biol (12 pages) (2003).
Power JB, et al. Fusion and Transformation of Plant Protoplasts, in Methods for Plant Molecular Biology (19 pages) (1988).
Pushko P, et al. Influenza virus-like particles comprised of the HA, NA, and M1 proteins of H9N2 influenza virus induce protective immune responses in BALB/c mice, Vaccine 23, pp. 5751-5759 (2005).
Pwee, et al. The pea plastocyanin promoter directs cell-specific but not full light-regulated expression in transgenic tobacco plants, Plant J 3, pp. 437-449 (1993).
Quan FS, et al. Virus-like particle vaccine induces protective immunity against homologous and heterologous strains of influenza virus, J Virol 81, pp. 3514-3524 (2007).
Razdan MK. Chapter 12: Somatic Hybridisation and Cybridisation, in Introduction to Plant Tissue Culture (30 pages) (2003).
Regnard, et al. High Level Protein Expression in Plants Through the Use of a Novel Autonomously Replicating Geminivirus Shuttle Vector, Plant Biotechnology Journal, vol. 8, pp. 38-46 (2010).
Rivard, et al. An in-built proteinase inhibitor system for the protection of recombinant proteins recovered from transgenic plants, Plant Biotechnology Journal, vol. 4, No. 3, pp. 359-368 (2006).
Rowe, et al. Detection of antibody to avian influenza A (H5N1) virus in human serum by using a combination of serologic assays, J Clin Microbiol 37, pp. 937-943 (1999).
Roy, et al. Virus-like particles as a vaccine delivery system: myths and facts, Human Vaccines 4, pp. 5-12 (2008).
Saelens, et al. Protection of Mice Against a Lethal Influenza Virus Challenge After Immunization with Yeast-Derived Secreted Influenza Virus Hemagglutinin, Eur. J. Biochem, vol. 260, pp. 166-175 (1999).
Sainsbury F & Lomonossoff GP. Extremely high-level and rapid transient protein production in plants without the use of viral replication, Plant Physiol 148, pp. 1212-1218 (2008).
Sainsbury F, et al. Expression of multiple proteins using full-length and deleted versions of cowpea mosaic virus RNA-2, Plant Biotechnol J 6, pp. 82-92 (2008).
Saint-Jore-Dupas C, et al. From planta to pharma with glycosylation in the toolbox, TRENDS in Biotechnol 25, pp. 317-323 (2007).
Selenko N, et al. CD20 antibody (C2B8)-induced apoptosis of lymphoma cells promotes phagocytosis by dendritic cells and cross-priming of CD8+ cytotoxic T cells, Leukemia 15, pp. 1619-1626 (2001).
Salzberg, et al. Genome analysis linking recent European and African influenza (H5N1) viruses, Emerg Infect Dis 13, pp. 713-718 (2007).
Santi L, et al. An efficient plant viral expression system generating orally immunogenic Norwalk virus-like particles, Vaccine 26, pp. 1846-1854 (2008).
Scheid OM, et al. Reversible inactivation of a transgene in *Arabidopsis thaliana*, Mol Gen Genet 228, pp. 104-112 (1991).
Schillberg S, et al. Apoplastic and cytosolic expression of full-size antibodies and antibody fragments in Nicotiana tabacum, Transgenic Res 8, pp. 255-263 (1999).
Schillberg S, et al. Molecular farming of recombinant antibodies in plants, Cell Mol Life Sci 60, pp. 433-445 (2003).
Schuler & Zielinski. Chapter 8: Transformation of Leaf Discs with Agrobacterium, in Methods in Plant Molecular Biology (14 pages) (1989).
Shoji Y, et al. Plant-expressed HA as a seasonal influenza vaccine candidate, Vaccine 26, pp. 2930-2934 (2008).
Shorrosh BS & Dixon RA. Molecular cloning of a putative plant endomembrane protein resembling vertebrate protein disulfide-isomerase and a phosphatidylinositol-specific phospholipase C, Proc Natl Acad Sci USA 88, pp. 10941-10945 (1991).
Shorrosh, B. et al. Sequence analysis and developmental expression of an alfalfa protein disulfide isomerase. Plant Molecular Biology, vol. 19, pp. 319-321 (1992).
Skehel & Wiley. Receptor binding and membrane fusion in virus entry: the influenza hemagglutinin, Ann Rev Biochem 69, pp. 531-569 (2000).
Smith ML, et al. Structural characterization of plant-derived hepatitis B surface antigen employed in oral immunization studies, Vaccine 21, pp. 4011-4021 (2003).
Spitsin, et al. Immunological assessment of plant-derived avian flu H5/HA1 variants, Vaccine, vol. 27, No. 9, pp. 1289-1292 (2009).

(56) References Cited

OTHER PUBLICATIONS

Squires B, et al. BioHealthBase: informatics support in the elucidation of influenza virus host-pathogen interactions and virulence, Nucl Acids Res 36, pp. D497-D503 (2008).
Sriraman, et al. Recombinant anti-hCG antibodies retained in the endoplasmic reticulum of transformed plants lack core-xylose and core-α(1,3)-fucose residues, Plant Biotechnol J 2, pp. 279-287 (2004).
Staehelin LA. The plant ER: a dynamic organelle composed of a large number of discrete functional domains, Plant J 11, pp. 1151-1165 (1997).
Suzuki Y. Sialobiology of influenza: molecular mechanism of host range variation of influenza viruses, Biol Pharm Bull 28, pp. 399-408 (2005).
Szyperski T, et al. Structure comparison of human glioma pathogenesis-related protein GliPR and the plant pathogenesis-related protein P14a indicates a functional link between the human immune system and a plant defense system, Proc Natl Acad Sci 95, pp. 2262-2266 (1998).
Tacket CO, et al. Human immune responses to a novel Norwalk virus vaccine delivered in transgenic potatoes, J Infect Dis 182, pp. 302-305 (2000).
Toukach, et al. Sharing of worldwide distributed carbohydrate-related digital resources: online connection of the Bacterial Carbohydrate Structure DataBase and Glycosciences.de, Nucl Acids Res 35, pp. D280-D286 (2007).
Treanor, et al. Safety and immunogenicity of a baculovirus-expressed hemagglutinin influenza vaccine: a randomized controlled trial, JAMA 297, pp. 1577-1582 (2007).
Vaccaro L, et al. Plasticity of influenza haemagglutinin fusion peptides and their interaction with lipid bilayers, Biophys J 88, pp. 25-36 (2005).
Van Ree R, et al. β(1,2)-xylose and α(1,3)-fucose residues have a strong contribution in IgE binding to plant glycoallergens, J Biol Chem 275, pp. 11451-11458 (2000).
Varsani, et al. Expression of Human papillomavirus type 16 major capsid protein in transgenic *Nicotiana tabacum* cv. Xanthi, Arch Viral 148, pp. 1771-1786 (2003).
Vezina, et al. Transient co-expression for fast and high-yield production of antibodies with human-like N-glycans in plants, Plant Biotechnol J 7, pp. 442-455 (2009).
Vigerust, et al. N-Linked Glycosylation Attenuates H3N2 Influenza Viruses, Journal of Virology, vol. 81, No. 16, pp. 8593-8600 (2007).
Voinnet O, et al. An enhanced transient expression system in plants based on suppression of gene silencing by the p19 protein of tomato bushy stunt virus, Plant J 33, pp. 949-956 (2003).
Wagner, et al. Interdependence of hemagglutinin glycosylation and neuraminidase as regulators of influenza virus growth: a study by reverse genetics, J Virol 74, pp. 6316-6323 (2000).
Wakefield, et al. RNA-binding properties of influenza A virus matrix protein M1, Nucl Acids Res 17, pp. 8569-8580 (1989).
Wang, et al. Expression and purification of an influenza hemagglutinin—one step closer to a recombinant protein-based influenza vaccine, Vaccine 24, pp. 2176-2185 (2006).
Wei, et al. Comparative efficacy of neutralizing antibodies elicited by recombinant hemagglutinin proteins from avian H5N1 influenza virus, J Virol 82, pp. 6200-6208 (2008).
Weldon, et al. Enhanced Immunogenicity of Stabilized Trimeric Soluble Influenza Hemagglutinin, PLOS One, Vol. 5, No. 9, e12466, pp. 1-8 (2010).
Wilson IBH, et al. Core a1,3-fucose is a key part of the epitope recognized by antibodies reacting against plant N-linked oligosaccharides and is present in a wide variety of plant extracts, Glycobiol 8, pp. 651-661 (1998).
Wydro M, et al. Optimization of transient Agrobacterium-mediated gene expression system in leaves of Nicotania benthamiana, Acta Biochimica Polonica 53, pp. 289-298 (2006).
Preliminary Amendment filed Mar. 22, 2012 for U.S. Appl. No. 13/497,767, filed Sep. 21, 2010 (Vezina et al.) (4 pages).
Preliminary Amendment filed Jan. 23, 2013 for U.S. Appl. No. 13/748,531, filed Jan. 23, 2013 (D'Aoust et al.) (3 pages).
Requirement for Restriction/Election dated Mar. 25, 2013 for U.S. Appl. No. 13/748,531, filed Jan. 23, 2013 (D'Aoust et al.) (9 pages).
Response to Requirement for Restriction/Election filed Apr. 25, 2013 for U.S. Appl. No. 13/748,531, filed Jan. 23, 2013 (D'Aoust et al.) (3 pages).
Non-Final Rejection dated Sep. 23, 2013 for U.S. Appl. No. 13/748,531, filed Jan. 23, 2013 (D'Aoust et al.) (10 pages).
Preliminary Amendment filed Jan. 13, 2010 for U.S. Appl. No. 12/669,033, filed Jun. 11, 2010 (D'Aoust et al.) (7 pages).
Requirement for Restriction/Election dated Aug. 13, 2012 for U.S. Appl. No. 12/669,033, filed Jun. 11, 2010 (D'Aoust et al.) (8 pages).
Response to Requirement for Restriction/Election filed Sep. 11, 2012 for U.S. Appl. No. 12/669,033, filed Jun. 11, 2010 (D'Aoust et al.) (5 pages).
Non-Final Rejection dated Oct. 4, 2012 for U.S. Appl. No. 12/669,033, filed Jun. 11, 2010 (D'Aoust et al.) (10 pages).
Response to Non-Final Rejection filed Nov. 2, 2012 for U.S. Appl. No. 12/669,033, filed Jun. 11, 2010 (D'Aoust et al.) (2 pages).
Miscellaneous Communication dated May 21, 2012 for U.S. Appl. No. 12/669,033, filed Jun. 11, 2010 (D'Aoust et al.) (2 pages).
Notice of Abandonment dated Jul. 10, 2013 for U.S. Appl. No. 12/669,033, filed Jun. 11, 2010 (D'Aoust et al.) (2 pages).
Notice of Abandonment dated Jul. 25, 2013 for U.S. Appl. No. 12/863,772, filed Jul. 20, 2010 (D'Aoust et al.) (2 pages).
Non-Final Rejection dated Dec. 14, 2012 for U.S. Appl. No. 12/863,772, filed Jul. 20, 2010 (D'Aoust et al.) (8 pages).
Response to Requirement for Restriction/Election filed Oct. 29, 2012 for U.S. Appl. No. 12/863,772, filed Jul. 20, 2010 (D'Aoust et al.) (3 pages).
Requirement for Restriction/Election dated Sep. 27, 2012 for U.S. Appl. No. 12/863,772, filed Jul. 20, 2010 (D'Aoust et al.) (9 pages).
Preliminary Amendment filed Jul. 20, 2010 for U.S. Appl. No. 12/863,772, filed Jul. 20, 2010 (D'Aoust et al.) (7 pages).
$1^{st}$ Prelimianry Amendment filed Jan. 4, 2013 for U.S. Appl. No. 13/734,886, filed Jan. 4, 2013 (D'Aoust et al.) (3 pages).
$2^{nd}$ Prelimianry Amendment filed Mar. 22, 2013 for U.S. Appl. No. 13/734,886, filed Jan. 4, 2013 (D'Aoust et al.) (13 pages).
$3^{rd}$ Prelimianry Amendment filed Aug. 22, 2013 for U.S. Appl. No. 13/734,886, filed Jan. 4, 2013 (D'Aoust et al.) (5 pages).
Non-Final Rejection dated Nov. 25, 2013 for U.S. Appl. No. 13/734,886, filed Jan. 4, 2013 (D'Aoust et al.) (12 pages).
Preliminary Amendment filed Mar. 22, 2012 for U.S. Appl. No. 13/497,767, filed Mar. 22, 2012 (D'Aoust et al.) (4 pages).
Office Action dated May 21, 2013 by the Australian Intellectual Property Office for AU patent application No. 2008278222 filed on Jul. 11, 2008 (Medicago, Inc. // D'Aoust et al.) (3 pages).
Office Action dated Mar. 1, 2013 by the Canadian Intellectual Property Office for CA patent application No. 2,707,235 filed on Jan. 12, 2009 (Medicago, Inc. // D'Aoust et al.) (2 pages).
Office Action dated Sep. 28, 2012 by the Canadian Intellectual Property Office for CA patent application No. 2,707,235 filed on Jan. 12, 2009 (Medicago, Inc. // D'Aoust et al.) (2 pages).
Office Action dated Jun. 7, 2012 by the Canadian Intellectual Property Office for CA patent application No. 2,707,235 filed on Jan. 12, 2009 (Medicago, Inc. // D'Aoust et al.) (3 pages).
Office Action dated Jun. 1, 2011 by the Canadian Intellectual Property Office for CA patent application No. 2,707,235 filed on Jan. 12, 2009 (Medicago, Inc. // D'Aoust et al.) (5 pages).
Office Action dated Mar. 1, 2013 by the Canadian Intellectual Property Office for CA patent application No. 2,693,956 filed on Jul. 11, 2008 (Medicago, Inc. // D'Aoust et al.) (2 pages).
Office Action dated Oct. 16, 2012 by the Canadian Intellectual Property Office for CA patent application No. 2,693,956 filed on Jul. 11, 2008 (Medicago, Inc. // D'Aoust et al.) (2 pages).
Office Action dated Jan. 20, 2012 by the Canadian Intellectual Property Office for CA patent application No. 2,693,956 filed on Jul. 11, 2008 (Medicago, Inc. // D'Aoust et al.) (2 pages).
Office Action dated Sep. 22, 2011 by the Canadian Intellectual Property Office for CA patent application No. 2,693,956 filed on Jul. 11, 2008 (Medicago, Inc. // D'Aoust et al.) (3 pages).

(56) References Cited

OTHER PUBLICATIONS

Office Action dated Jan. 26, 2011 by the Canadian Intellectual Property Office for CA patent application No. 2,693,956 filed on Jul. 11, 2008 (Medicago, Inc. // D'Aoust et al.) (3 pages).
Office Action dated Nov. 27, 2012 by the State Intellectual Property Office of People's Republic of China for CN patent application No. 200980109781.5 filed on Jan. 12, 2009 (Medicago, Inc. // D'Aoust et al.) (5 pages).
Office Action dated Jan. 21, 2012 by the State Intellectual Property Office of People's Republic of China for CN patent application No. 200980109781.5 filed on Jan. 12, 2009 (Medicago, Inc. // D'Aoust et al.) (9 pages).
Office Action dated Feb. 21, 2013 by the State Intellectual Property Office of People's Republic of China for CN patent application No. 200880107072.9 filed on Jan. 12, 2009 (Medicago, Inc. // D'Aoust et al.) (6 pages).
Office Action dated Jul. 24, 2012 by the State Intellectual Property Office of People's Republic of China for CN patent application No. 200880107072.9 filed on Jan. 12, 2009 (Medicago, Inc. // D'Aoust et al.) (10 pages).
Office Action dated Sep. 27, 2011 by the State Intellectual Property Office of People's Republic of China for CN patent application No. 200880107072.9 filed on Jan. 12, 2009 (Medicago, Inc. // D'Aoust et al.) (8 pages).
Office Action dated May 30, 2013 by the State Intellectual Property Office of People's Republic of China for CN patent application No. 200980134868.8 filed on Jul. 2, 2009 (Medicago, Inc. // D'Aoust et al.) (5 pages).
Office Action dated Jul. 16, 2012 by the State Intellectual Property Office of People's Republic of China for CN patent application No. 200980134868.8 filed on Jul. 2, 2009 (Medicago, Inc. // D'Aoust et al.) (6 pages).
Office Action dated Mar. 1, 2013 by the State Intellectual Property Office of People's Republic of China for CN patent application No. 201080042333.0 (Medicago, Inc. // D'Aoust et al.) (12 pages).
Office Action dated Dec. 13, 2011 by the Eurasian Patent Office for EA patent application No. 201000195/28 (Medicago, Inc. // D'Aoust et al.) (4 Pages).
Office Action dated Jun. 13, 2012 by the Eurasian Patent Office for application No. 201000195/28 (Medicago, Inc. // D'Aoust et al) (1 Page).
Office Action dated Aug. 28, 2012 by the Eurasian Patent Office for application No. 201001198 filed Feb. 7, 2009 (Medicago, Inc. // D'Aoust et al) (5 Pages).
Office Action dated Apr. 24, 2013 by the Eurasian Patent Office for application No. 201001198 filed Feb. 7, 2009 (Medicago, Inc. // D'Aoust et al) (3 Pages).
Office Action dated Nov. 18, 2011 by the Egyptian Patent Office for EG patent application No. PCT 1222/2010 filed on Jan. 12, 2009 (Medicago, Inc. // D'Aoust et al.) (9 pages).
Office Action dated Oct. 26, 2012 by the European Patent Office for EP patent application No. 2008783201.0 filed on Jul. 11, 2008 (Medicago, Inc. // D'Aoust et al.) (XX pages).
Decision to Grant dated May 31, 2013 by the European Patent Office for EP patent application No. 2008783201.0 filed on Jul. 11, 2008 (Medicago, Inc. // D'Aoust et al.) (2 pages).
Extended European Search Report dated Sep. 31, 2010 by the European Patent Office for EP patent application No. 2008783201.0 filed on Jul. 11, 2008 (Medicago, Inc. // D'Aoust et al.) (9 pages).
European Search Report dated May 26, 2011 by the European Patent Office for EP patent application No. 2008783201.0 filed on Jul. 11, 2008 (Medicago, Inc. // D'Aoust et al.) (4 pages).
Extended European Search Report dated Mar. 7, 2011 by the European Patent Office for EP patent application No. 2009700061.6 filed on Jan. 12, 2009 (Medicago, Inc. // D'Aoust et al.) (11 pages).
Decision to Grant dated Aug. 17, 2012 by the European Patent Office for EP patent application No. 2009700061.6 filed on Jan. 12, 2009 (Medicago, Inc. // D'Aoust et al.) (1 page).
Extended European Search Report dated Aug. 9, 2011 by the European Patent Office for EP patent application No. 2009793741.1 filed on Jul. 2, 2009 (Medicago, Inc. // D'Aoust et al.) (9 pages).
Extended European Search Report dated Jul. 28, 2013 by the European Patent Office for EP patent application No. 108181900 filed on Sep. 21, 2010 (Medicago, Inc. // Vezina et al.) (6 pages).
Extended European Search Report dated Jan. 3, 2013 by the European Patent Office for EP patent application No. 108181918 filed on Sep. 21, 2010 (Medicago, Inc. // Vezina et al.) (5 pages).
Extended European Search Report dated Feb. 15, 2013 by the European Patent Office for EP patent application No. 121810774 filed on Jul. 2, 2009 (Medicago, Inc. // D'Aoust et al.) (8 pages).
Office Action dated Sep. 18, 2012 by the Indonesian Patent Office for ID application No. ID W-0020102481 filed Jul. 11, 2008 (Medicago, Inc. // D'Aoust et al.) (2 Pages).
Office Action dated Oct. 25, 2012 by the Registrar of Patents of Israel for IL patent application No. 210215 filed on Jul. 2, 2009 (Medicago, Inc. // D'Aoust et al.) (2 pages).
Office Action dated May 9, 2012 by the Registrar of Patents of Israel for IL patent application 206967 filed on Jan. 12, 2009 (Medicago, Inc. // D'Aoust et al.) (2 pages).
Office Action dated May 8, 2012 by the Registrar of Patents of Israel for IL patent application 203018 filed on Jan. 12, 2009 (Medicago, Inc. // D'Aoust et al.) (2 pages).
Office Action dated Mar. 6, 2013 by the Mexican Patent Office for MX patent application No. MX/a/2010/000525 filed on Jul. 11, 2008 (Medicago, Inc. // D'Aoust et al) (4 pages).
Office Action dated Mar. 6, 2013 by the Mexican Patent Office for MX patent application No. MX/a/2010/007962 filed on Jan. 12, 2009 (Medicago, Inc. // D'Aoust et al) (4 pages).
Office Action dated Mar. 6, 2013 by the Mexican Patent Office for MX application No. MX/a/2010/000459 filed on Jul. 22, 2009 (Medicago, Inc. // D'Aoust et al) (3 pages).
Examination Report dated Nov. 14, 2012 by the Intellectual Property Office of New Zealand for NZ patent application 598481 (2 pages).
Examination Report dated Nov. 15, 2012 by the Intellectual Property Office of New Zealand for NZ patent application 598508 (2 pages).
Examination Report dated Apr. 15, 2011 by the Intellectual Property Office of New Zealand for NZ patent application 590144 filed on Jul. 2, 2009 (Medicago, Inc. // D'Aoust et al.) (3 pages).
Examination Report dated Mar. 21, 2011 by the Intellectual Property Office of New Zealand for NZ patent application 587108 filed on Jan. 12, 2009 (Medicago, Inc. // D'Aoust et al.) (2 pages).
Examination Report dated Jun. 27, 2012 by the Intellectual Property Office of New Zealand for NZ patent application 587108 filed on Jan. 12, 2009 (Medicago, Inc. // D'Aoust et al.) (2 pages).
Examination Report dated Jan. 28, 2013 by the Intellectual Property Office of New Zealand for NZ patent application 587108 filed on Jan. 12, 2009 (Medicago, Inc. // D'Aoust et al.) (2 pages).
Examination Report dated Nov. 8, 2010 by the Intellectual Property Office of New Zealand for NZ patent application 582360 filed on Jul. 11, 2008 (Medicago, Inc. // D'Aoust et al.) (9 pages).
Office Action dated Apr. 5, 2013 by the Russian Patent Office for RU patent application RU 2011105073/10 (2 pages).
Singapore Written Opinion dated May 2, 2011 by the Danish Patent Office for SG patent application 201000090-9 filed on Jul. 11, 2008 (Medicago, Inc. // D'Aoust et al.) (16 pages).
Certificate of Grant of Patent dated Apr. 30, 2012 by the Intellectual Property Office of Singapore for application 201000090-9 filed on Jul. 11, 2008 (Medicago, Inc. // D'Aoust et al.) (2 pages).
Written Opinion dated Apr. 18, 2012 by the Intellectual Property Office of Singapore for application 201009568-5 filed on Jul. 11, 2008 (Medicago, Inc. // D'Aoust et al.) (20 pages).
Asenjo, J.A., et al. Selective Release of Recombinant Protein Particles (VLPs) from Yeast Using a Pure Lytic glucanase Enzyme. Nation Biotechnology, 1993, pp. 1-7.

* cited by examiner

Figure 2A

TTAATTAAGAATTCGAGCTCCACCGCGGAAACCTCCTCGGATTCCATTGCCCAGCTATCTGTCACTTTA
TTGAGAAGATAGTGGAAAAGGAAGGTGGCTCCTACAAATGCCATCATTGCGATAAAGGAAAGGCCATC
GTTGAAGATGCCTCTGCCGACAGTGGTCCCAAAGATGGACCCCCACCCACGAGGAGCATCGTGGAAAA
AGAAGACGTTCCAACCACGTCTTCAAAGCAAGTGGATTGATGTGATATCTCCACTGACGTAAGGGATG
ACGCACAATCCCACTATCCTTCGCAAGACCCTTCCTCTATATAAGGAAGTTCATTTCATTTGGAGAGGT
ATTAAAATCTTAATAGGTTTTGATAAAAGCGAACGTGGGGAAACCCGAACCAAACCTTCTTCTAAACTC
TCTCTCATCTCTCTTAAAGCAAACTTCTCTCTTGTCTTTCTTGCGTGAGCGATCTTCAACGTTGTCAGAT
CGTGCTTCGGCACCAGTACAACGTTTTCTTTCACTGAAGCGAAATCAAAGATCTCTTTGTGGACACGTA
GTGCGGCGCCATTAAATAACGTGTACTTGTCCTATTCTTGTCGGTGTGGTCTTGGGAAAAGAAAGCTTG
CTGGAGGCTGCTGTTCAGCCCCATACATTACTTGTTACGATTCTGCTGACTTTCGGCGGGTGCAATATC
TCTACTTCTGCTTGACGAGGTATTGTTGCCTGTACTTCTTTCTTCTTCTTGCTGATTGGTTCTATAA
GAAATCTAGTATTTTCTTTGAAACAGAGTTTTCCCGTGGTTTTCGAACTTGGAGAAAGATTGTTAAGCT
TCTGTATATTCTGCCCAAATTTGTCGGGCCC<u>ATGGAGAAAATAGTGCTTCTTCTTGCAATAGTCAGTCT
TGTTAAAAGTGATCAGATTTGCATTGGTTACCATGCAAACAATTCAACAGAGCAGGTTGACACAATCA
TGGAAAAGAACGTTACTGTTACACATGCCCAAGACATACTGGAAAAGACACACAACGGGAAGCTCTGC
GATCTAGATGGAGTGAAGCCTCTAATTTTAAGAGATTGTAGTGTAGCTGGATGGCTCCTCGGGAACCC
AATGTGTGACGAATTCATCAATGTACCGGAATGGTCTTACATAGTGGAGAAGGCCAATCCAACCAATG
ACCTCTGTTACCCAGGGAGTTTCAACGACTATGAGAACTGAAACACCTATTGAGCAGAATAAACCAT
TTTGAGAAAATTCAAATCATCCCCAAAAGTTCTTGGTCCGATCATGAAGCCTCATCAGGAGTTAGCTCA
GCATGTCCATACCTGGGAAGTCCCTCCTTTTTTAGAAATGTGGTATGGCTTATCAAAAAGAACAGTACA
TACCCAACAATAAAGAAAAGCTACAATAATACCAACCAAGAGGATCTTTTGGTACTGTGGGGAATTCA
CCATCCTAATGATGCGGCAGAGCAGACAAGGCTATATCAAAACCCAACCACCTATATTTCCATTGGGA
CATCAACACTAAACCAGAGATTGGTACCAAAAATAGCTACTAGATCCAAAGTAAACGGGCAAAGTGGA
AGGATGGAGTTCTTCTGGACAATTTTAAAACCTAATGATGCAATCAACTTCGAGAGTAATGGAAATTTC
ATTGCTCCAGAATATGCATACAAAATTGTCAAGAAAGGGGACTCAGCAATTATGAAAAGTGAATTGGA
ATATGGTAACTGCAACACCAAGTGTCAAACTCCAATGGGGGCGATAAACTCTAGTATGCCATTCCACA
ACATACACCCTCTCACCATCGGGGAATGCCCCAAATATGTGAAATCAAACAGATTAGTCCTTGCAACA
GGGCTCAGAAATAGCCCTCAAAGAGAGAGCAGAAGAAAAAGAGAGGACTATTTGGAGCTATAGCAG
GTTTTATAGAGGGAGGATGGCAGGGAATGGTAGATGGTTGGTATGGGTACCACCATAGCAATGAGCAG
GGGAGTGGGTACGCTGCAGACAAAGAATCCACTCAAAAGGCAATAGATGGAGTCACCAATAAGGTCA
ACTCAATCATTGACAAAATGAACACTCAGTTTGAGGCCGTTGGAAGGGAATTTAATAACTTAGAAAGG
AGAATAGAGAATTTAAACAAGAAGATGGAAGACGGGTTTCTAGATGTCTGGACTTATAATGCCGAACT
TCTGGTTCTCATGGAAAATGAGAGAACTCTAGACTTTCATGACTCAAATGTTAAGAACCTCTACGACAA
GGTCCGACTACAGCTTAGGGATAATGCAAAGGAGCTGGGTAACGGTTGTTTCGAGTTCTATCACAAAT
GTGATAATGAATGTATGGAAAGTATAAGAAACGGAACGTACAACTATCCGCAGTATTCAGAAGAAGCA
AGATTAAAAAGAGAGGAAATAAGTGGGGTAAAATTGGAATCAATAGGAACTTACCAAATACTGTCAAT
TTATTCAACAGTGGCGAGTTCCCTAGCACTGGCAATCATGATGGCTGGTCTATCTTTATGGATGTGCTC
CAATGGATCGTTACAATGCAGAATTTGCATTTAAAGGCCTATTTTCTTTAGTTTGAATTTACTGTTATTC
GGTGTGCATTTCTATGTTTGGTGAGCGGTTTTCTGTGCTCAGAGTGTGTTTATTTTATGTAATTTAATTT
CTTTGTGAGCTCCTGTTTAGCAGGTCGTCCCTTCAGCAAGGACACAAAAAGATTTTAATTTTATTAAAA
AAAAAAAAAAAAAGACCGGGAATTCGATATCAAGCTTATCGACCTGCAGATCGTTCAAACATTTGGC
AATAAAGTTTCTTAAGATTGAATCCTGTTGCCGGTCTTGCGATGATTATCATATAATTTCTGTTGAATT
ACGTTAAGCATGTAATAATTAACATGTAATGCATGACGTTATTTATGAGATGGGTTTTTATGATTAGAG
TCCCGCAATTATACATTTAATACGCGATAGAAAACAAAATATAGCGCGCAAACTAGGATAAATTATCG
CGCGCGGTGTCATCTATGTTACTAGATTCTAGAGTCTCAAGCTT<u>GGCGCGCC</u>

Figure 2B

MEKIVLLLAIVSLVKSDQICIGYHANNSTEQVDTIMEKNVTVTHAQDILEKTHNGKLCDLDGVKPLILRDCS
VAGWLLGNPMCDEFINVPEWSYIVEKANPTNDLCYPGSFNDYEELKHLLSRINHFEKIQIIPKSSWSDHEASS
GVSSACPYLGSPSFFRNVVWLIKKNSTYPTIKKSYNNTNQEDLLVLWGIHHPNDAAEQTRLYQNPTTYISIG
TSTLNQRLVPKIATRSKVNGQSGRMEFFWTILKPNDAINFESNGNFIAPEYAYKIVKKGDSAIMKSELEYGN
CNTKCQTPMGAINSSMPFHNIHPLTIGECPKYVKSNRLVLATGLRNSPQRESRRKKRGLFGAIAGFIEGGWQ
GMVDGWYGYHHSNEQGSGYAADKESTQKAIDGVTNKVNSIIDKMNTQFEAVGREFNNLERRIENLNKKM
EDGFLDVWTYNAELLVLMENERTLDFHDSNVKNLYDKVRLQLRDNAKELGNGCFEFYHKCDNECMESIR
NGTYNYPQYSEEARLKREEISGVKLESIGTYQILSIYSTVASSLALAIMMAGLSLWMCSNGSLQCRICI

Figure 5

```
AGAGGTACCCCGGGCTGGTATATTTATATGTTGTCAAATAACTCAAAAACCATAAAAGTTTAAGTTAGC
AAGTGTGTACATTTTTACTTGAACAAAAATATTCACCTACTACTGTTATAAATCATTATTAAACATTAG
AGTAAAGAAATATGGATGATAAGAACAAGAGTAGTGATATTTTGACAACAATTTTGTTGCAACATTTG
AGAAAATTTTGTTGTTCTCTCTTTTCATTGGTCAAAAACAATAGAGAGAGAAAAAGGAAGAGGGAGAA
TAAAAACATAATGTGAGTATGAGAGAGAAAGTTGTACAAAAGTTGTACCAAAATAGTTGTACAAATAT
CATTGAGGAATTTGACAAAAGCTACACAAATAAGGGTTAATTGCTGTAAATAAATAAGGATGACGCAT
TAGAGAGATGTACCATTAGAGAATTTTTGGCAAGTCATTAAAAAGAAAGAATAAATTATTTTTAAAAT
TAAAAGTTGAGTCATTTGATTAAACATGTGATTATTTAATGAATTGATGAAAGAGTTGGATTAAAGTTG
TATTAGTAATTAGAATTTGGTGTCAAATTTAATTTGACATTTGATCTTTTCCTATATATTGCCCCATAGA
GTCAGTTAACTCATTTTTATATTTCATAGATCAAATAAGAGAAATAACGGTATATTAATCCCTCCAAAA
AAAAAAAACGGTATATTTACTAAAAAATCTAAGCCACGTAGGAGGATAACAGGATCCCCGTAGGAGGA
TAACATCCAATCCAACCAATCACAACAATCCTGATGAGATAACCCACTTTAAGCCCACGCATCTGTGGC
ACATCTACATTATCTAAATCACACATTCTTCCACACATCTGAGCCACACAAAAACCAATCCACATCTTT
ATCACCCATTCTATAAAAAATCACACTTTGTGAGTCTACACTTTGATTCCCTTCAAACACATACAAAGA
GAAGAGACTAATTAATTAATTAATCATCTTGAGAGAAAATGGAGAAAATAGTGCTTCTTCTTGCAATA
GTCAGTCTTGTTAAAAGTGATCAGATTTGCATTGGTTACCATGCAAACAATTCAACAGAGCAGGTTGAC
ACAATCATGGAAAAGAACGTTACTGTTACACATGCCCAAGACATACTGGAAAAGACACACAACGGGAA
GCTCTGCGATCTAGATGGAGTGAAGCCTCTAATTTTAAGAGATTGTAGTGTAGCTGGATGGCTCCTCGG
GAACCCAATGTGTGACGAATTCATCAATGTACCGGAATGGTCTTACATAGTGGAGAAGGCCAATCCAA
CCAATGACCTCTGTTACCCAGGGAGTTTCAACGACTATGAAGAACTGAAACACCTATTGAGCAGAATA
AACCATTTTGAGAAAATTCAAATCATCCCCAAAAGTTCTTGGTCCGATCATGAAGCCTCATCAGGAGTT
AGCTCAGCATGTCCATACCTGGGAAGTCCCTCCTTTTTAGAAATGTGGTATGGCTTATCAAAAGAAC
AGTACATACCCAACAATAAAGAAAAGCTACAATAATACCAACCAAGAGGATCTTTTGGTACTGTGGGG
AATTCACCATCCTAATGATGCGGCAGAGCAGACAAGGCTATATCAAAACCCAACCACCTATATTTCCAT
TGGGACATCAACACTAAACCAGAGATTGGTACCAAAAATAGCTACTAGATCCAAAGTAAACGGGCAAA
GTGGAAGGATGGAGTTCTTCTGGACAATTTTAAAACCTAATGATGCAATCAACTTCGAGAGTAATGGA
AATTTCATTGCTCCAGAATATGCATACAAAATTGTCAAGAAGGGGACTCAGCAATTATGAAAAGTGA
ATTGGAATATGGTAACTGCAACACCAAGTGTCAAACTCCAATGGGGGCGATAAACTCTAGTATGCCAT
TCCACAACATACACCCTCTCACCATCGGGGAATGCCCCAAATATGTGAAATCAAACAGATTAGTCCTTG
CAACAGGGCTCAGAAATAGCCCTCAAAGAGAGAGCAGAAGAAAAAAGAGAGGACTATTTGGAGCTAT
AGCAGGTTTTATAGAGGGAGGATGGCAGGGAATGGTAGATGGTTGGTATGGGTACCACCATAGCAATG
AGCAGGGGAGTGGGTACGCTGCAGACAAAGAATCCACTCAAAAGGCAATAGATGGAGTCACCAATAA
GGTCAACTCAATCATTGACAAAATGAACACTCAGTTTGAGGCCGTTGGAAGGGAATTTAATAACTTAG
AAAGGAGAATAGAGAATTTAAACAAGAAGATGGAAGACGGGTTTCTAGATGTCTGGACTTATAATGCC
GAACTTCTGGTTCTCATGGAAAATGAGAGAACTCTAGACTTTCATGACTCAAATGTTAAGAACCTCTAC
GACAAGGTCCGACTACAGCTTAGGGATAATGCAAAGGAGCTGGGTAACGGTTGTTTCGAGTTCTATCA
CAAATGTGATAATGAATGTATGGAAAGTATAAGAAACGGAACGTACAACTATCCGCAGTATTCAGAAG
AAGCAAGATTAAAAAGAGAGGAAATAAGTGGGGTAAAATTGGAATCAATAGGAACTTACCAAATACT
GTCAATTTATTCAACAGTGGCGAGTTCCCTAGCACTGGCAATCATGATGGCTGGTCTATCTTTATGGAT
GTGCTCCAATGGATCGTTACAATGCAGAATTTGCATTTAAGAGCTCTAAGTTAAAATGCTTCTTCGTCT
CCTATTTATAATATGGTTTGTTATTGTTAATTTTGTTCTTGTAGAAGAGCTTAATTAATCGTTGTTGTTA
TGAAATACTATTTGTATGAGATGAACTGGTGTAATGTAATTCATTTACATAAGTGGAGTCAGAATCAG
AATGTTTCCTCCATAACTAACTAGACATGAAGACCTGCCGCGTACAATTGTCTTATATTTGAACAACTA
AAATTGAACATCTTTTGCCACAACTTTATAAGTGGTTAATATAGCTCAAATATATGGTCAAGTTCAATA
GATTAATAATGGAAATATCAGTTATCGAAATTCATTAACAATCAACTTAACGTTATTAACTACTAATTT
TATATCATCCCCTTTGATAAATGATAGTACA
```

METHOD OF PREPARING PLANT-DERIVED VLPS

CROSS REFERENCE TO RELATED APPLICATIONS

The present application is a National Phase Application of International Application No. PCT/CA2010/001488, filed Sep. 21, 2010, which claims the benefit of U.S. Patent Applications No. 61/244,786, filed Sep. 22, 2009, which applications are incorporated herein fully by this reference.

FIELD OF INVENTION

The present invention relates to methods of preparing plant-derived virus-like particles (VLPs).

BACKGROUND OF THE INVENTION

Current recombinant expression strategies in host cells such as E. coli, insect cell culture, and mammalian cell culture express and secrete proteins at very high level in the culture media. Using these systems high levels of expression, proper protein folding and post-translational modification of proteins, is achieved. Furthermore, purification of the expressed protein is simplified since intracellular proteins may be readily segregated from other components (DNA, vesicle, membranes, pigments, and so on). For plant or yeast expression systems, the cell wall prevents secretion of expressed protein into the culture media.

One of the primary methods to combat viral infections is by vaccination. Production of vaccines in response to an outbreak or epidemic, or to meet seasonal demands (e.g. the annual 'flu season' occurring in the fall, or the recent 'swine flu' outbreaks observed worldwide) requires the generation of sufficient quantity of vaccine given the short notice period. Current worldwide production of influenza vaccine may be insufficient in the face of a worldwide flu pandemic. Furthermore, dominant influenza strains change from year to year, thus stockpiling at low-need times in the year is not practical. Economical, large scale production of an effective influenza vaccine is of significant value.

Virus-like particles (VLPs) may be employed to prepare influenza vaccines. Suprastructures such as VLPs mimic the structure of the viral capsid, but lack a genome, and thus cannot replicate or provide a means for a secondary infection. VLPs offer an improved alternative to isolated (soluble) recombinant antigens for stimulating a strong immune response. VLPs are assembled upon expression of specific viral proteins and present an external surface resembling that of their cognate virus but, unlike true viral particle, do not incorporate genetic material. The presentation of antigens in a particulate and multivalent structure similar to that of the native virus achieves an enhanced stimulation of the immune response with balanced humoral and cellular components. Such improvement over the stimulation by isolated antigens is believed to be particularly true for enveloped viruses as enveloped VLPs present the surface antigens in their natural membrane-bound state (Grgacic and Anderson, 2006, Methods 40, 60-65). Furthermore, Influenza VLPs, with their nanoparticle organization, have been shown to be better vaccine candidates compared to recombinant hemagglutinin (HA) (i.e. monomeric HA, or HA organized in rosettes; assembly of 3-8 trimers of HA), and they are able to activate both humoral and cellular immune response. (Bright, R. A., et. al., 2007, Vaccine 25, 3871-3878).

The vast majority of the influenza vaccines currently on the market are composed of viral particle or virus antigens obtained from egg-grown virions. The production of egg-derived vaccines relies on the culture of live viruses in embryonated hen eggs. Split-influenza vaccines are obtained after chemical inactivation and disruption of purified virions with a detergent. Recombinant influenza antigens are an effective alternative to virus-derived antigens as pandemic vaccine products. Recombinant antigens can be produced from information on the genetic makeup of a new strain once this information is made available, and allows a rapid initiation of the production process. However, purified recombinant HA subunits appear less efficacious than inactivated split-influenza vaccines and higher antigen content is required to generate a potent immune response (Treanor et al., 2007, J. Am. Med. Assoc. 297, 1577-1582).

Influenza VLPs have been obtained in cultured mammalian cells from the co-expression of all 10 influenza proteins (Mena et al., 1996, J. Virol. 70, 5016-5024). Several viral proteins are dispensable for the production of VLPs, and influenza VLPs in vaccine development programs have been produced from the co-expression of the 2 major antigenic envelope proteins (HA and NA) with M1 or from the co-expression of HA and M1 only (Kang et al., 2009, Virus Res. 143, 140-146). Chen et al. (2007, J. Virol. 81, 7111-7123) have shown that HA alone is capable of driving VLP formation and budding and M1 co-expression could be omitted in their system. However, since HA was found to bind to sialylated glycoproteins on the surface of the mammalian cells producing the VLPs, a viral sialidase was co-expressed to allow the release of VLPs from the producing cell after budding.

A simpler VLP production system, for example, one that relies on the expression of only one or a few viral proteins without requiring expression of non-structural viral proteins is desirable to accelerate the development of vaccines. Production of viral antigens, including VLPs, in plant systems provides an advantage for production, in that they may be grown in a greenhouse or field, and don't require aseptic tissue culture methods and handling.

PCT Publication WO 2006/119516 (to Williamson and Rybicki) discloses expression of full length and truncated human-codon optimized H5 HA of Influenza A/Vietnam/1194/2004 in plants. The truncated construct lacks the membrane anchoring domain. The highest accumulation of HA protein was obtained with constructs that targeted to the ER. Constructs lacking a membrane targeting domain did not yield detectable HA. The production of VLPs was not reported.

The production of influenza HA VLPs that comprise a lipid envelope has been previously described by the inventors in WO 2009/009876 and WO 2009/076778 (to D'Aoust et al.; both of which are incorporated herein by reference). For enveloped viruses, it may be advantageous for a lipid layer or membrane to be retained by the virus. The composition of the lipid may vary with the system (e.g. a plant-produced enveloped virus would include plant lipids or phytosterols in the envelope), and may contribute to an improved immune response.

The assembly of enveloped VLPs in transgenic tobacco expressing the HBV surface antigen (HBsAg) was described by Mason et al. (1992, *Proc. Natl. Acad. Sci. USA* 89, 11745-11749). Plant-produced HBV VLPs were shown to induce potent B- and T-cell immune responses in mice when administered parenterally (Huang et al., 2005, *Vaccine* 23, 1851-1858) but oral immunization through feeding studies only induced a modest immune response (Smith et al., 2003, Vaccine 21, 4011-4021). Greco (2007, *Vaccine* 25, 8228-8240) showed that human immunodeficiency virus (HIV) epitopes in fusion with HBsAg accumulated as VLP when expressed in transgenic tobacco and *Arabidopsis*, creating a bivalent VLP vaccine.

Expression of the viral capsid protein (NVCP) in transgenic tobacco and potato plants resulted in the assembly of non-enveloped VLPs (Mason et al., 1996, *Proc. Natl. Acad. Sci. USA* 93, 5335-5340). NVCP VLPs have been produced in agroinfiltrated *N. benthamiana* leaves (Huang et al. 2009, *Biotechnol. Bioeng.* 103, 706-714) and their immunogenicity upon oral administration demonstrated in mice (Santi et al., 2008, *Vaccine* 26, 1846-1854). Administration of 2 or 3 doses of raw potatoes containing 215-751 μg of NVCP in the form of VLPs to healthy adult volunteers resulted in development of an immune response in and 95% of the immunized volunteers (Tacket et al. 2000, *J. Infect. Dis.* 182, 302-305). Non-enveloped VLPs have also been obtained from the expression of HBV core antigen (HBcAg; Huang et al., 2009, *Biotechnol. Bioeng.* 103, 706-714), and the human papillomavirus (HPV) major capsid protein L1 (Varsani et al., 2003, *Arch. Virol.* 148, 1771-1786).

It may be desirable to separate the VLPs from some, or all of the proteins, carbohydrates, etc. present in the plant or plant matter before the VLP is used in vaccine formulation. A method for extracting protein from the intercellular space of plants, comprising a vacuum and centrifugation process to provide an interstitial fluid extract comprising the protein of interest is described in PCT Publication WO 00/09725 (to Turpen et al.). This approach is suitable for small proteins (of 50 kDa or smaller) that pass through pores under vacuum and centrifugation, but is not suitable for larger superstructure proteins or protein complexes such as a VLP.

McCormick et al 1999 (Proc Natl Acad Sci USA 96:703-708) discloses use of a rice amylase signal peptide fused to a single-chain Fv (scFv) epitope to target the expressed protein to the extracellular compartment, followed by vacuum infiltration of leaf and stem tissue for recovery of the scFv polypeptides. Moehnke et al., 2008 (Biotechnol Lett 30:1259-1264) describes use of the vacuum infiltration method of McCormick to obtain a recombinant plant allergen from tobacco using an apoplastic extraction. PCT Publication WO 2003/025124 (to Zhang et al) discloses expression of scFv immunoglobulins in plants, targeting to the apoplastic space using murine signal sequences.

Given the complexity of VLPs and the plant tissue in which they may be produced, methods of preparing VLPs that are substantially free of, or easily separated from plant proteins, yet retain the structural and immunogenic characteristics of the enveloped virus are desired.

SUMMARY OF THE INVENTION

The present invention relates to methods of preparing plant-derived virus-like particles (VLPs). More specifically, the present invention is directed to methods of preparing VLPs comprising influenza antigens.

It is an object of the invention to provide an improved method of preparing plant-derived virus-like particles.

The present invention provides a method (A) of preparing plant derived VLPs comprising obtaining a plant or plant matter comprising plant-derived VLPs localized within the apoplast; producing a protoplast and an apoplast fraction, the apoplast fraction comprising plant-derived VLPs; and recovering the apoplast fraction. The method may further comprise a step of purifying the plant derived VLPs from the apoplast fraction. The plant-derived VLP may be a chimeric plant-derived VLP. The plant derived VLP may be selected from the group of viral envelope proteins, viral structural proteins, viral capsid proteins, and viral coat proteins. The plant derived VLPs may comprise influenza hemagglutinin.

The apoplast and protoplast fractions may be produced by treatment of the plant or plant matter by an enzyme composition. The enzyme composition may comprise one or more than one pectinase, one or more than one cellulase, or one or more than one pectinase and one or more than one cellulase. Furthermore, if desired, the enzyme composition does not include a lipase or protease, or the composition does not include an added lipase or protease.

Plant or plant matter may be obtained by growing, harvesting or growing and harvesting the plant. The plant matter may comprise some or all of the plant, one or more than one plant cell, leaves, stems, roots or cultured plant cells.

The present invention provides a method of preparing plant derived VLPs as described above (Method A), wherein a nucleic acid encoding the VLP selected from the group of viral envelope proteins, viral structural proteins, viral capsid proteins, and viral coat proteins is introduced into the plant in a transient manner. Alternatively, the nucleic acid is stably integrated within a genome of the plant.

The present invention provides a method of preparing plant derived VLPs as described above (Method A) further comprising a step of purifying the plant derived VLPs from the apoplast fraction. The step of purifying may comprise filtering the apoplast fraction using depth filtration to produce a clarified extract, followed by chromatography of the clarified extract using a cation exchange resin.

Without wishing to be bound by theory, proteins obtained from the apoplast are more homogenous, as the intermediate forms of post-translationally modified proteins, or proteins comprising other types of processing that occurs in various intracellular compartments are not co-extracted. A higher degree of homogeneity of a recombinant protein typically results in a higher quality of a preparation comprising the protein, and may result in a product with beneficial properties including higher potency, longer half-life, or better immunogenic capacity. For example, blood proteins containing high-mannose glycosylation are eliminated in blood circulation more rapidly than proteins comprising complex glycosylation. A glycosylated protein produce in the apoplastic fraction exhibits more complex-type glycosylation. Therefore, an apoplast-derived protein prepared using the methods described herein, involving cell-wall digestion, exhibit, for example, a better half life in circulation.

The present invention also provides for a method (B) of preparing plant-derived VLPs comprising a plant-derived lipid envelope, the method comprising, obtaining a plant, or plant matter comprising VLPs localized within the apoplast; treating the plant or plant matter with an enzyme composition to produce a protoplast fraction, and one or more than one apoplastic protein composition; separating the one or more than one apoplastic protein complex from the protoplast fraction, wherein the one or more than one apoplastic protein complexes comprise the VLPs. The enzyme composition may comprise one or more than one pectinase, one or more than one cellulase, or one or more than one pectinase and one or more than one cellulase. Furthermore, if desired, the enzyme composition does not include a lipase or protease, or the composition does not include an added lipase or protease. The plant-derived VLP may be a chimeric plant-derived VLP. The plant derived VLP may be selected from the group of viral envelope proteins, viral structural proteins, viral capsid proteins, and viral coat proteins. The plant derived VLPs may comprise influenza hemagglutinin.

The present invention provides a method of preparing plant derived VLPs as described above (Method B), wherein a nucleic acid encoding the VLP selected from the group of viral envelope proteins, viral structural proteins, viral capsid proteins, and viral coat proteins is introduced into the plant in a transient manner. Alternatively, the nucleic acid is stably integrated within a genome of the plant.

The present invention provides a method of preparing plant derived VLPs as described above (Method B) further comprising a step of purifying the plant derived VLPs from the apoplast fraction. The step of purifying may comprise filtering the apoplast fraction using depth filtration to produced a clarified extract, followed by chromatography of the clarified extract using a cation exchange resin.

The plant derived VLPs may include VLPs comprising one or more influenza HA polypeptides. The influenza HA polypeptide may also be a chimeric HA polypeptide. The plant-derived VLPs may further comprise hemagglutinating activity. Plant or plant matter may be obtained by growing, harvesting or growing and harvesting the plant. The plant matter may comprise some or all of the plant, or one or more than one plant cell, leaves, stems, roots or cultured cells.

The present invention also provides a method (C) of preparing plant derived VLPs, comprising obtaining a plant or plant matter comprising plant-derived VLPs, digesting the plant matter using a cell wall degrading enzyme composition to produced a digested fraction, and filtering the digested fraction to produced a filtered fraction and recovering the plant-derived VLPs from the filtered fraction.

The enzyme composition may comprise one or more than one pectinase, one or more than one cellulase, or one or more than one pectinase and one or more than one cellulase. Furthermore, if desired, the enzyme composition does not include a lipase or protease, or the composition does not include an added lipase or protease. The plant-derived VLP may be a chimeric plant-derived VLP. The plant derived VLP may be selected from the group of viral envelope proteins, viral structural proteins, viral capsid proteins, and viral coat proteins. The plant derived VLPs may comprise influenza hemagglutinin.

The present invention provides a method of preparing plant derived VLPs as described above (Method C), wherein a nucleic acid encoding the VLP selected from the group of viral envelope proteins, viral structural proteins, viral capsid proteins, and viral coat proteins is introduced into the plant in a transient manner. Alternatively, the nucleic acid is stably integrated within a genome of the plant.

The present invention provides a method of preparing plant derived VLPs as described above (Method C) further comprising a step of separating the VLPs in the filtered fraction from the cellular debris and insoluble materials. The step of separating may be performed by centrifugation, by depth filtration, or bother centrifugation and depth filtration to produce a clarified fraction. The plant derived VLPs may be further purified by chromatography, for example, the clarified extract may be purified using a cation exchange resin.

The plant derived VLPs may include VLPs comprising one or more influenza HA polypeptides. The influenza HA polypeptide may also be a chimeric HA polypeptide. The plant-derived VLPs may further comprise hemagglutinating activity. Plant or plant matter may be obtained by growing, harvesting or growing and harvesting the plant. The plant matter may comprise some or all of the plant, or one or more than one plant cell, leaves, stems, roots or cultured cells.

Without wishing to be bound by theory, plant-made VLPs comprising plant derived lipids, may induce a stronger immune reaction than VLPs made in other manufacturing systems and that the immune reaction induced by these plant-made VLPs is stronger when compared to the immune reaction induced by live or attenuated whole virus vaccines.

The composition of a protein extract obtained from a host cell is complex and typically comprises intercellular and intracellular components along with a protein or suprastructure of interest that is to be isolated. Preparation of an apoplastic fraction, followed by a step to segregate the intracellular proteins and components is advantageous since the protein or suprastructure of interest can be enriched and increase efficiency within a manufacturing process. Having a simpler process, comprising fewer efficient steps, may result in significant yield increases, and cost reduction. It has also been found that the process of digesting the cell wall using cell wall degrading enzymes increases VLP protein yield even if protoplasts do not remain intact during the extraction procedure. Without wishing to be bound by theory, the step of cell wall digestion may loosen the polymeric components of the cells wall and assist in release of the VLPs otherwise associated within the cell wall. This protocol may also minimize contamination of the VLPs within intracellular components.

Methods to digest plant cell-wall are known, and enzyme cocktail mixtures that digest cell walls may vary. The present invention is not limited by the cell wall digestion method used.

The methods described herein result in less disruption, and contamination of a plant-derived VLP extract when compared to methods for preparing plant-derived VLPs involving homogenization, blending or grinding. The methods described herein provide an apoplast fraction of the plant tissue and that may maintain the integrity of protoplasts and their components. The method as described herein is effective in purifying VLPs even if the protoplasts, or a portion of the protoplasts, lose their integrity and are no longer intact.

These methods provide a higher yield of VLPs when compared to methods of VLP extraction involving standard tissue disruption techniques, for example, homogenization, blending or grinding. The greater yield may be due to, in part, a reduction of the shearing forces that disrupt the structural integrity of the VLPs and/or the lipid envelope. Preparation of VLPs from an apoplastic fraction may be advantageous, as apoplastic fractions are significantly reduced, or free of, cytoplasmic proteins. Therefore, VLP separation from other proteins and matter, including HA monomers, trimers or fragments of HA, in the apoplastic fraction is easily carried out. However, increased yields of VLPs may also be obtained using the methods described herein, even if the protoplast preparation, or a portion of the protoplast preparation, is not intact.

The VLPs of the present invention are also characterized as exhibiting a greater hemagglutinating activity than those obtained using standard tissue disruption techniques. This improved hemagglutinating activity may result from a greater yield of intact VLPs (fewer HA monomers or trimers free in solution), a greater yield of intact VLPs with intact lipid envelopes, or a combination thereof.

Vaccines made using VLPs provide the advantage, when compared to vaccines made of whole viruses, that they are non-infectious. Therefore, biological containment is not an issue and it is not required for production. Plant-made VLPs provide a further advantage by allowing the expression system to be grown in a greenhouse or field, thus being significantly more economical and suitable for scale-up.

Additionally, plants do not comprise enzymes involved in synthesizing and adding sialic acid residues to proteins. VLPs may be produced in the absence of neuraminidase (NA), and there is no need to co-express NA, or to treat the producing cells or extract with sialidase (neuraminidase), to ensure VLP production in plants This summary of the invention does not necessarily describe all features of the invention.

BRIEF DESCRIPTION OF THE DRAWINGS

These and other features of the invention will become more apparent from the following description in which reference is made to the appended drawings wherein:

FIG. 1 shows a schematic representation of CPMVHT-based expression cassette (construct 685) for the expression of H5 A/Indonesia/5/05 hemagglutinin.

FIG. 2 shows sequences. FIG. 2A shows the nucleic acid sequence (SEQ ID NO. 1) of a portion of construct for expressing H5/Indo (construct number 685) from PacI (upstream of the 35S promoter) to AscI (immediately downstream of the NOS terminator). Coding sequence of H5 from A/Indonesia/5/2005 is underlined. FIG. 2B shows the amino acid sequence (SEQ ID NO. 2) of H5 A/Indonesia/5/05 hemagglutinin encoded by construct number 685.

FIG. 3 shows characterization of hemagglutinin (HA)-containing structures by size exclusion chromatography (SEC). Following centrifugation of the digested plant extract, the pellet was resuspended and fractionated by SEC. FIG. 3A shows the total soluble protein content per fraction (solid triangles; % of maximum, left-side Y-axis; determined using the Bradford method). The hemagglutinating activity of the collected fractions (solid bars; right-side Y axis) is also shown. FIG. 3B shows SDS-PAGE analysis of SEC eluted fractions. Fractions were precipitated by acetone and re-suspended in 1/40 volume of reducing sample loading buffer prior to analysis. Gel was stained with 0.1% Coomassie R-250 solution. Purified VLPs were run as a control. The band corresponding to the HA0 monomer is indicated by an arrow. MW—Molecular weight standards (kDa); C—Purified VLPs (control); lanes 7 through 10 and 14 through 16 correspond to fractions number eluted from SEC analysis, shown in FIG. 3A.

FIG. 4 shows a comparison of protein profiles obtained after enzymatic digestion and by mechanical homogenization using a Comitrol™ homogenizer. Samples were treated in denaturing sample loading buffer and proteins were separated by SDS-PAGE analysis of elution fractions. Gels were stained with 0.1% Coomassie R-250 solution. MW—Molecular weight standards (kDa); lane 1—25 0 enzyme mixture; lane 2—25 μl enzymatic digestion of plant tissue and lane 3—5 μl extract obtained with the Comitrol homogenizer.

FIG. 5 shows the nucleic acid sequence (SEQ ID NO: 9) of an HA expression cassette comprising alfalfa plastocyanin promoter and 5' UTR, hemagglutinin coding sequence of H5 from A/Indonesia/5/2005 (Construct #660), alfalfa plastocyanin 3' UTR and terminator sequences.

FIG. 6 shows the capture of HA-VLP on cationic exchange resin directly form separation of HA-VLP in the apoplastic fraction. Samples were treated in non-reducing, denaturing sample loading buffer and proteins were separated by SDS-PAGE. Gels were stained with 0.1% Coomassie R-250 solution. Lane 1: Apoplastic fraction after centrifugation, Lane 2-3: Apoplastic fraction after successive microfiltration; Lane 4: Load of the cationic exchange; Lane 5: Flow through fraction of the cationic exchange. Lane 6; elution from cationic exchange, concentrated 10×; Lane 7: Molecular weight standards (kDa).

FIG. 7 shows the Nanoparticle Tracking analysis (NTA) profile of H5/Indo VLP (A) and H1/Cal VLP (B) after clarification without addition of NaCl to digestion buffer and of H1/Cal VLP (C) with this addition. NTA experiments were carried out with NanoSight LM20 (NanoSight, Amesbury, UK). The instrument is equipped with a blue laser (405 nm), a sample chamber and a Viton fluoroelastomer o-ring. Videos were recorded at room temperature and analysed using the NTA 2.0 software. The samples were recorded for 60 sec. The shutter and gain were manually chosen so that optimal particle resolution was obtained.

FIG. 8 shows a Western blot of extract of H3/Brisbane VLP generated by enzymatic digestion using different buffers. Lane 1) Pure recombinant HA standard (5 μg, from Immune Technology Corp. IT-003-0042p) Lane 2 to 5 contain 7 μl of centrifuged enzymatic extract performed in the following buffers: Lane 2) 600 mM Mannitol+125 mM citrate+75 mM $NaPO_4$+25 mM EDTA+0.04% bisulfite pH6.2, Lane 3) 600 mM Mannitol+125 mM citrate+75 mM $NaPO_4$+50 mM EDTA+0.04% bisulfite pH6.2, Lane 4) 200 mM Mannitol+125 mM citrate+75 mM $NaPO_4$+25 mM EDTA+0.03% bisulfite pH6.2, Lane 5) 200 mM Mannitol+125 mM citrate+75 mM $NaPO_4$+50 mM EDTA+0.03% bisulfite pH6.2. The arrow represents the immunodetection signal of HA0.

DETAILED DESCRIPTION

The present invention relates to methods of preparing plant-derived virus-like particles (VLPs). More specifically, the present invention is directed to methods of preparing VLPs comprising influenza hemagglutinin (HA).

The following description is of a preferred embodiment.

The present invention provides a method for obtaining a protein, or protein suprastructure of interest. The protein of interest may be present in the apoplast or extracellular compartment, corresponding to the plant cell portion excluding the protoplast/spheroplast compartment. The method involves removing, digesting or both digesting and removing the cellulosic plant cell wall that surrounds plant cells. By digesting the cell wall the polymeric components of the cell wall are loosened, and the protein or protein suprastructure of interest may be more readily released. By using this method, the protein or protein suprastructure of interest is enriched since the protoplast/spheroplast compartment that contains a majorly host-cell proteins and components is segregated from the apoplast. As noted below, the method as provided herein is still effective in obtaining a protein or protein suprastructure of interest if, during the process, the integrity of the protoplast/spheroplast compartment is lost, if the protoplast/spheroplast compartment is not intact, and if a portion of host cell proteins and components from the protoplast/spheroplast compartment are present in the apoplast fraction.

Examples of protein suprastructures are structures comprised of two or more polypeptides; the polypeptides may be the same, or different; if different, they may be present in a ratio of about 1:1 to about 10:1 or greater. The protein suprastructure may further comprise one or more lipids, phospholipids, nucleic acids, membranes or the like. The two or more polypeptides may be connected by a covalent bond, a disulfide bridge, charge interaction, hydrophobic attraction, van der waals forces, hydrogen bonds or the like.

An example of a protein suprastructure is a virus like particle (VLP), which may be enveloped, or non-enveloped, for example, a viral envelope protein, a viral structural protein, a viral capsid protein, or a viral coat protein.

The present invention also provides a method of preparing plant-derived virus like particles (VLPs). The method involves obtaining a plant or plant matter comprising plant-derived VLPs localized within the apoplast; producing a protoplast/spheroplast fraction, and an apoplast fraction from the plant matter, the apoplast fraction comprising plant-derived VLPs, and recovering the apoplast fraction. If desired, the plant derived VLPs may be purified from the apoplast fraction.

The present invention also provides a method of preparing VLPs comprising a plant-derived lipid envelope. The method includes obtaining a plant, or plant matter comprising VLPs, treating the plant or plant matter with an enzyme composition to produce one or more than one apoplastic protein complex and a protoplast/spheroplast fraction, and separating the one or more than one apoplastic protein complex from the protoplast fraction. The one or more than one apoplastic protein complex comprises the VLPs comprising a plant derived lipid envelope.

The present invention also provides a method of preparing plant derived VLPs, comprising obtaining a plant or plant matter that comprise the plant-derived VLPs, digesting the plant matter using a cell wall degrading enzyme composition to produced a digested fraction, and filtering the digested fraction to produced a filtered fraction and recovering the plant-derived VLPs from the filtered fraction. In this method, integrity of the protoplasts may not be required.

A protoplast is a plant cell that has had its cell wall completely or partially removed. A spheroplast may have partial removal of the cell wall. A protoplast, a spheroplast, or both a protoplast and spheroplast (protoplast/spheroplast) may be used as described herein, and the terms as used herein are interchangeable. The cell wall may be disrupted and removed mechanically (e.g. via homogenization, blending), the cell wall may be fully or partially digested enzymatically, or the cell wall may be removed using a combination of mechanical and enzymatic methods, for example homogenization followed by treatment with enzymes for digestion of the cell wall. Protoplasts may also be obtained from cultured plant cells, for example liquid cultured plant cells, or solid cultured plant cells.

Standard reference works setting forth the general principles of plant tissue culture, cultured plant cells, and production of protoplasts, spheroplasts and the like include: *Introduction to Plant Tissue Culture*, by M K Razdan 2$^{nd}$ Ed. (Science Publishers, 2003; which is incorporated herein by reference), or see for example, the following URL: molecular-plant-biotechnology.info/plant-tissue-culture/protoplast-isolation.htm. Methods and techniques relating to protoplast (or spheroplast) production and manipulation are reviewed in, for example, Davey M R et al., 2005 (Biotechnology Advances 23:131-171; which is incorporated herein by reference). Standard reference works setting forth the general methods and principles of protein biochemistry, molecular biology and the like include, for example Ausubel et al, Current Protocols In Molecular Biology, John Wiley & Sons, New York (1998 and Supplements to 2001; which is incorporated herein by reference); Sambrook et al, Molecular Cloning: A Laboratory Manual, 2d Ed., Cold Spring Harbor Laboratory Press, Plainview, N.Y., 1989 (which is incorporated herein by reference); Kaufman et al, Eds., Handbook Of Molecular And Cellular Methods In Biology And Medicine, CRC Press, Boca Raton, 1995 (which is incorporated herein by reference); McPherson, Ed., Directed Mutagenesis: A Practical Approach, IRL Press, Oxford, 1991 (which is incorporated herein by reference).

Enzymes useful for digesting or degrading plant cell walls for release or protoplasts or spheroplasts are known to one of skill in the art and may include cellulase (EC 3.2.1.4), pectinase (EC 3.2.1.15), xylanase (EC 3.2.1.8), chitinases (EC 3.2.1.14), hemicellulase, or a combination thereof. Non-limiting examples of suitable enzymes includes a multi-component enzyme mixture comprising cellulase, hemicellulase, and pectinase, for example MACEROZYME™ (containing approximately: Cellulase: 0.1 U/mg, Hemicellulase: 0.25 U/mg, and Pectinase: 0.5 U/mg). Other examples of commercial enzymes, enzyme mixtures and suppliers are listed in Table 1 (see: *Introduction to Plant Tissue Culture*, by MK Razdan 2$^{nd}$ Ed., Science Publishers, 2003).

Alternate names, and types of cellulases include endo-1,4-β-D-glucanase; β-1,4-glucanase; β-1,4-endoglucan hydrolase; cellulase A; cellulosin AP; endoglucanase D; alkali cellulase; cellulase A 3; celludextrinase; 9.5 cellulase; avicelase; pancellase SS and 1,4-(1,3;1,4)-β-D-glucan 4-glucanohydrolase. Alternate names, and types of pectinases (polygalacturonases) include pectin depolymerase; pectinase; endopolygalacturonase; pectolase; pectin hydrolase; pectin polygalacturonase; endo-polygalacturonase; poly-α-1,4-galacturonide glycanohydrolase; endogalacturonase; endo-D-galacturonase and poly(1,4-α-D-galacturonide) glycanohydrolase. Alternate names, and types of xylanases include hemicellulase, endo-(1→4)-β-xylan 4-xylanohydrolase; endo-1,4-xylanase; xylanase; β-1,4-xylanase; endo-1,4-xylanase; endo-β-1,4-xylanase; endo-1,4-β-D-xylanase; 1,4-O-xylan xylanohydrolase; β-xylanase; β-1,4-xylan xylanohydrolase; endo-1,4-β-xylanase; β-D-xylanase. Alternate names, and types of chitinases include chitodextrinase; 1,4-β-poly-N-acetylglucosaminidase; poly-β-glucosaminidase; β-1,4-poly-N-acetyl glucosamidinase; poly[1,4-(N-acetyl-β-D-glucosaminide)]glycanohydrolase.

TABLE 1

Non-limiting examples of commercially available enzymes for protoplast isolation

| Enzyme | Source | Supplier |
|---|---|---|
| Cellulases | | |
| Cellulase ONOZUKA R-10 | *Trichoderma viride* | Kinki Yakult Mfg. Col. Ltd. 8-12, Shinglkancho Nishinomiya, Japan |
| Cellulase ONOZUKA RS | *T. viride* | Yakult Honsha Co., Tokyo, Japan |
| Cellulase YC | *T. viride* | Seishin Pharma Co. Ltd. 9-500-1, Nagareyama Nagareyama-shi, Chiba-kan, Japan |

TABLE 1-continued

Non-limiting examples of commercially available enzymes for protoplast isolation

| Enzyme | Source | Supplier |
|---|---|---|
| Cellulase CEL | T. viride | Cooper Biomedical Inc. Malvern, PA, USA |
| Cellulysin | T. viride | Calbiochem, San Diego, CA, USA |
| Driselase | Irpex locteus | Kyowa Hakko Kogyo Co. Ltd., Tokyo, Japan |
| Melcelase P-1 | T. viride | Meiji Seiki Kaisha Ltd. No. 8, 2-Chome Kyobashi, Chou-Ku, Japan |
| Multifect CX GC | T. viride | Genencor |
| Multifect CX B | T. viride | Genencor |
| Hemicellulases | | |
| Hellcase | Helix pomatia | Industrie Biologique Francaise, Gennevilliers, France |
| Hemicellulase | Aspergillus niger | Sigma Chemical Co., St. Louis, MO, USA |
| Hemicellulase H-2125 | Rhizopus sp. | Sigma, Munchen |
| Rhozyme HP 150 | Aspergillus niger | Genencor Inc., South San Francisco, CA, USA |
| Pectinases | | |
| MACERASE | Rhizopus arrhizus | Calbiochem, San Diego, CA, USA |
| MACEROZYME R-10 | R. arrhizus | Yakult Honsha Co., Tokyo, Japan |
| Multifect Pectinase FE | A. niger | Genencor |
| PATE | Baccilus polymyza | Farbwerke-Hoechst AG, Frankfurt, FRG |
| Pectinol | Aspergillus sp. | Rohm and Haas Co. Independence Hall West, Philadelphia, PA 19105, USA |
| Pectolyase Y-23 | Aspergillus joponicus | Seishin Pharma Co. Ltd., Japan |
| Zymolyase | Arthrobacter luteus | Sigma Chemical Co., USA |

Choice of a particular enzyme or combination of enzymes, and concentration and reaction conditions may depend on the type of plant tissue used from which the protoplast and apoplast fraction comprising the VLPs is obtained. A mixture of cellulase, hemicellulase and pectinase, for example, a pectinase MACEROZYME™ or Multifect, may be used in a concentration ranging from 0.01% to 2.5% (v/v), for example 0.01, 0.02, 0.04, 0.06, 0.08, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, or 2.5% (v/v), or any amount therebetween. MACEROZYME™ or Multifect may be used alone, or in combination with other enzymes, e.g cellulase, pectinase, hemicellulase, or a combination thereof. Cellulase may be used in a concentration ranging from 0.1% to 5%, for example 0.1, 0.25, 0.5, 0.75, 1.0, 1.25, 1.5, 1.75, 2.0, 2.25, 2.5, 2.75, 3.0, 3.25, 3.5, 3.75, 4.0, 4.25, 4.5, 4.75, 5.0% (w/v) or any amount therebetween.

The enzyme solution (alternately referred to as a cell wall degrading composition, digesting solution) will generally comprise a buffer or buffer system, an osmoticum, and one or more than one salts, divalent cations or other additives. The buffer or buffer system is selected to maintain a pH in the range suitable for enzyme activity and the stability of the protein(s), or VLP, to purify, for example, within the range of about pH 5.0 to about 8.0, or any value therebetween. The selected pH used may vary depending upon the VLP to be recovered, for example the pH may be 5.0, 5.2, 5.4, 5.6, 5.8, 6.0, 6.2, 6.4, 6.6, 6.8, 7.0, 7.2, 7.4, 7.6, 7.8, 8.0, or any pH therebetween. Examples of buffers or buffer systems include, but are not limited to, MES, phosphate, citrate and the like. One or more buffers or buffer systems may be combined in an enzyme solution (digesting solution); the one or more buffers may be present at a concentration from 0 mM to about 200 mM, or any amount therebetween, for example 10, 20, 30, 40, 50, 60, 70, 80, 90, 100, 110, 120, 130, 140, 150, 160, 170, 180 or 190 mM or any amount therebetween.

Depending on the suitability, an osmoticum component can be added if desired. The osmoticum and its concentration are selected to raise the osmotic strength of the enzyme solution. Examples of osmoticum include mannitol, sorbitol or other sugar alcohols, polyethylene glycol (PEG) of varying polymer lengths, and the like. Concentration ranges of osmoticum may vary depending on the plant species, the type of osmoticum used, and the type of plant tissue selected (species or organ of origin e.g. leaf or stem)—generally the range is from 0M to about 0.8 M, for example 0.05, 0.1, 0.15, 0.2, 0.25, 0.3, 0.35, 0.4, 0.5, 0.6, 0.7, or 0.75 M, or any amount therebetween, for example, 0, 50, 100, 150, 200, 250, 300, 350, 400, 450, 500, 550, 600 nM mannitol, or any amount therebetween. The concentration of osmoticum may also be expressed as a percentage (w/v). For some plant or tissue types, it may be beneficial to employ a slightly hypertonic preparation, which may facilitate separation of plant cell plasma membrane from the cell wall. The osmoticum can also be omitted during digestion.

Another parameter to set for the plant digestion is the temperature. Temperature may be controlled if desired during the digestion process. Useful temperature range should be between 4° C. and 40° C. or any temperature therebetween, for example from about 4° C. to about 15° C., or any amount therebetween, or from about 4° C. to about 22° C., or any temperature therebetween. Depending to the temperature chosen, the other digestion experimental parameters may be adjusted to maintain optimal extraction conditions.

Cations, salts or both may be added to improve plasma membrane stability, for example divalent cations, such as $Ca^{2+}$, or $Mg^{2+}$, at 0.5-50 mM, or any amount therebetween, salts, for example $CaCl_2$, NaCl, $CuSO_4$, $KNO_3$, and the like, from about 0 to about 750 mM, or any amount therebetween, for example 10, 20, 30, 40, 50, 100, 200, 300, 400, 500, 600, 700 or 750 mM. Other additives may also be added including a chelator for example, but not limited to, EDTA, EGTA, from about 0 to about 200 mM, or any amount therebetween, for example 5, 10, 15, 20, 25, 50, 75, 100, 125, 150, 175, 200 mM, or any amount therebetween, a reducing agent to prevent oxidation such as, but not limited to, sodium bisulfite or ascorbic acid, at 0.005-0.4% or any amount therebetween, for example 0.01, 0.02, 0.03, 0.04, 0.05, 0.06, 0.07, 0.08, 0.09, 0.1, 0.15, 0.2, 0.25, 0.3, 0.35, 0.4%, or any amount therebetween, specific enzyme inhibitors (see below), and if desired, an inhibitor of foliar senescence, for example, cycloheximide, kinetin, or one or more polyamines.

The digestion solution may also comprise one or more of mannitol from about 0 to about 600 mM, NaCl from about 0 to about 500 mM, EDTA from about 0 to about 50 mM, cellulase from about 1% to about 2% v/v, pectinase from about 0 to about 1% v/v, sodium metabisulfite from about 0.03 to about 0.04%, citrate from about 0 to about 125 mM or $NaPO_4$ from about 0 to 75 mM.

The plant matter may be treated to enhance access of the enzymes or enzyme composition to the plant cell wall. For example, the epidermis of the leaf may be removed or 'peeled' before treatment with an enzyme composition. The plant matter may be cut into small pieces (manually, or with a shredding or cutting device such as an Urschel slicer); the cut up plant matter may be further infiltrated with an enzyme composition under a partial vacuum (Nishimura and Beevers 1978, Plant Physiol 62:40-43; Newell et al., 1998, J. Exp Botany 49:817-827). Mechanical perturbation of the plant matter may also be applied to the plant tissues (Giridhar et al., 1989. Protoplasma 151:151-157) before or during treatment with an enzyme composition. Furthermore, cultured plant cells, either liquid or solid cultures, may be used to prepare protoplasts or spheroplasts.

It may be desired to use an enzyme composition that lacks, or that has inactivated lipases or proteases. In some embodiments, one or more protease, or lipase inhibitors may be included in the enzyme composition. Examples of lipase inhibitors include RHC80267 (SigmaAldrich); examples of protease inhibitors include E-64, $Na_2EDTA$, Pepstatin, aprotinin, PMSF, Pefabloc, Leupeptin, bestatin and the like.

Any suitable method of mixing or agitating the plant matter in the enzyme composition may be used. For example, the plant matter may be gently swirled or shaken in a tray or pan or via a rotary shaker, tumbled in a rotating or oscillating drum. Precaution should be taken in order to minimize the protoplast (and/or spheroplast) damage until they are removed form the digestion soup. The digestion vessel should be selected accordingly.

As a non-limiting example, an enzyme composition comprising 1.5% cellulase (Onozuka R-10) and 0.375% MACEROZYME™ in 500 mM mannitol, 10 m $CaCl_2$ and 5 mM MES (pH 5.6) may be used for protoplast (or spheroplast) production from some *Nicotiana* tissues. As described herein, the concentration of mannitol may also be varied from about 0 to about 500 mM, or any amount therebetween. One of skill in the art, provided with the information disclosed herein, will be able to determine a suitable enzyme composition for the age and strain of the *Nicotiana* sp, or for another species used for production of VLPs.

Upon disruption of the cell wall, or partial digestion of the cell wall, a protoplast fraction (comprising protoplasts and/or spheroplasts), and an "apoplast fraction" are obtained. Alternatively, a "digested fraction" may be obtained. As noted below, integrity of the protoplast fraction may not be required to produce high yields of protein as described herein, therefore, an apoplast fraction or a digested fraction may be used for the extraction of proteins, for example, but not limited to, VLPs, viral envelope proteins, viral structural proteins, viral capsid proteins, viral coat proteins.

By "apoplast fraction" it is meant a fraction that is obtained following enzymatic digestion, or partial enzymatic digestion, using cell wall degrading enzymes of the plant matter in the presence of an osmoticum and/or other ingredients that may be used to assist in maintaining integrity of the protoplast. The apoplast fraction may comprise some components arising from disrupted protoplasts (or spheroplasts). For example, the apoplast fraction may comprise from about 0 to about 50% (v/v) or any amount therebetween, of the components from the protoplast fraction, or 0, 0.1, 0.5, 1, 5, 10, 15, 20, 25, 30, 35, 40, 45, or 50% (v/v) or any amount therebetween of the components from the protoplast fraction.

By a "digested fraction" it is meant the fraction that remains following enzymatic digestion, or partial enzymatic digestion, using cell wall degrading enzymes of the plant matter, however, integrity of the protoplast is not required, and the digested fraction may comprise intact, disrupted, or both intact and disrupted protoplasts. The composition comprising the cell wall degrading enzymes used to produce the digested fraction may comprise an osmoticum, or the osmoticum may be present at a reduced amount when compared to the amount present in standard procedures used to obtain protoplasts, or the osmoticum may be absent from the composition. The digested fraction comprises the apoplast fraction and the protoplast/spheroplast fraction, however, the protoplast/spheroplast fraction may or may not be intact. The digested fraction contains intracellular components and extracellular components. Intracellular components may be found in the form of protoplasts/spheroplasts if an osmoticum is used to maintain the protoplast/spheroplast intact. If no osmoticum is used in the digestion solution, then the protoplasts/spheroplasts may be disrupted and the intracellular and extracellular components may be combined in the digested fraction. As described herein, the VLPs, may be separated from components of the digested fraction using any suitable technique. Without wishing to be bound by theory, the step of cell wall digestion may loosen the polymeric components of the cells wall and assist in release VLPs, otherwise trapped within the cell wall. This protocol also minimizes contamination of the VLPs, with the intracellular components. The VLPs may be separated from cellular debris following enzymatic digestion using low speed centrifugation followed by filtration, depth filtration, sedimentation, precipitation for example, but not limited to ammonium sulfate precipitation, or a combination thereof to obtain a separated fraction comprising the proteins or suprastructure proteins of interest.

If an osmoticum is used, the protoplast/spheroplast fraction, or fraction comprising protoplasts, may be separated from the apoplast fraction using any suitable technique, for example but not limited to, centrifugation, filtration, depth filtration, sedimentation, precipitation, or a combination thereof to obtain a separated fraction comprising the VLPs and/or comprising protoplasts/spheroplasts that comprise the VLPs.

The protoplast (and spheroplast) fraction, or fraction comprising protoplasts, may be separated from the apoplast fraction using any suitable technique, for example but not limited to, centrifugation, filtration, depth filtration, sedimentation, precipitation, or a combination thereof to obtain a separated fraction.

The separated fraction may be for example a supernatant (if centrifuged, sedimented, or precipitated), or a filtrate (if filtered), and is enriched for VLPs. The separated fraction may be further processed to isolate, purify, concentrate or a combination thereof, the VLPs by, for example, additional centrifugation steps, precipitation, chromatographic steps (e.g. size exclusion, ion exchange chromatography), tangential flow filtration, or a combination thereof. The presence of purified VLPs may be confirmed by, for example, native or SDS-PAGE, Western analysis using an appropriate detection antibody, capillary electrophoresis, or any other method as would be evident to one of skill in the art.

The apoplast is the portion of the plant cell outside the plasma membrane, and includes the cell wall and intercellular spaces of the plant. While it is preferred that the integrity of the protoplasts (and/or spheroplasts) be maintained during digestion and further processing, it is not required that the protoplasts remain intact in order to enrich for VLPs.

During synthesis, VLPs are excreted outside of the plasma membrane. VLPs are of an average size of about 20 nm to 1 μm, or any amount therebetween, for example 60, 65, 70, 75, 80, 85, 90, 95, 100, 105, 110, 120, 130, 140, 150, 160, 170, 180, 190, or 200 nm, or any amount therebetween, for example 100 nm, and may include a lipid membrane. Due to their size, once synthesized, VLPs may remain trapped between the plasma membrane and cell wall and may be inaccessible for isolation or further purification using standard mechanical methods used to obtain plant proteins. In order to maximize yields, minimize contamination of the VLP fraction with cellular proteins, maintain the integrity of the VLPs and, in some embodiments, the associated lipid envelope or membrane, methods of disrupting the cell wall to release the VLPs that minimize mechanical damage to the protoplast (and/or spheroplasts) may be useful, such as the enzymatic methods described herein. However, it is not required that the integrity of all of the protoplasts be retained during the procedure.

A VLP produced in a plant according to some aspects of the invention may be complexed with plant-derived lipids. The VLP may comprise an HA0 precursor form, or the HA1 or HA2 domains retained together by disulphide bridges form. The plant-derived lipids may be in the form of a lipid bilayer, and may further comprise an envelope surrounding the VLP. The plant derived lipids may comprise lipid components of the plasma membrane of the plant where the VLP is produced, including, but not limited to, phosphatidylcholine (PC), phosphatidylethanolamine (PE), glycosphingolipids, phytosterols or a combination thereof. A plant-derived lipid may alternately be referred to as a 'plant lipid'. Examples of phytosterols are known in the art, and include, for example, stigmasterol, sitosterol, 24-methylcholesterol and cholesterol (Mongrand et al., 2004, J. Biol Chem 279:36277-86).

Correct folding of viral structural proteins such as HA, and formation of trimers of HA is desired for assembly of VLPs. VLPs, and in particular VLPs comprising a plant derived lipid envelope, may provide for a superior immune response when administered to a subject, relative to administration of the structural protein monomer.

In some embodiments, polypeptide expression may be targeted to any intracellular or extracellular space, organelle or tissue of a plant. In order to localize the expressed polypeptide to a particular location, the nucleic acid encoding the polypeptide may be linked to a nucleic acid sequence encoding a signal peptide. A signal peptide may alternately be referred to as a transit peptide or signal sequence. Signal peptides or peptide sequences for directing localization of an expressed polypeptide to the apoplast include, but are not limited to, a rice amylase signal peptide (McCormick 1999, Proc Natl Acad Sci USA 96:703-708), protein disulfide isomerase signal peptide (PDI) having the amino acid sequence:

```
MAKNVAIFGLLFSLLLLVPSQIFAEE;,    SEQ ID NO. 10
``` plant pathogenesis related protein (PRP; Szyperski et al. PNAS 95:2262-2262), for example, Tobacco plant pathogenesis related protein 2 (PRP), human monoclonal antibody signal peptide (SP), or any native hemagglutinin signal peptide.

In some examples, an expressed polypeptide may accumulate in specific intercellular or extracellular space (such as the apoplast), organelle or tissue, for example when the polypeptide is expressed and secreted in the absence of a signal peptide or transit peptide.

The term "virus like particle" (VLP), or "virus-like particles" or "VLPs" refers to structures that self-assemble and comprise viral surface proteins, for example an influenza HA protein, or a chimeric influenza HA protein. VLPs and chimeric VLPs are generally morphologically and antigenically similar to virions produced in an infection, but lack genetic information sufficient to replicate and thus are non-infectious. VLPs and chimeric VLPs may be produced in suitable host cells including plant host cells, and if desired further purified.

While influenza VLPs and chimeric influenza VLPs are exemplified herein, the methods described herein may be used for any plant-derived VLPs that localize in, or are secreted to, the apoplast.

By "chimeric protein" or "chimeric polypeptide", it is meant a protein or polypeptide that comprises amino acid sequences from two or more than two sources, for example but not limited to, two or more influenza types or subtypes, that are fused as a single polypeptide. The chimeric protein or polypeptide may include a signal peptide that is the same (i.e. native) as, or heterologous with, the remainder of the polypeptide or protein. The chimeric protein or chimeric polypeptide may be produced as a transcript from a chimeric nucleotide sequence, and remain intact, or if required, the chimeric protein or chimeric polypeptide may be cleaved following synthesis. The intact chimeric protein, or cleaved portions of the chimeric protein, may associate to form a multimeric protein. A chimeric protein or a chimeric polypeptide may also include a protein or polypeptide comprising subunits that are associated via disulphide bridges (i.e. a multimeric protein). For example, a chimeric polypeptide comprising amino acid sequences from two or more than two sources may be processed into subunits, and the subunits associated via disulphide bridges to produce a chimeric protein or chimeric polypeptide.

The polypeptide may be influenza hemagglutinin (HA), and each of the two or more than two amino acid sequences that make up the polypeptide may be obtained from different HA's to produce a chimeric HA, or chimeric influenza HA. A chimeric HA may also include a amino acid sequence comprising heterologous signal peptide (a chimeric HA pre-protein) that is cleaved after synthesis. Examples of HA proteins that may be used in the invention described herein may be found in WO 2009/009876; WO 2009/076778; WO 2010/003225 (which are incorporated herein by reference). A nucleic acid encoding a chimeric polypeptide may be described as a "chimeric nucleic acid", or a "chimeric nucleotide sequence". A virus-like particle comprised of chimeric HA may be described as a "chimeric VLP". Chimeric VLPs are further described in PCT Application No. PCT/CA2010/000983 filed Jun. 25, 2010, and U.S. Provisional Application No. 61/220,161 (filed Jun. 24, 2009; which is incorporated herein by reference). VLPs can be obtained from expression of native or chimeric HA.

The HA of the VLPs prepared according to a method provided by the present invention, include known sequences and variant HA sequences that may be developed or identified. Furthermore, VLPs produced as described herein do not comprise neuraminidase (NA) or other components for example M1 (M protein), M2, NS and the like. However, NA and M1 may be co-expressed with HA should VLPs comprising HA and NA be desired.

Generally, the term "lipid" refers to a fat-soluble (lipophilic), naturally-occurring molecules. A chimeric VLP produced in a plant according to some aspects of the invention may be complexed with plant-derived lipids. The plant-derived lipids may be in the form of a lipid bilayer, and may further comprise an envelope surrounding the VLP. The plant derived lipids may comprise lipid components of the plasma membrane of the plant where the VLP is produced, including phospholipids, tri-, di- and monoglycerides, as well as fat-soluble sterol or metabolites comprising sterols. Examples include phosphatidylcholine (PC), phosphatidylethanolamine (PE), phosphatidylinositol, phosphatidylserine, glycosphingolipids, phytosterols or a combination thereof. A plant-derived lipid may alternately be referred to as a 'plant lipid'. Examples of phytosterols include campesterol, stigmasterol, ergosterol, brassicasterol, delta-7-stigmasterol, delta-7-avenasterol, daunosterol, sitosterol, 24-methylcholesterol, cholesterol or beta-sitosterol (Mongrand et al., 2004, J. Biol Chem 279:36277-86). As one of skill in the art will readily understand, the lipid composition of the plasma membrane of a cell may vary with the culture or growth conditions of the cell or organism, or species, from which the cell is obtained.

Cell membranes generally comprise lipid bilayers, as well as proteins for various functions. Localized concentrations of particular lipids may be found in the lipid bilayer, referred to as 'lipid rafts'. These lipid raft microdomains may be enriched in sphingolipids and sterols. Without wishing to be bound by theory, lipid rafts may have significant roles in endo and exocytosis, entry or egress of viruses or other infectious agents, inter-cell signal transduction, interaction with other structural components of the cell or organism, such as intracellular and extracellular matrices.

VLPs comprising a lipid envelope has been previously described in WO 2009/009876; WO 2009/076778, and WO 2010/003225 (which are incorporated herein by reference). With reference to influenza virus, the term "hemagglutinin" or "HA" as used herein refers to a structural glycoprotein of influenza viral particles. The HA of the present invention may be obtained from any subtype. For example, the HA may be of subtype H1, H2, H3, H4, H5, H6, H7, H8, H9, H10, H11, H12, H13, H14, H15, or H16, or of influenza types B or C. The recombinant HA of the present invention may also comprise an amino acid sequence based on the sequence of any hemagglutinin. The structure of influenza hemagglutinin is well-studied and demonstrates a high degree of conservation in secondary, tertiary and quaternary structure. This structural conservation is observed even though the amino acid sequence may vary (see, for example, Skehel and Wiley, 2000 Ann Rev Biochem 69:531-69; Vaccaro et al 2005; which is incorporated herein by reference). Nucleotide sequences encoding HA are well known, and are available for example, from the BioDefense and Public Health Database (now Influenza Research Database; Squires et al., 2008 Nucleic Acids Research 36:D497-D503) for example at URL: biohealthbase.org/GSearch/home.do?decorator=Influenza) or the databases maintained by the National Center for Biotechnology Information (NCBI; for example at URL: ncbi.nlm.nih.gov/sites/entrez?db=nuccore&cmd=search&term=influenza), both of which are incorporated herein by reference.

The present invention also pertains to methods of preparing, isolating, or both preparing and isolating VLPs, including influenza VLPs of viruses which infect humans, or host animals, for example primates, horses, pigs, birds, sheep, avian water fowl, migratory birds, quail, duck, geese, poultry, chicken, camel, canine, dogs, feline, cats, tiger, leopard, civet, mink, stone marten, ferrets, house pets, livestock, mice, rats, seal, whale and the like. Some influenza viruses may infect more than one host animal.

Amino acid variation is tolerated in hemagglutinins of influenza viruses. This variation provides for new strains that are continually being identified. Infectivity between the new strains may vary. However, formation of hemagglutinin trimers, which subsequently form VLPs is maintained. The present invention also includes methods of preparing any plant-derived VLPs, regardless of the HA subtype or sequence, or chimeric HA comprising the VLP, or species of origin.

Correct folding of the hemagglutinins may be important for stability of the protein, formation of multimers, formation of VLPs and function of the HA (ability to hemagglutinate), among other characteristics of influenza hemagglutinins. Folding of a protein may be influenced by one or more factors, including, but not limited to, the sequence of the protein, the relative abundance of the protein, the degree of intracellular crowding, the availability of cofactors that may bind or be transiently associated with the folded, partially folded or unfolded protein, the presence of one or more chaperone proteins, or the like.

Heat shock proteins (Hsp) or stress proteins are examples of chaperone proteins, which may participate in various cellular processes including protein synthesis, intracellular trafficking, prevention of misfolding, prevention of protein aggregation, assembly and disassembly of protein complexes, protein folding, and protein disaggregation. Examples of such chaperone proteins include, but are not limited to, Hsp60, Hsp65, Hsp 70, Hsp90, Hsp100, Hsp20-30, Hsp10, Hsp100-200, Hsp100, Hsp90, Lon, TF55, FKBPs, cyclophilins, ClpP, GrpE, ubiquitin, calnexin, and protein disulfide isomerases (see, for example, Macario, A. J. L., Cold Spring Harbor Laboratory Res. 25:59-70. 1995; Parsell, D. A. & Lindquist, S. Ann. Rev. Genet. 27:437-496 (1993); U.S. Pat. No. 5,232,833). Chaperone proteins, for example but not limited to Hsp40 and Hsp70 may be used to ensure folding of a chimeric HA (PCT Application No. PCT/CA2010/000983 filed Jun. 25, 2010, and U.S. Provisional Application No. 61/220,161, filed Jun. 24, 2009; WO 2009/009876 and WO 2009/076778, all of which are incorporated herein by reference). Protein disulfide isomerase (PDI; Accession No. Z11499) may also be used.

Once recovered, VLPs may be assessed for structure, size potency or activity by, for example, hemagglutination assay, electron microscopy, light scattering, size exclusion chromatography, HPLC, Western blot analysis, or electrophoresis. These and other methods for assessing size, concentration, activity and composition of VLPs are known in the art.

For preparative size exclusion chromatography, a preparation comprising VLPs may be obtained by the methods described herein, and insoluble material removed by centrifugation. Precipitation with PEG may also be of benefit. The recovered protein may be quantified using conventional methods (for example, Bradford Assay, BCA), and the extract passed through a size exclusion column, using for example SEPHACRYL™, SEPHADEX™, or similar medium, and the fractions collected. Blue Dextran 2000 or a suitable protein, may be used as a calibration standard. The extract may also be passed through a cation exchange column and active fractions collected. Following chromatography, fractions may be further analyzed by protein electrophoresis, immunoblot, or both, to confirm the presence of VLPs and the protein complement of the fraction.

A hemagglutination assay may be used to assess the hemagglutinating activity of the VLP-containing fractions, using methods well-known in the art. Without wishing to be bound by theory, the capacity of HA to bind to RBC from different animals is driven by the affinity of HA for sialic acids α2,3 or α2,3 and the presence of these sialic acids on the surface of RBC. Equine and avian HA from influenza viruses agglutinate erythrocytes from all several species, including turkeys, chickens, ducks, guinea pigs, humans, sheep, horses and cows; whereas human HAs will bind to erythrocytes of turkey, chickens, ducks, guinea pigs, humans and sheep (Ito T. et al, 1997, Virology, 227:493-499; Medeiros R et al, 2001. Virology 289:74-85).

A hemagglutination inhibition (HI, or HAI) assay may also be used to demonstrate the efficacy of antibodies induced by a vaccine, or vaccine composition comprising chimeric HA or chimeric VLP can inhibit the agglutination of red blood cells (RBC) by recombinant HA. Hemagglutination inhibitory antibody titers of serum samples may be evaluated by microtiter HAI (Aymard et al 1973). Erythrocytes from any of several species may be used—e.g. horse, turkey, chicken or the like. This assay gives indirect information on assembly of the HA trimer on the surface of VLP, confirming the proper presentation of antigenic sites on HAs.

Cross-reactivity HAI titres may also be used to demonstrate the efficacy of an immune response to other strains of virus related to the vaccine subtype. For example, serum from a subject immunized with a vaccine composition comprising a chimeric hemagglutinin comprising an HDC of a first influenza type or subtype may be used in an HAI assay with a second strain of whole virus or virus particles, and the HAI titer determined.

Methods for transformation, and regeneration of transgenic plants, plant cells, plant matter or seeds comprising VLPs are established in the art and known to one of skill in the art. The method of obtaining transformed and regenerated plants is not critical to the present invention.

By "transformation" it is meant the interspecific transfer of genetic information (nucleotide sequence) that is manifested genotypically, phenotypically or both. The interspecific transfer of genetic information from a chimeric construct to a host may be heritable (i.e. integrated within the genome of the host) and the transfer of genetic information considered stable, or the transfer may be transient and the transfer of genetic information is not inheritable.

By the term "plant matter", it is meant any material derived from a plant. Plant matter may comprise an entire plant, tissue, cells, or any fraction thereof. Further, plant matter may comprise intracellular plant components, extracellular plant components, liquid or solid extracts of plants, or a combination thereof. Further, plant matter may comprise plants, plant cells, tissue, a liquid extract, or a combination thereof, from plant leaves, stems, fruit, roots or a combination thereof. Plant matter may comprise a plant or portion thereof which has not been subjected to any processing steps. A portion of a plant may comprise plant matter. Plants or plant matter may be harvested or obtained by any method, for example, the whole plant may be used, or the leaves or other tissues specifically removed for use in the described methods. Transgenic plants expressing and secreting VLPs may also be used as a starting material for processing as described herein.

The constructs of the present invention can be introduced into plant cells using Ti plasmids, Ri plasmids, plant virus vectors, direct DNA transformation, micro-injection, electroporation, infiltration, and the like. For reviews of such techniques see for example Weissbach and Weissbach, *Methods for Plant Molecular Biology*, Academy Press, New York VIII, pp. 421-463 (1988); Geierson and Corey, *Plant Molecular Biology*, 2d Ed. (1988); and Miki and Iyer, Fundamentals of Gene Transfer in Plants. In *Plant Metabolism*, 2d Ed. D T. Dennis, D H Turpin, D D Lefebrve, D B Layzell (eds), Addison-Wesley, Langmans Ltd. London, pp. 561-579 (1997). Other methods include direct DNA uptake, the use of liposomes, electroporation, for example using protoplasts, micro-injection, microprojectiles or whiskers, and vacuum infiltration. See, for example, Bilang, et al. (Gene 100: 247-250 (1991), Scheid et al. (Mol. Gen. Genet. 228: 104-112, 1991), Guerche et al. (Plant Science 52: 111-116, 1987), Neuhause et al. (Theor. Appl Genet. 75: 30-36, 1987), Klein et al., Nature 327: 70-73 (1987); Howell et al. (Science 208: 1265, 1980), Horsch et al. (Science 227: 1229-1231, 1985), DeBlock et al., Plant Physiology 91: 694-701, 1989), Methods for Plant Molecular Biology (Weissbach and Weissbach, eds., Academic Press Inc., 1988), Methods in Plant Molecular Biology (Schuler and Zielinski, eds., Academic Press Inc., 1989), Liu and Lomonossoff (J. Virol Meth, 105:343-348, 2002), U.S. Pat. Nos. 4,945,050; 5,036,006; 5,100,792; 6,403,865; 5,625, 136, (all of which are hereby incorporated by reference).

Transient expression methods may be used to express the constructs of the present invention (see Liu and Lomonossoff, 2002, Journal of Virological Methods, 105:343-348; which is incorporated herein by reference). Alternatively, a vacuum-based transient expression method, as described in PCT Publications WO 00/063400, WO 00/037663 (incorporated herein by reference) may be used. These methods may include, for example, but are not limited to, a method of Agro-inoculation or Agro-infiltration, however, other transient methods may also be used as noted above. With either Agro-inoculation or Agro-infiltration, a mixture of *Agrobacteria* comprising the desired nucleic acid enter the intercellular spaces of a tissue, for example the leaves, aerial portion of the plant (including stem, leaves and flower), other portion of the plant (stem, root, flower), or the whole plant. After crossing the epidermis the *Agrobacterium* infect and transfer t-DNA copies into the cells. The t-DNA is episomally transcribed and the mRNA translated, leading to the production of the protein of interest in infected cells, however, the passage of t-DNA inside the nucleus is transient.

The influenza VLPs prepared by methods of the present invention may be used in conjunction with an existing influenza vaccine, to supplement the vaccine, render it more efficacious, or to reduce the administration dosages necessary. As would be known to a person of skill in the art, the vaccine may be directed against one or more than one influenza virus. Examples of suitable vaccines include, but are not limited to, those commercially available from Sanofi-Pasteur, ID Biomedical, Merial, Sinovac, Chiron, Roche, MedImmune, GlaxoSmithKline, Novartis, Sanofi-Aventis, Serono, Shire Pharmaceuticals and the like.

If desired, the VLPs of the present invention may be admixed with a suitable adjuvant as would be known to one of skill in the art. Furthermore, the VLP may be used in a vaccine composition comprising an effective dose of the VLP for the treatment of a target organism, as defined above. Furthermore, the VLP produced according to the present invention may be co-expressed with other protein components or reconstituted with other VLPs or influenza protein components, for example, neuraminidase (NA), M1, and M2. It can also be co-expressed or reconstituted with other VLP made of vaccinal proteins such as malaria antigens, HIV antigens, respiratory syncytial virus (RSV) antigens, and the like.

The sequences described herein are summarized below.

| SEQ ID NO: | Description | Figure |
|---|---|---|
| 1 | Nucleic acid sequence (construct 685) | 2A |
| 2 | Amino acid sequence encoded by SEQ ID NO: 1 | 2B |
| 3 | pBinPlus.2613c: AGGAAGGGAAGAAAGCGAAAGGAG | |
| 4 | Mut-ATG115.r: GTGCCGAAGCACGATCTGACAACGT TGAAGATCGCTCACGCAAGAAAGACAAGAGA | |
| 5 | Mut-ATG161.c: GTTGTCAGATCGTGCTTCGGCACCAGTACAA CGTTTTCTTTCACTGAAGCGA | |
| 6 | LC-05-1.110r: TCTCCTGGAGTCACAGACAGGGTGG | |
| 7 | ApaI-H5 (A-Indo).1c: TGTCGGGCCCATGGAGAAAATAGTGC TTCTTCTTGCAAT | |
| 8 | H5 (A-Indo)-StuI.1707r: AAATAGGCCTTTAAATGCAAATTC TGCATTGTAACGA | |
| 9 | nucleic acid sequence (construct 660) | 5 |
| 10 | PDI signal peptide: MAKNVAIFGLLFSLLLLVPSQIFAEE | |
| 11 | Plasto-443c | |
| 12 | supP19-plasto.r | |
| 13 | supP19-1c | |
| 14 | SupP19-SacI.r | |

The present invention will be further illustrated in the following examples. However it is to be understood that these examples are for illustrative purposes only, and should not be used to limit the scope of the present invention in any manner.

Assembly of Expression Cassettes

Constructs that may be used for the production of VLPs are described U.S. Provisional Application No. 61/220,161 (filed Jun. 24, 2009), WO 2009/009876, WO 2009/076778 and WO2010/003225 all of which are incorporated herein by reference. Constructs may also include those listed in Table 2. Assembly of these constructs is described in WO 2009/009876, WO 2009/076778, WO2010/003225 and U.S. 61/220,161. However other constructs comprising known HA's, including but not limited to, those provided in Table 2, and combined with similar or different regulatory elements and promoters, may also be used for the production of VLPs as described herein.

TABLE 2

Non-limiting examples of constructs that can be used for hemagglutinin production.

| Cassette number | Corresponding HA | HA abbreviation |
|---|---|---|
| 540 | SpPDI-H1 from strain A/New Caledonia/20/99 (H1N1) | H1/NC |
| 560 | SpPDI-H1 A/California/4/2009 in 2X35S/CPMV-HT expression cassette | H1/Cal WT |
| 580 | SpPDI-H1 A/New Caledonia/20/99 in 2x35S/CPMV-HT expression cassette | H1/NC |
| 660 | H5 from strain A/Indonesia/5/2005 (H5N1) | H1/Indo |
| 663 | H5 A/Indonesia/5/2005 | H1/Indo |
| 685 | H5 A/Indonesia/5/2005 in CPMV-HT expression cassette | H1/Indo |
| 686 | SpPDI-H5 A/Indonesia/5/2005 in CPMV-HT expression cassette | H1/Indo |
| 690 | H1 A/Brisbane/59/07 receptor-binding (RB) domain in H5 A/Indonesia/5/05 backbone | H1/Bris |
| 691 | H1 A/Brisbane/59/07 esterase and receptor-binding domains (E1-RB-E2) in H5 A/Indonesia/5/05 backbone | H1/Bris |
| 696 | H5 A/Indonesia/5/05 receptor-binding (RB) domain in H1 A/New Caledonia/20/99 backbone | H1/Indo |
| 732 | H1 A/Brisbane/59/2007 in CPMV-HT expression cassette | H1/Bris |
| 733 | SpPDI-H1 A/Brisbane/59/2007 in CPMV-HT expression cassette | H1/Bris |

TABLE 2-continued

Non-limiting examples of constructs that can be used for hemagglutinin production.

| Cassette number | Corresponding HA | HA abbreviation |
| --- | --- | --- |
| 734 | H1 A/Brisbane/59/07 receptor-binding (RB) domain in H5 A/Indonesia/5/05 backbone in CPMV-HT expression cassette | H1/Bris |
| 735 | H3 A/Brisbane/10/2007 in CPMV-HT expression cassette | H3/Bris |
| 736 | SpPDI-H3 A/Brisbane/10/2007 in CPMV-HT expression cassette | H3/Bris |
| 737 | Assembly of chimeric SpPDI-H3 A/Brisbane/10/2007 (ectodomain) + H5 A/Indonesia/5/2005 (TmD + Cyto tail) in CPMV-HT expression cassette | H3/Bris-H5/Indo chimera |
| 738 | HA B/Florida/4/2006 in CPMV-HT expression cassette | B/Flo |
| 739 | SpPDI-HA B/Florida/4/2006 in CPMV-HT expression cassette | B/Flo |
| 745 | SpPDI-HA B/Florida/4/2006 (ectodomain) + H5 A/Indonesia/5/2005 (TmD + Cyto tail) in CPMV-HT expression cassette | B/Flo |
| 747 | SpPDI-HA B/Florida/4/2006+ H5 A/Indonesia/5/2005 (TmD + Cyto tail) in 2X35S-CPMV-HT expression cassette | B/Flo |
| 774 | HA of A/Brisbane/59/2007 (H1N1) | H1/Bris |
| 775 | HA of A/Solomon Islands 3/2006 (H1N1) | H1/Solomon |
| 776 | HA of A/Brisbane 10/2007 (H3N2) | H3/Bris |
| 777 | HA of A/Wisconsin/67/2005 (H3N2) | H3/Wisc |
| 778 | HA of B/Malaysia/2506/2004 | B/Malaysia |
| 779 | HA of B/Florida/4/2006 | B/Flo |
| 780 | HA of A/Singapore/1/57 (H2N2) | H2/Sing |
| 781 | HA of A/Anhui/1/2005 (H5N1) | H5/Anhui |
| 782 | HA of A/Vietnam/1194/2004 (H5N1) | H5/Vietnam |
| 783 | HA of A/Teal/HongKong/W312/97 (H6N1) | H6/HongKong |
| 784 | HA of A/Equine/Prague/56 (H7N7) | H7/Prague |
| 785 | HA of A/HongKong/1073/99 (H9N2) | H9/HongKong |
| 787 | H1 A/Brisbane/59/2007 | H1/Bris |
| 790 | H3 A/Brisbane/10/2007 | H3/Bris |
| 798 | HA B/Florida/4/2006 | B/Flo |

CPMV-HT expression cassettes included the 35S promoter to control the expression of an mRNA comprising a coding sequence of interest flanked, in 5' by nucleotides 1-512 from the Cowpea mosaic virus (CPMV) RNA2 with mutated ATG at positions 115 and 161 and in 3', by nucleotides 3330-3481 from the CPMV RNA2 (corresponding to the 3' UTR) followed by the NOS terminator. Plasmid pBD-C5-1LC, (Sainsbury et al. 2008; Plant Biotechnology Journal 6: 82-92 and PCT Publication WO 2007/135480), was used for the assembly of CPMV-HT-based hemagglutinin expression cassettes. The mutation of ATGs at position 115 and 161 of the CPMV RNA2 was done using a PCR-based ligation method presented in Darveau et al. (Methods in Neuroscience 26: 77-85 (1995)). Two separate PCRs were performed using pBD-C5-1LC as template. The primers for the first amplification were pBinPlus.2613c (SEQ ID NO: 3) and Mut-ATG115.r (SEQ ID NO: 4). The primers for the second amplification were Mut-ATG161.c (SEQ ID NO: 5) and LC-C5-1.110r (SEQ ID NO: 6). The two fragments were then mixed and used as template for a third amplification using pBinPlus.2613c (SEQ ID NO: 3) and LC-C5-1.110r (SEQ ID NO: 6) as primers. The resulting fragment was digested with PacI and ApaI and cloned into pBD-C5-1LC digested with the same enzyme. The expression cassette generated was named 828.

Assembly of H5 A/Indonesia/5/2005 in CPMV-HT Expression Cassette (Construct Number 685).

The assembly of this cassette is described in WO 2009/009876, WO 2009/076778 and WO2010/003325, which are incorporated herein by reference.

Briefly, the coding sequence of H5 from A/Indonesia/5/2005 was cloned into CPMV-HT as follows: restriction sites ApaI (immediately upstream of the initial ATG) and StuI (immediately downstream of a stop codon) were added to the hemagglutinin coding sequence by performing a PCR amplification with primers ApaI-H5 (A-Indo).1c (SEQ ID NO: 7) and H5 (A-Indo)-StuI.1707r (SEQ ID NO: 8) using construct number 660 (D'Aoust et al., Plant Biotechnology Journal 6:930-940 (2008)) as template. Construct 660 comprises an alfalfa plastocyanin promoter and 5' UTR, hemagglutinin coding sequence of H5 from A/Indonesia/5/2005 (Construct #660), alfalfa plastocyanin 3' UTR and terminator sequences (SEQ ID NO: 9; FIG. 5). The resulting fragment was digested with ApaI and StuI restriction enzymes and cloned into construct number 828, previously digested with the same enzymes. The resulting cassette was named construct number 685 (FIG. 1, 2).

Suppressors of Silencing.

Post-transcriptional gene silencing (PTGS) may be involved in limiting expression of transgenes in plants, and co-expression of a suppressor of silencing from the potato virus Y (HcPro) may be used to counteract the specific degradation of transgene mRNAs (Brigneti et al., 1998). Alternate suppressors of silencing are well known in the art and may be used as described herein (Chiba et al., 2006, Virology 346:7-14; which is incorporated herein by reference), for example but not limited to, TEV-p1/HC-Pro (Tobacco etch virus-p1/HC-Pro), BYV-p21, p19 of Tomato bushy stunt virus (TBSV p19), capsid protein of Tomato crinkle virus (TCV-CP), 2b of Cucumber mosaic virus; CMV-2b), p25 of Potato virus X (PVX-p25), p11 of Potato virus M (PVM-p11), p11 of Potato virus S (PVS-p11), p16 of Blueberry scorch virus, (BScV-p16), p23 of Citrus tristeza virus (CTV-p23), p24 of Grapevine leafroll-associated virus-2, (GLRaV-2 p24), p10 of Grapevine virus A, (GVA-p10), p14 of Grapevine virus B (GVB-p14), p10 of Heracleum latent virus (HLV-p10), or p16 of Garlic common latent virus (GCLV-p16). Therefore, a suppressor of silencing, for example, but not limited to, HcPro, TEV-p1/HC-Pro, BYV-p21, TBSV p19, TCV-CP, CMV-2b, PVX-p25, PVM-p11, PVS-p11, BScV-p16, CTV-p23, GLRaV-2 p24, GBV-p14, HLV-p10, GCLV-p16 or GVA-p10, may be co-expressed along with the nucleic acid sequence encoding the protein of interest to further ensure high levels of protein production within a plant.

The construction of p19 is described in described in WO 2010/0003225 (which is incorporated herein by reference). Briefly, the coding sequence of p19 protein of tomato bushy stunt virus (TBSV) was linked to the alfalfa plastocyanin expression cassette by the PCR-based ligation method presented in Darveau et al. (Methods in Neuroscience 26: 77-85 (1995)). In a first round of PCR, a segment of the plastocyanin promoter was amplified using primers Plasto-443c:

```
GTATTAGTAATTAGAATTTGGTGTC    (SEQ ID NO: 11)
``` and supP19-plasto.r

```
                           (SEQ ID NO: 12)
CCTTGTATAGCTCGTTCCATTTTCTCTCAAGATG
``` with construct 660 (described in WO 2010/0003225, which is incorporated herein by reference) as template. In parallel, another fragment containing the coding sequence of p19 was amplified with primers supP19-1c

```
ATGGAACGAGCTATACAAGG    (SEQ ID NO: 13)
``` and SupP19-SacI.r

```
AGTCGAGCTCTTACTCGCTTTCTTTTTCGAAG (SEQ ID NO: 14)
``` using construct 35S:p19 as described in Voinnet et al. (The Plant Journal 33: 949-956 (2003)) as template. Amplification products were then mixed and used as template for a second round of amplification (assembling reaction) with primers Plasto-443c and SupP19-SacI.r. The resulting fragment was digested with BamHI (in the plastocyanin promoter) and Sad (at the end of the p19 coding sequence) and cloned into construct number 660, previously digested with the same restriction enzymes to give construct number R472. The plasmids were used to transform *Agrobacteium tumefaciens* (AGL1; ATCC, Manassas, Va. 20108, USA) by electroporation (Mattanovich et al., 1989). The integrity of all *A. tumefaciens* strains were confirmed by restriction mapping. The *A. tumefaciens* strain comprising R472 is termed "AGL1/R472".

HcPro construct (35HcPro) was prepared as described in Hamilton et al. (2002). All clones were sequenced to confirm the integrity of the constructs. The plasmids were used to transform *Agrobacteium tumefaciens* (AGL1; ATCC, Manassas, Va. 20108, USA) by electroporation (Mattanovich et al., 1989). The integrity of all *A. tumefaciens* strains were confirmed by restriction mapping.

Preparation of Plant Biomass, Inoculum, Agroinfiltration, and Harvesting

*Nicotiana benthamiana* plants were grown from seeds in flats filled with a commercial peat moss substrate. The plants were allowed to grow in the greenhouse under a 16/8 photoperiod and a temperature regime of 25° C. day/20° C. night. Three weeks after seeding, individual plantlets were picked out, transplanted in pots and left to grow in the greenhouse for three additional weeks under the same environmental conditions. After six weeks, plants have an average weight of 80 g and 30 cm in height.

*Agrobacterium* strain AGL1 was transfected (electroporation) with constructs as identified below, using the methods described by D'Aoust et al 2008 (Plant Biotechnology Journal 6:930-940). Transfected *Agrobacterium* were grown in YEB medium supplemented with 10 mM 2-(N-morpholino)ethanesulfonic acid (MES), 20 µM acetosyringone, 50 µg/ml kanamycin and 25 µg/ml of carbenicillin pH5.6 to an $OD_{600}$ between 0.6 and 1.6. *Agrobacterium* suspensions were centrifuged before use and resuspended in infiltration medium (10 mM $MgCl_2$ and 10 mM MES pH 5.6).

Plants were agroinfiltrated as described in D'Aoust et al (supra). Briefly, for vacuum-infiltration, *A. tumefaciens* suspensions were centrifuged, resuspended in the infiltration medium and stored overnight at 4° C. On the day of infiltration, culture batches were diluted in 2.5 culture volumes and allowed to warm before use. Whole plants of *N. benthamiana* were placed upside down in the bacterial suspension in an air-tight stainless steel tank under a vacuum of 20-40 Torr for 2-min. Unless otherwise specified, all infiltrations were performed as co-infiltration with a bacterial transformed with R472 (strain AGL1/R472) at a 1:1 ratio. Following vacuum infiltration, plants were returned to the greenhouse for a 4-6 day incubation period until harvest.

Leaf Sampling and Total Protein Extraction (Mechanical Homogenization)

Following incubation of 4, 5, 6, 7 and 8 days, the aerial part of plants was harvested and used immediately. Total soluble proteins were extracted by homogenizing plant tissue in 3 volumes of cold 50 mM Tris pH 8.0, 0.15 M NaCl containing 1% Triton X-100 and 0.004% sodium metabisulfite. Plant tissue were mechanically homogenized using a POLYTRON™, grinding with mortar and pestle, or with a COMITROL™ in 1 volume of cold 50 mM Tris pH 8, 0.15 M NaCl. The buffer used with the COMITROL™ also contained 0.04% sodium metabisulfite. Following homogenization, the slurry of ground plant material was centrifuged at 5,000 g for 5 min at 4° C. and the crude extracts (supernatant) kept for analysis. The total protein content of clarified crude extracts was determined by the Bradford assay (Bio-Rad, Hercules, CA) using bovine serum albumin as the reference standard.

VLP Extraction by Cell Wall Digestion

Leaf tissue was collected from the *Nicotiana benthamiana* plants and cut into ~1 $cm^2$ pieces. The leaf pieces were soaked in 500 mM mannitol for 30 minutes at room temperature (RT). The mannitol solution was then removed and changed with the enzyme mix (mixture of cellulases from *Trichoderma viride* (Onozuka R-10; 3% v/v) and a mixture of pectinases from *Rhizopus* sp. (MACEROZYME™; 0.75% v/v; both from Yakult Pharmaceuticals) in protoplasting solution (500 mM mannitol, 10 mM $CaCl_2$ and 5 mM MES/KOH (pH 5.6)). The ratio used was 20 g of leaf pieces per 100 mL solution. This preparation was spread evenly into a shallow vessel (~11×18 cm) and incubated for 16 hours on a rotary shaker at 40 rpm and 26° C.

Alternately, VLP extraction may be performed as follows: plants were agroinfiltrated with AGL1/#685 as described in example 1. Leaf tissue was collected from the N benthamiana plants at day 6 post-infiltration and cut into ~1 $cm^2$ pieces. Multifect Pectinase FE, Multifect CX CG and Multifect CX B (Genencor) were added to 1.0% each (v/v) in a 600 mM Mannitol, 75 mM Citrate, 0.04% sodium bisulfite pH 6.0 buffer using a ratio of 1:2.5 (w/v) fresh biomass;

digestion buffer. The biomass was digested for 15 h at room temperature in a orbital shaker.

Following incubation, leaf debris was removed by filtration (nylon filter of 250 or 400 μm mesh). Protoplasts in suspension were collected by centrifugation at 200×g (15 min), followed by centrifugation of the supernatant at 5000×g (15 min) to further clarify the supernatant. Alternately, a single centrifugation step at 5000×g for 15 minutes may be employed. Seventy mL of the supernatant was then centrifuged at 70,000×g for 30 minutes. The resulting pellet was resuspended in 1.7 mL of PBS and analyzed immediately or frozen.

Protein Analysis

A hemagglutination assay for H5 was based on a method described by Nayak and Reichl (2004). Briefly, serial double dilutions of the test samples (100 μL) were made in V-bottomed 96-well microtiter plates containing 100 μL PBS, leaving 100 μL of diluted sample per well. One hundred microliters of a 0.25% turkey red blood cells suspension (Bio Link Inc., Syracuse, NY) were added to each well, and plates were incubated for 2 h at room temperature. The reciprocal of the highest dilution showing complete hemagglutination was recorded as hemagglutination activity. In parallel, a recombinant HAS standard (A/Vietnam/1203/2004 H5N1) (Protein Science Corporation, Meriden, CT) was diluted in PBS and run as a control on each plate.

ELISA

HAS standard was prepared with purified virus-like particles which were disrupted by treatment with 1% Triton X-100 followed by mechanical agitation in a Tissue Lyser™ (Qiagen) for 1 min. U-bottom 96-well microtiter plates were coated with 10 μg/mL of capture antibody (Immune Technology Corporation, #IT-003-0051) in 50 mM carbonate-bicarbonate coating buffer (pH 9.6) for 16-18 hours at 4° C. All washes were performed with 0.01 M PBS (phosphate-buffered saline), pH 7.4 containing 0.1% Tween-20. After incubation, plates were washed three times and blocked with 1% casein in PBS for 1 hour at 37° C. After the blocking step, plates were washed three times. The HAS standard was diluted in a mock extract (prepared from leaf tissue infiltrated with AGL1/R472 alone) to generate a standard curve from 500 to 50 ng/mL. Samples to quantify were treated in 1% Triton X-100 prior to loading the microplate. Plates were further incubated for 1 hour at 37° C. After washing, sheep polyclonal antibody raised against HAS (CBER/FDA) diluted 1:1000 was added and the plates were incubated for 1 hour at 37° C. After washing, horseradish peroxidase-conjugated rabbit anti-sheep antibody diluted 1:1000 was added and the plates were incubated for 1 hour at 37° C. After the final washes, the plates were incubated with SureBlue TMB peroxidase substrate (KPL) for 20 minutes at room temperature. Reaction was stopped by the addition of 1N HCl and $A_{450}$ values were measured using a Multiskan Ascent plate reader (Thermo Scientific).

Example 1

Enzymatic Extraction of Plant Tissue Releases High Quantities of HA Having an Elevated Relative Activity The quantity and relative activity of HA obtained from the present enzymatic extraction method were compared with that of HA obtained from common mechanical extraction methods. *N. benthamiana* plants were infiltrated with AGL1/685 and the leaves were harvested after a five to six-day incubation period. Leaf homogenates were prepared as follows: Two grams of leaves were homogenized with a Polytron homogenizer; 4 g of leaves were ground with a mortar and a pestle; and 25 kg of leaves were homogenized with a COMITROL™ processor (Urschel Laboratories) in an extraction buffer (50 mM Tris, 150 mM NaCl pH 8.0, ratio of 1:1 w/v). Enzymatic extraction was carried as follow: Twenty grams of harvested leaves were subjected to digestion with Macerozyme pectinases and Onozuka R-10 cellulases as described above. Following digestion, leaf debris were removed by filtration (nylon filter, 250 μm mesh). Protoplasts in suspension were removed by centrifugation at 200×g (15 min), and the supernatant further clarified by centrifugation at 5000×g (15 min).

The quantity and relative activity of HA in each of these plant extracts is shown in Table 3. The quantity of HA obtained from the enzymatic extraction method is significantly greater than that obtained from the mechanical methods.

TABLE 3

Comparative quantities and relative activities of HA obtained from mechanical and enzymatic extraction of plant leaves.

| Extraction method | Relative activity | Quantity* |
|---|---|---|
| Comitrol ™ extract | 100% | 100% |
| Polytron extract | 50% | 150% |
| Mortar extract | 100% | 220% |
| Digestion extract | 440% | 570% |

*Quantity was evaluated by ELISA analysis

All data have been adjusted to take into account the differences in volume of liquid added for each extraction method.

The Comitrol ™ extraction method was chosen as the standard value for the purpose of the present comparative analysis.

Example 2

Enzymatic Digestion of Plant Tissue Releases HA Organized into VLPs

A combination of differential centrifugation and size exclusion chromatography (SEC) was used to demonstrate that the HA obtained by the enzymatic extraction method described herein were organized as VLPs. *N. benthamiana* plants were agroinfiltrated with AGL1/685 as described in Example 1. Leaves were collected from the plants 6 days post-infiltration, cut into ~1 $cm^2$ pieces and then digested, coarse-filtered and centrifuged as described in Example 1.

The clarified samples were then centrifuged at 70,000×g to allow for segregation of VLPs. The centrifugation pellet, containing the VLPs, was gently resuspended in 1/50 volume of Phosphate buffered saline (PBS; 0.1M sodium phosphate, 0.15M NaCl pH 7.2) before being loaded on a SEC column.

SEC columns of 32 ml SEPHACRYL™ S-500 high resolution beads (S-500 HR: GE Healthcare, Uppsala, Sweden, Cat. No. 17-0613-10) were prepared with equilibration/elution buffer (50 mM Tris, 150 mM NaCl, pH8). SEC chromatography was performed with the loading of a 1.5 mL VLP sample onto the equilibrated column, and its elution with 45 mL of equilibration/elution buffer. The eluate was collected in fractions of 1.7 mL, and the protein content of each fraction was evaluated by mixing 10 μL of the eluate fraction with 200 μL of diluted Bio-Rad protein dye reagent (Bio-Rad, Hercules, Calif.). Each separation was preceded by a calibration with Blue Dextran 2000 (GE Healthcare Bio-Science Corp., Piscataway, NJ, USA). Comparison of the elution profiles of both Blue Dextran 2000 and host proteins was performed for each separation to ensure uniformity of the separations.

Protein Analysis of the SEC Eluted Fractions Total protein content of clarified crude extracts was determined by the Bradford assay (Bio-Rad, Hercules, CA) using bovine serum albumin as the reference standard. Proteins present in SEC eluate fractions were precipitated with acetone (Bollag et al., 1996), resuspended in either 0.25 volume or 0.05 volume of denaturing sample loading buffer (0.1M Tris pH 6.8, 0.05% bromophenol blue, 12.5% glycerol, 4% SDS and 5% beta-mercaptoethanol) for SDS-PAGE analysis or immunoblot analysis, respectively. Separation by SDS-PAGE was performed under reducing conditions, and Coomassie Brillant Blue R-250 was used for protein staining.

Hemagglutination assay for H5 was performed based on a method described by Nayak and Reichl (2004). Briefly, successive double dilutions of the test samples (100 µL) were made in V-bottomed 96-well microtiter plates containing 100 µL PBS, leaving 100 µL of diluted sample per well. One hundred microliters of a 0.25% turkey red blood cells suspension (Bio Link Inc., Syracuse, NY) were added to each well, and plates were incubated for 2 h at room temperature. The reciprocal of the highest dilution showing complete hemagglutination was recorded as hemagglutination activity. In parallel, a recombinant H5 standard (A/Vietnam/1203/2004 H5N1) (Protein Science Corporation, Meriden, CT) was diluted in PBS and run as a control on each plate.

Figure 3A:
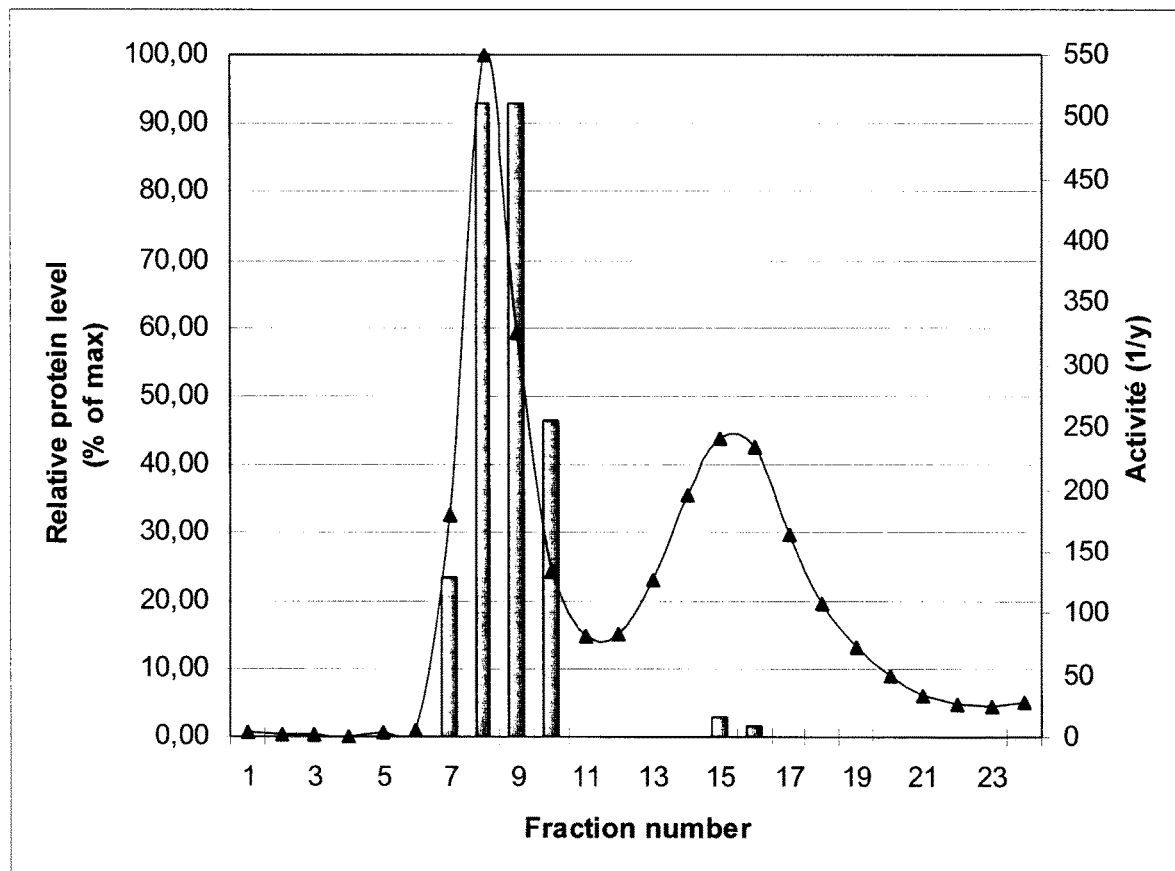
Figure 3B:
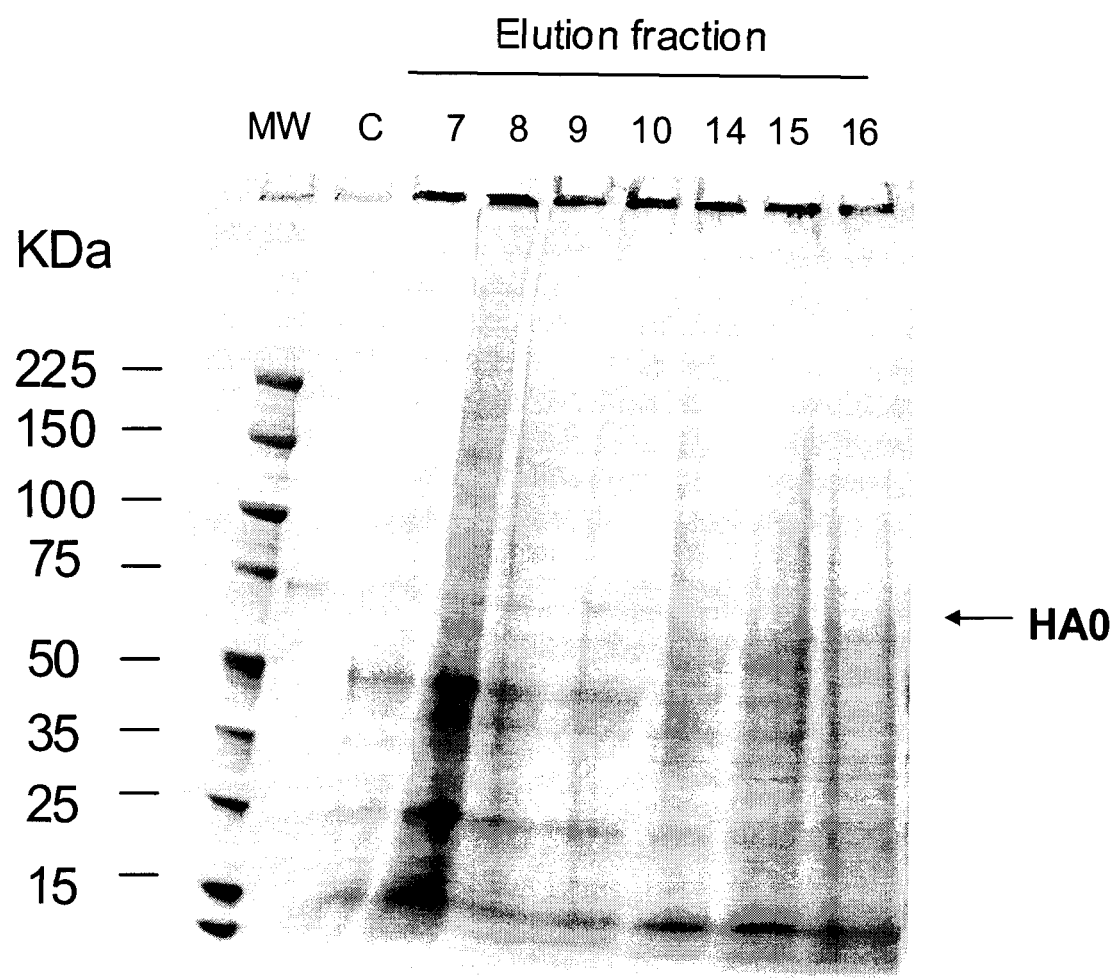

FIG. 3A shows that the hemagglutination activity is concentrated in the fractions corresponding to the void volume of the column, confirming that the hemagglutination activity originates from a high molecular weight structural organization. SDS-PAGE analysis (FIG. 3B) revealed that those same void volume fractions (fractions 7-10) also present the highest HA content, with a band corresponding to the HA0 monomer being detectable at approximately 75 kDa.

Example 3

Enzymatic Digestion of Plant Tissue Releases HA-VLPs with Fewer Contaminants

*N. benthamiana* plants were agroinfiltrated with AGL1/685 as described in Example 1. Leaves were collected on day 6 post-infiltration, cut into ~1 cm² pieces, digested, coarse-filtered and centrifuged as described in Example 1.

The controlled enzymatic digestion of the leaves removed the cell walls, at least partially, thus allowing for the release of proteins and components presents in the space between the cell wall and the plasma membrane into the extraction medium. Since most intracellular proteins and components were still undamaged and contained within the mostly intact protoplasts, an initial centrifugation step allowed for their removal, thus providing a resulting solution comprising cell wall degrading enzymes, in addition of the extracellular plant proteins and components (apoplastic fraction), as shown in FIG. 4.

Figure 4:
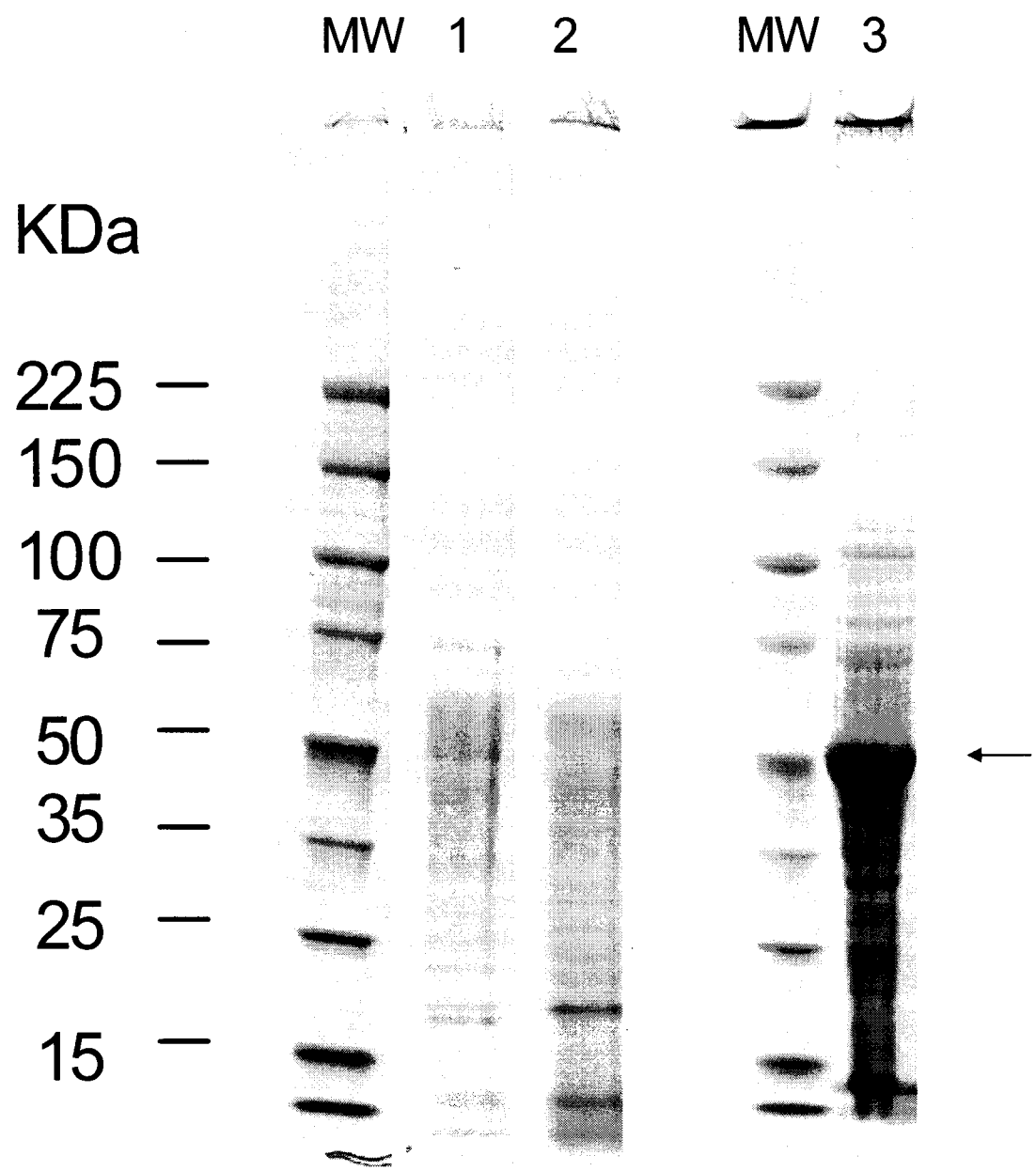

FIG. 4 shows a SDS-PAGE analysis of the resulting solution obtained following the controlled enzymatic digestion of leaves tissue as described previously, with lane 1 showing the enzyme mixture used and lane 2 showing the resulting solution following the enzymatic digestion. The protein content of a crude extract from Comitrol™ is provided on lane 3 for comparison. The biomass:buffer ratio for the extract presented in lane 2 was 1:5 (w/v) while it was 1:1 (w/v) for that in lane 3. Each of lanes 2 and 3 therefore contain proteins derived from an equivalent quantity of starting material. For approximately the same buffer:plant ratio, a mechanical plant extract contained a protein concentration of approximately 3.5-4 mg/ml, while the enzymatic plant extract obtained according to the present method presented a protein concentration of approximately 1 mg/ml.

The major contaminant present in lane 3 was found to be RubisCo (Ribulose-1,5-bisphosphate carboxylase oxygenase), which is made of two types of protein subunits: a large-chain (L, about 55 kDa) and a small-chain (S, about 13 kDa). A total of eight large-chain dimers and eight small-chains usually assemble with each other into a RubisCo 540 kDa larger complex. While this plant protein contaminant is found in large amount in plant extracts originating from mechanical extraction method (see arrow in FIG. 4), it is virtually absent in plant extracts obtained by the enzymatic digestion method described herein. Therefore, the present method allows for the elimination of this major plant protein contaminant, amongst others, at an early stage of the process.

Example 4

Enzymatic Digestion of Plant Tissue Releases HA-VLP in Conditions where it can be Directly Captured on a Cation Exchange Resin

*N. benthamiana* plants were agroinfiltrated with AGL1/685 as described in Example 1. Leaves were collected on day 6 post-infiltration, cut into ~1 cm² pieces and digested for 15 h at room temperature in an orbital shaker. The digestion buffer contained 1.0% (v/v) Multifect Pectinase FE, 1.0% (v/v) Multifect CX CG or and 1.0% (v/v) Multifect CX B (all from Genencor), each in a solution of 600 mM Mannitol, 75 mM Citrate, 0.04% sodium bisulfite pH 6.0 buffer using a biomass:digestion buffer ratio of 1:2.5 (w/v).

Following digestion, the apoplastic fraction was filtered through a 400 µm nylon filter to remove coarse undigested vegetal tissue (<5% of starting biomass). The filtered extract was then centrifuged at room temperature for 15 min at 5000×g to remove protoplasts and intracellular contaminants (proteins, DNA, membranes, vesicles, pigments, etc). Next, the supernatant was depth-filtered (for clarification) using a 0.65 µm glass fiber filter (Sartopore2/Sartorius Stedim) and a 0.45/0.2 µm filter, before being subjected to chromatography.

The clarified apoplastic fraction was loaded over a cation exchange column (Poros HS Applied Biosystems) equilibrated with an equilibration/elution buffer (50 mM NaPO$_4$, 100 mM NaCl, 0.005% Tween 80 pH 6.0). Once the UV was back to zero, the extract was step-eluted with the equilibration/elution buffer containing increasing concentrations of NaCl (500 mM). Where necessary, the chromatographic fractions were concentrated 10 times using Amicon™ devices equipped with 10 kDa MWCO. Protein analysis was performed as described in previous examples.

Figure 6:
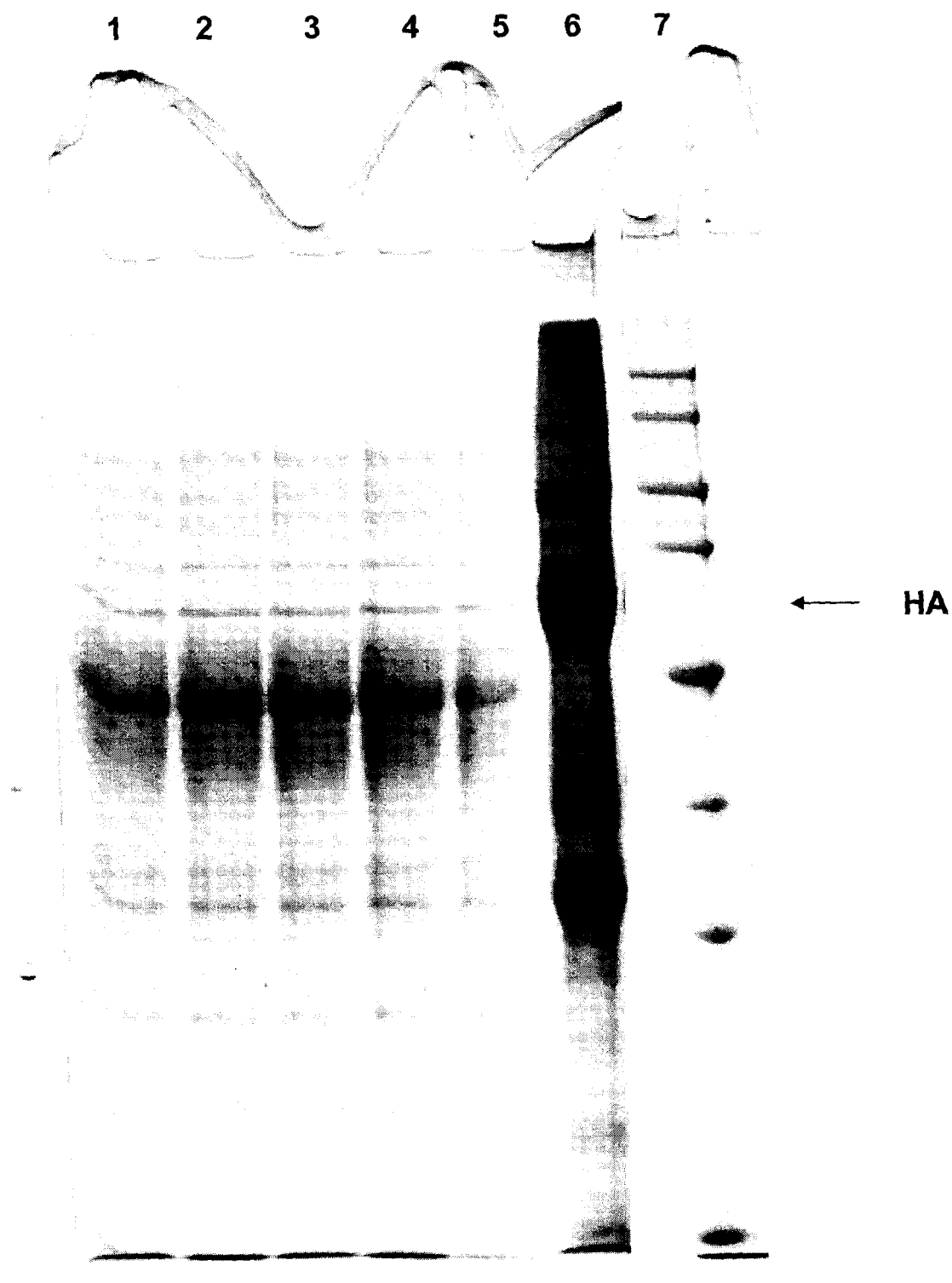

Under the above-mentioned conditions, most enzymes and plant proteins did not bind to the cation exchange resin whereas the HA-VLP did bind, thus providing a considerable enrichment in HA-VLPs in the eluted fraction (FIG. 6). In addition, as shown in FIG. 6, lane 4 and 5, the cellulases and pectinases did not bind to the cation exchange column at pH under 7. Consequently, recovery of HA-VLP, based on HA hemagglutination activity, was of 92% prior to loading on the cation exchange column, and of 66% in the eluted fraction. A purification factor of 194 was measured on the eluted fraction from the cation exchange resin.

Example 5

Addition of NaCl to the Digestion Buffer

N. benthamiana plants were agroinfiltrated with Agrobacterium AGL1 strains carrying a construct expressing a hemagglutinin of interest (H1/Cal WT, B/Flo, H5/Indo or H1/Cal X179A) as described in Example 1. Leaves were collected on day 6 post-infiltration, cut into ~1 cm² pieces and digested according to Example 4, except where noted below. Filtration, centrifugation and clarification were performed as described in Example 4.

NaCl was added to digestion buffer to evaluate its potential effect on the HA-VLP recovery rate. The suspected advantages were the potential prevention of non-specific association of HA with plant cells or with particle in suspension that are removed during clarification and potential effect on achievement and/or maintenance and/or improvement of colloidal stability of the HA-VLP.

Addition of 500 mM NaCl to the digestion buffer resulted in an increase of HA-VLP recovery yield per gram of biomass after removal of protoplasts and cellular debris by centrifugation. However, this increase was only noted with the for the H1/Cal WT and B/Flo strains, while the recovery yield for H5 was not significantly increased by this approach (Table 4).

TABLE 4

Effect of the addition of NaCl to the digestion step on the HA-VLP recovery yield (as measured by hemagglutination activity unit, dil: reciprocal of dilution)

| HA strain | Digestion conditions | Concentration in HA (dil/ml) | Yields (dil/g) | Yield increased (X-fold)[1] |
|---|---|---|---|---|
| H5 Indo/05 (#972) | Ø NaCl | 4608 | 12,430 | 1.2 |
| | 500 mM NaCl | 4608 | 14,921 | |
| H1 CA/07 WT (#604) | Ø NaCl | 384 | 1,206 | 2.1 |
| | 500 mM NaCl | 768 | 2,481 | |
| H1 CA/07 X-179A (#605) | Ø NaCl | 96 | 299 | 8.1 |
| | 500 mM NaCl | 768 | 2,419 | |
| B Flo/4 (475) | Ø NaCl | 16 | 52 | 7.5 |
| | 500 mM NaCl | 128 | 392 | |

[1]Yield (dil/g) with NaCl divided by Yield (dil/g) without NaCl

Addition of 500 mM NaCl during the digestion further resulted in an increase of the release of HA-VLP during digestion, which in turn resulted into increased recovery rate after clarification for both H1/Cal WT and H1/Cal X-179A strains (Table 5), but not for the H5/Indo strain.

TABLE 5

Effect of the addition of NaCl to the digestion step on the HA-VLP recovery yield (as measured by hemagglutination activity unit) after the clarification step.

| HA strain | Digestion conditions | Recovery after depth filtration[1] | Increase in recovery (X-fold) |
|---|---|---|---|
| H5/Indo (#972) | Ø NaCl | 100% | 1.0 |
| | 500 mM NaCl | 100% | |
| H1/Cal WT (#604) | Ø NaCl | 25% | 3.0 |
| | 500 mM NaCl | 75% | |
| H1/Cal X-179A (#605) | Ø NaCl | 50% | 2.0 |
| | 500 mM NaCl | 100% | |

[1]Recovery is expressed in percentage of hemagglutination activity obtained after depth filtration compared to the activity found in the centrifuged digested extract.

Figure 7A:
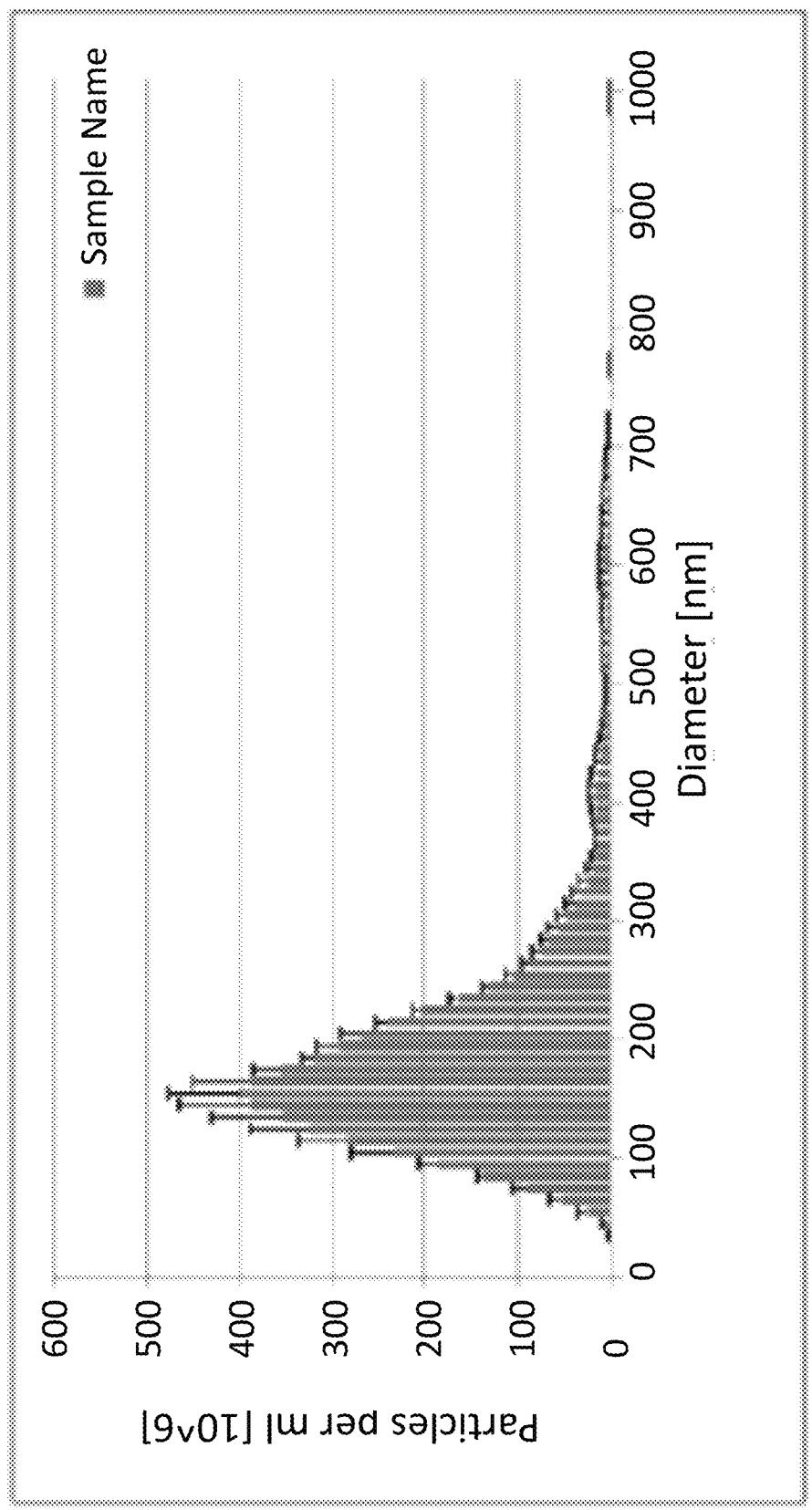
Figure 7B:
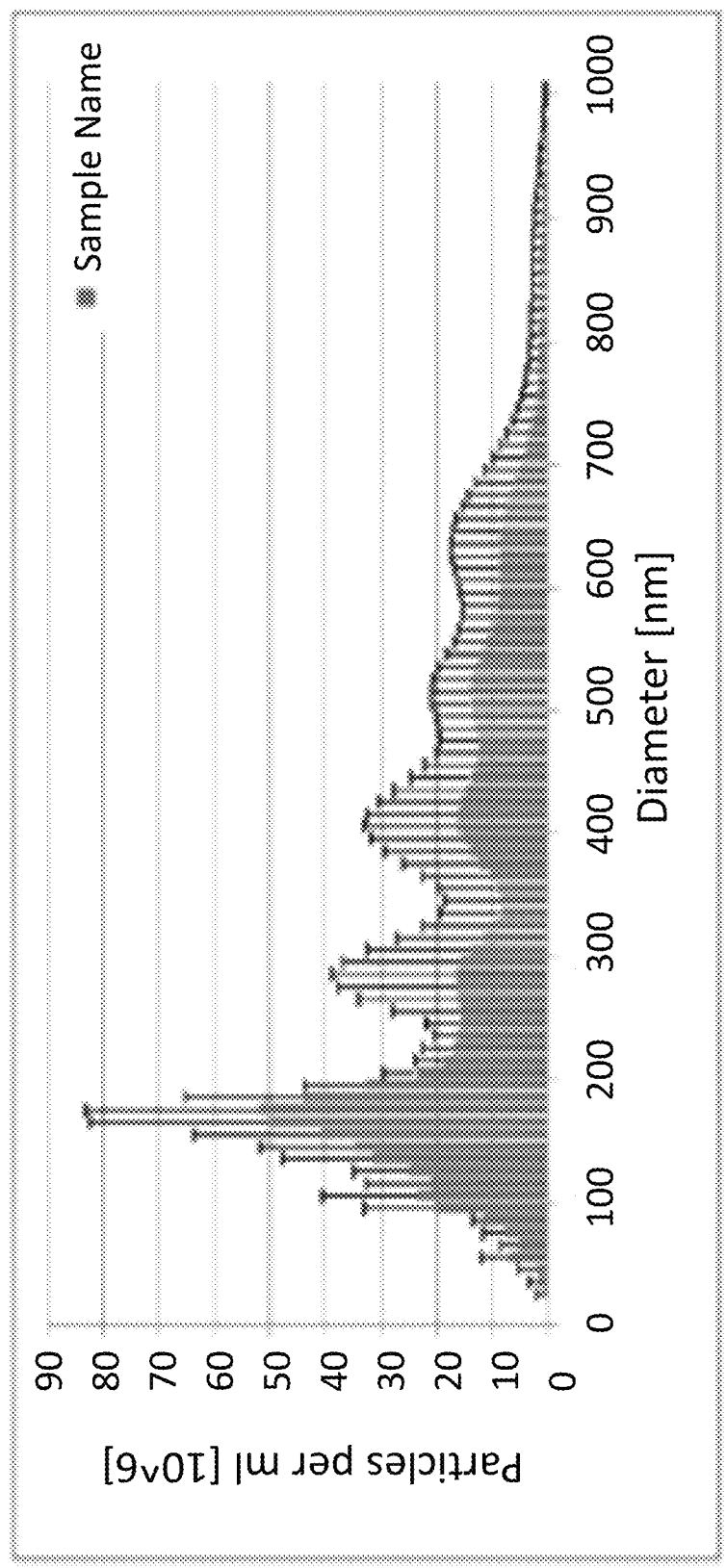
Figure 7C:
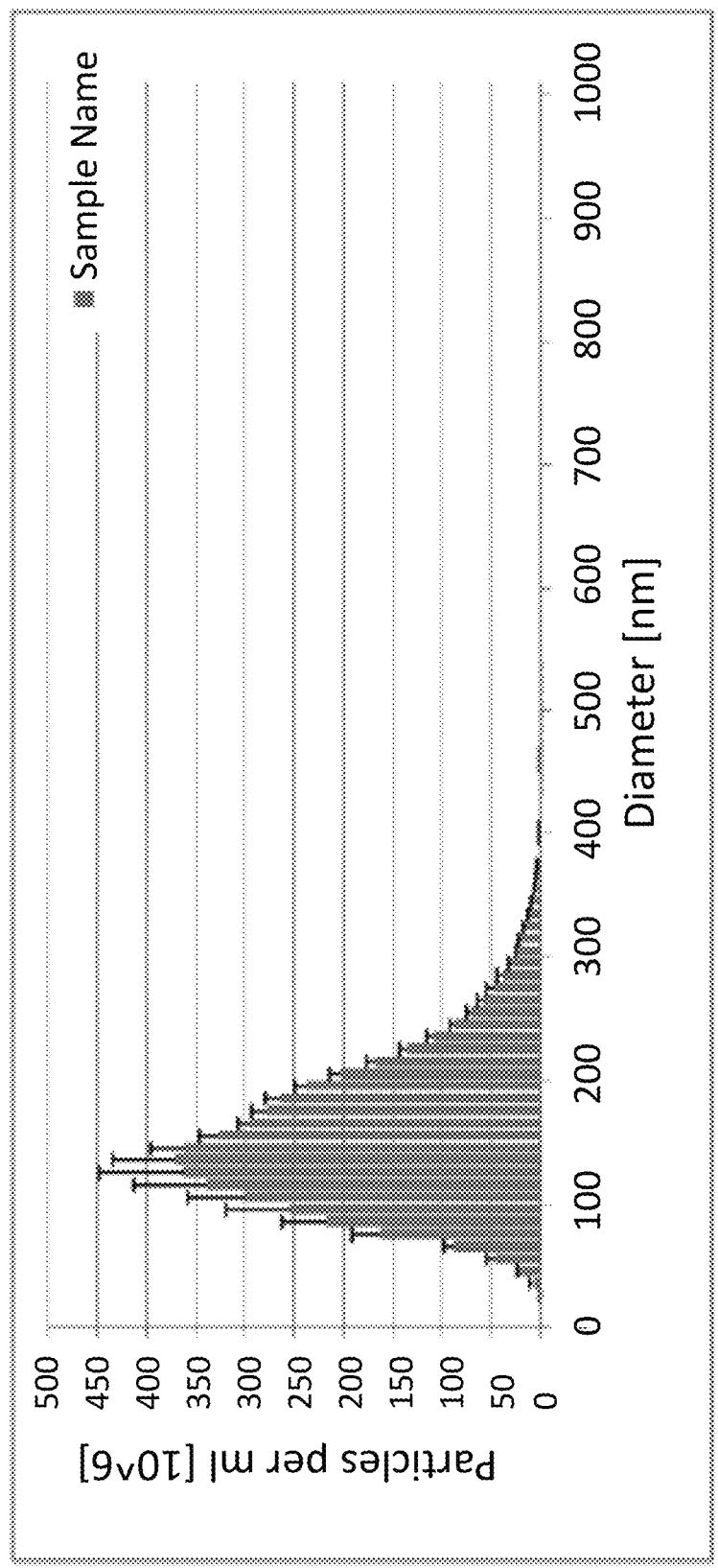
Figure 8:
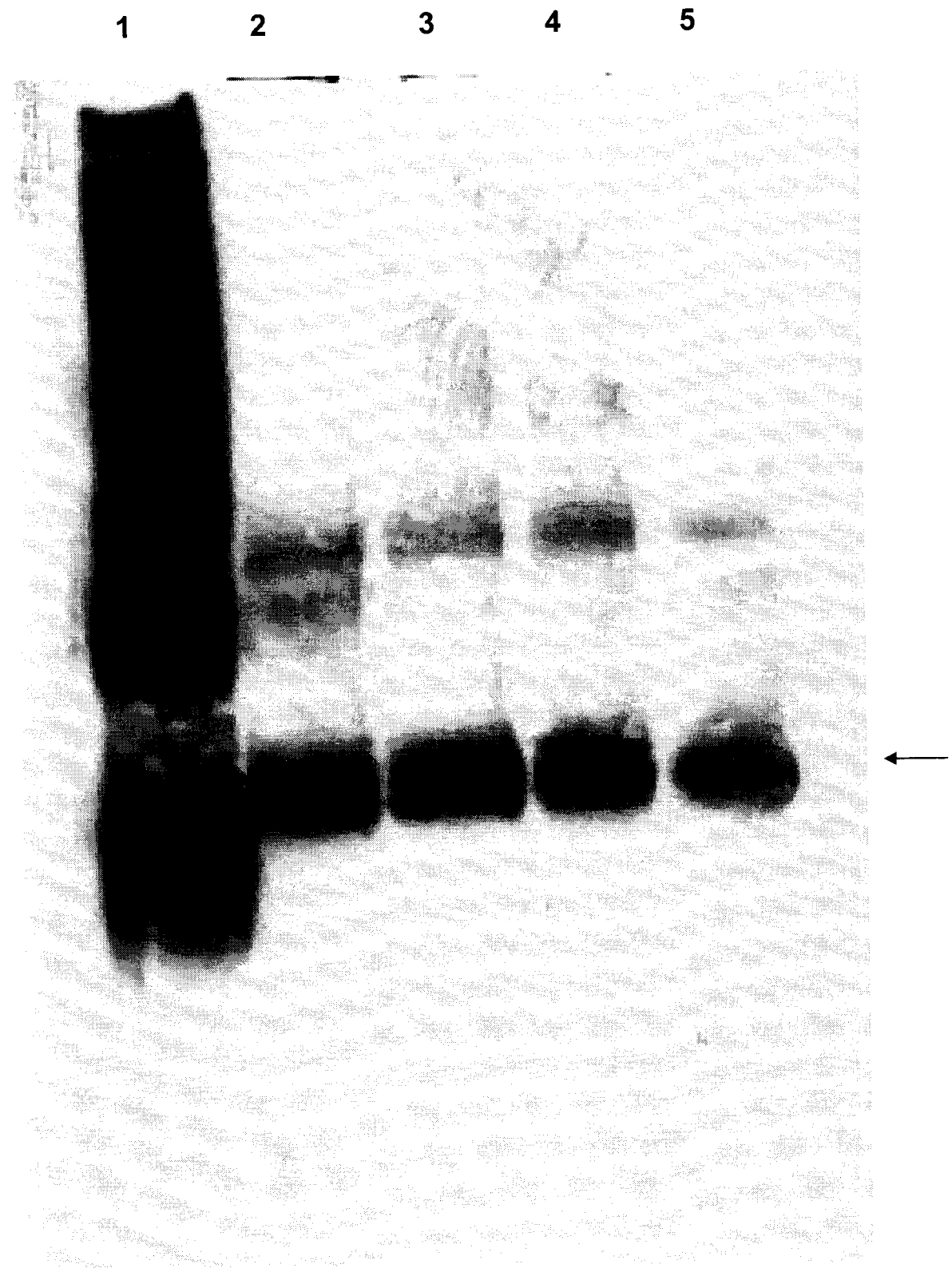

The association state of the HA-VLP, with and without the addition of NaCl during enzymatic digestion, was studied using Nanoparticle Tracking Analysis (NTA) for H5/Indo and H1/Cal WT (FIGS. 7A and 7B respectively). A monodisperse preparation of particles was observed for H5 when digestion was performed in absence of NaCl, while the H1/Cal preparation showed much larger array of particle species. The addition of NaCl to the digestion buffer reduced HA-VLP self-association for H1/Cal, as shown by the fairly monodisperse particle distribution found in FIG. 7C. The number of particles at 150 nm for H1/Cal WT-VLPs was enhanced (ca 5-fold) by the addition of 500 mM NaCl to the digestion buffer.

Example 6

Controlling the Release of Pigments

N. benthamiana plants were agoinfiltrated with Agrobacterium AGL1 strains carrying a construct expressing a hemagglutinin of interest (H5/Indo) as described in Example 1. Leaves were collected on day 6 post-infiltration, cut into ~1 cm² pieces, and digested as described in Example 4, with addition of either 500 mM NaCl or 500 mM NaCl and 25 mM EDTA to the digestion buffer. Filtration, centrifugation and clarification were performed as described in Example 4.

Release of components having a green color during the enzymatic digestion step led to purified preparation of VLP having a greenish coloration. The composition of the cell wall digestion solution was therefore investigated and adjusted to obtain a VLP purified preparation having a reduced green coloration, and thus an increased purity. Without wishing to be bound by theory, since $Ca^{2+}$ plays a critical role in the retention of constituents of the cell wall's middle lamellae together, and given the fact that there is usually a high concentration of $Ca^{2+}$ in plant cell wall, the addition of $Ca^{2+}$-chelator EDTA could facilitate the enzymatic depolymerisation of the cell wall, thereby preserving intact intracellular organelles, such as chloroplasts, and preventing the release green-pigments components.

As shown in Table 6, the addition of 25 mM EDTA to the digestion buffer allowed for the reduction of the green coloration of the purified H5-VLP preparation, as evaluated by measuring the difference in absorption of the preparation ($OD_{672nm}$-$OD_{650nm}$). When the green constituents were released in high quantity, or not suitably removed, VLP preparation exhibited a $\Delta OD > 0.040$.

TABLE 6

Effect of the addition of 25 mM EDTA to the digestion buffer on green coloration of H5-VLP preparations.

| | $OD_{672\ nm}-OD_{650\ nm}$ |
|---|---|
| 0 mM NaCl, 0 mM EDTA | 0.071 ± 0.061 |
| 500 mM NaCl | 0.087 ± 0.060 |
| 500 mM NaCl + 25 mM EDTA | 0.010 ± 0.002 |

Example 7

Alternative Digestion Buffer Compositions

N benthamiana plants were agroinfiltrated with *Agrobacterium* AGL1 strains carrying a construct expressing a hemagglutinin of interest (H5/Indo) as described in Example 1. Leaves were collected on day 6 post-infiltration, cut into ~1 $cm^2$ pieces and digested according to Example 4, with modification of digestion buffer to include 0%, 0.25%, 0.5%, 0.75% or 1% v/v Multifect Pectinase FE, Multifect CX-CG cellulase and Multifect CX B cellulose as noted in Tables 7-9. Filtration, centrifugation and clarification were as described in Example 4.

As shown in following tables 7 and 8, pectinase has been demonstrated to be non-essential in the digestion buffer. Similar levels of H5/Indo or H1/Cal WT VLP can be extracted with the present method either in the presence or absence of pectinase. Furthermore, it has been found that reducing the concentration of cellulase when compared to previous examples had no significant impact on the quality of extraction (Table 9).

TABLE 7

Release of H5/Indo VLP by digestion of *N. benthamiana* leaves. All conditions were tested in replicates. (Concentration in HA-VLP measured by hemagglutination activity, dil: reciprocal of dilution)

| Pectinase (% v/v) | Cellulase* (% v/v) | Concentration in H5 VLP (dil/ml) |
|---|---|---|
| 1 | 1 | 1152 |
| 0.5 | 1 | 6144 |
| 0 | 1 | 768 |
| 0 | 2 | 1536 |

*Multifect CX GC

TABLE 8

Release of H1/Cal WT VLP by digestion of *N. benthamiana* leaves. All conditions were tested in replicates. (Concentration in HA-VLP measured by hemagglutination activity, dil: reciprocal of dilution)

| Pectinase (% v/v) | Cellulase* (% v/v) | Concentration in H1 VLP (dil/ml) |
|---|---|---|
| 1 | 2 | 2304 |
| 0 | 2 | 3840 |

*1% each of Multifect CX GC and Multifect CX B

TABLE 9

Release of H1/Cal WT VLP by digestion of *N. benthamiana* leaves. All conditions were tested in replicates. (Concentration in HA-VLP measured by hemagglutination activity, dil:, reciprocal of dilution)

| Pectinase (% v/v) | Cellulase* (% v/v) | Concentration in H1 VLP (dil/ml) |
|---|---|---|
| 1.0 | 1 | 384 |
| 0.75 | 1 | 480 |
| 0.50 | 1 | 480 |
| 0.25 | 1 | 480 |

*Multifect CX GC

Example 8

Enzymatic Digestion in Conditions Near to Neutral pH

Controlling the pH during the digestion can be critical for the extraction of some VLPs. Taking into account that the depolymerisation of the cell wall occurring during the digestion step can release acid sugars that could acidify the solution (i.e. from pH 6 to 5) in the presence of appropriate buffers, and that some VLPs (such as those comprising H3/Bris and B/Flo HA) have already demonstrated a strong sensitivity to mildly acidic conditions, impact of such a potential acidification on the yield of VLP produced was investigated.

*N. benthamiana* plants were agroinfiltrated with *Agrobacterium* AGL1 strains carrying a construct expressing a hemagglutinin of interest (B/Flo, H5/Indo, H3/Bris) as described in Example 1. Leaves were collected on day 6 post-infiltration, cut into ~1 $cm^2$ pieces and digested according to Example 4, with modification of digestion conditions to include 500 mM NaCl; 25 or 50 mM EDTA; 0.03 or 0.04% sodium bisulfite; 0, 100, 200 or 600 mM mannitol, 75, 125 or 150 mM citrate; and/or 75 mM $NaPO_4$; with the pH of the digestion buffer adjusted as set out in Tables 10-14. Filtration, centrifugation and clarification were as described in Example 4.

Various digestion buffer compositions were tested to achieve a pH of approximately 5.5 by the end of the enzymatic digestion, including increased concentration of citrate (buffer effect between pH 3.0 and 5.4) and addition of sodium phosphate (buffer effect at pH above 6.0). Table 10 shows that VLPs from the B strain were extracted more efficiently when post-digestion pH was close to pH 6.0.

TABLE 10

Effect of the digestion buffer composition on the extraction yield of B/Flo VLPs.

| Buffer composition[1] | Concentration of B/Flo VLP (dil/ml) | Protein concentration (mg/ml) | pH post-digestion |
|---|---|---|---|
| 75 mM Citrate + 500 mM NaCl + 25 mM EDTA pH 6.0 | 1 | 0.92 | 5.0 |
| 75 mM Citrate pH 6.0 | 0 | 1.43 | 5.6 |
| 125 mM Citrate + 500 mM NaCl + 25 mM EDTA pH 6.0 | 1.5 | 1.07 | 5.4 |
| 150 mM Citrate + 500 mM NaCl + 25 mM EDTA pH 6.0 | 1.5 | 1.07 | 5.4 |
| 125 mM Citrate + 75 mM $NaPO_4$ + 500 mM NaCl + 25 mM EDTA pH 6.5 | 4 | 2.19 | 5.9 |

TABLE 10-continued

Effect of the digestion buffer composition on the extraction yield of B/Flo VLPs.

| Buffer composition[1] | Concentration of B/Flo VLP (dil/ml) | Protein concentration (mg/ml) | pH post-digestion |
|---|---|---|---|

[1]All buffers contained 600 mM mannitol, sodium metabisulfite 0.04%

Next, the effect of initiating the digestion at a higher pH in order to reach final pH value close to pH 6.0 was tested. As shown in Table 11, the digestion of plant cell wall with such near-neutral conditions was possible, and did not impaired the extraction yield for H5/Indo VLPs.

TABLE 11

Effect of the initial pH of the digestion buffer on the extraction yield of H5/Indo VLPs.

| Initial pH of digestion solution[1] | Concentration of H5/Indo VLP (dil/ml) | Protein concentration (mg/ml) | pH post-digestion |
|---|---|---|---|
| 6.5 | 2304 | 2.79 | 6.08 |
| 6.4 | 1536 | 2.31 | 5.93 |
| 6.3 | 2304 | 2.40 | 5.81 |
| 6.2 | 2304 | 2.09 | 5.73 |
| 6.1 | 2304 | 1.72 | 5.61 |

[1]All digestion buffers contained 600 mM mannitol, sodium metabisulfite 0.04%, 125 mM Citrate + 75 mM $NaPO_4$ + 500 mM NaCl + 25 mM EDTA Other components of the digestion solution were also shown to be modifiable without negatively affecting the extraction yield of VLPs. Table 12 illustrates modifications that can be applied to the digestion solution in order to enhance the extraction yield of B/Flo VLPs, while obtaining a post-digestion pH of 5.4-5.7. Such modifications include increasing the concentration of citrate and adding a $PO_4$ buffer. It has been found that increasing the concentration of EDTA generally led to a more acidified extract and to lower VLP extraction yields.

TABLE 12

Effect of various digestion buffer components on the extraction yield of B/Flo VLPs.

| Buffer composition[1] | | | | | Concentration of B VLP (dil/ml) | Protein concentration (mg/ml) | pH post-digestion |
|---|---|---|---|---|---|---|---|
| Mannitol (mM) | Citrate (mM) | $PO_4$ (mM) | EDTA (mM) | pH | | | |
| 600 | 75 | 0 | 25 | 6.1 | 2 | 1.07 | 5.0 |
| 600 | 125 | 0 | 25 | 6.1 | 192 | 0.83 | 5.7 |
| 600 | 125 | 75 | 25 | 6.2 | 192 | 1.81 | 5.5 |
| 600 | 125 | 75 | 50 | 6.2 | 96 | 1.26 | 5.4 |
| 200 | 125 | 75 | 25 | 6.2 | 384 | 1.05 | 5.7 |
| 200 | 125 | 75 | 50 | 6.2 | 96 | 1.04 | 5.4 |
| 200 | 125 | 75 | 75 | 6.2 | 96 | 1.55 | 5.4 |

[1]All buffers contained 500 mM NaCl and sodium metabisulfite 0.04%.

Buffer composition was further modified to improve the extraction yield of H3/Brisbane VLPs (Table 13)

TABLE 13

Effect of the concentrations of mannitol and sodium bisulfite in the digestion solution on the extraction yield of H3/Bris VLPs.

| Buffer composition | | | | Protein concentration (mg/ml) | pH post-digestion |
|---|---|---|---|---|---|
| Mannitol (mM) | Sodium bisulfite (%) | EDTA (mM) | pH | | |
| 600 | 0.04 | 25 | 6.2 | 1.87 | 5.7 |
| 600 | 0.04 | 50 | 6.2 | 1.62 | 5.6 |
| 200 | 0.03 | 25 | 6.2 | 1.89 | 5.7 |
| 200 | 0.03 | 50 | 6.2 | 1.24 | 5.6 |

[1]All buffers containing 125 mM Citrate, 75 mM $NaPO_4$, 500 mM NaCl.

As shown in Tables 12 and 13, mannitol concentration could be reduced to 200 mM without significantly affecting VLPs extraction yield. Further reduction of mannitol concentrations to 100 mM, and even the total omission of mannitol from the digestion solution, did not significantly affect the level of HA-VLP obtained (Table 14).

TABLE 14

Released of H5/Indo VLP from digestion of biomass performed in buffers with different concentration of mannitol.

| Mannitol concentration of the digestion solution[1] | Concentration of H5/Indo VLP (dil/ml) | Protein concentration (mg/ml) |
|---|---|---|
| [2]Trial 1: without mannitol | 2304 | 1.62 |
| [2]Trial 1: with 600 mM mannitol | 3072 | 1.73 |
| [2]Trial 2: with 100 mM mannitol | 4608 | 1.77 |
| [2]Trial 2: with 600 mM mannitol | 4608 | 2.0 |

[1]All buffers containing 75 mM Citrate pH 6.0 + sodium metabisulfite 0.04%.
[2]Two trials were were performed to compare the extraction yields of VLPs without mannitol (Trial 1) and with 100 mM mannitol (Trial 2) versus 600 mM mannitol.

Example 9

Suitability of Enzymatic Digestion to a Broad Variety of HA-VLPs

The enzymatic digestion method for plant biomass described herein has the potential to be applied to extracting of a broad variety of HA-VLPs. Adding to the extraction of HA-VLPs comprising H5/Indo, H1/Cal WT VLP, H3/Bris and B/Flo shown in previous examples, the method described herein was also shown to be suitable for the extraction of HA-VLPs from seasonal H1/Bris and H1/NC, as shown in Table 15.

TABLE 15

Release of seasonal H1/Bris and H1/NC VLP from digestion of agroinfiltrated *N. benthamiana* leaves. (concentration in HA measured by hemagglutination activity, dil: reciprocal of dilution)

| HA strain | Concentration in HA (dil/ml) |
|---|---|
| H1/Bri | 1536 |
| H1/NC | 384 |

All citations are herein incorporated by reference, as if each individual publication was specifically and individually indicated to be incorporated by reference herein and as though it were fully set forth herein. Citation of references herein is not to be construed nor considered as an admission that such references are prior art to the present invention.

One or more currently preferred embodiments of the invention have been described by way of example. The invention includes all embodiments, modifications and variations substantially as hereinbefore described and with reference to the examples and figures. It will be apparent to persons skilled in the art that a number of variations and modifications can be made without departing from the scope of the invention as defined in the claims. Examples of such modifications include the substitution of known equivalents for any aspect of the invention in order to achieve the same result in substantially the same way.

What is claimed is:

1. A method of preparing plant derived virus-like particles (VLPs) comprising an influenza hemagglutinin (HA) with reduced plant protein contaminants and increased yield, the method comprising:

a. obtaining a plant or plant matter comprising apoplast-localized VLPs, wherein the apoplast-localized VLPs comprise the influenza HA, wherein the plant matter consists of plant leaves, leaf pieces, shredded leaves, or a combination thereof;

b. producing a digested fraction, the digested fraction comprising an apoplast fraction, a protoplast fraction and plant debris, by extraction from the plant or plant matter, wherein the extraction consists of an enzymatic extraction, with a cell wall degrading enzyme mixture, wherein the cell wall degrading enzyme mixture comprises one or more than one cellulase and one or more than one pectinase, a first salt consisting of about 0.01% to about 0.05% sodium bisulfite, about 200 mM to about 600 mM of a second salt, about 0.1 M to about 0.8 M osmoticum, and a buffer or buffer system which maintains the pH in the range of about 5.2 to about 6.2, at a temperature of about 18° C. to about 22° C., with agitation, wherein substantially all of the protoplasts in the protoplast fraction are disrupted protoplasts; and c. separating the plant debris from the digested fraction using filtration with a mesh size of more than 250 μm, centrifuging to remove organelles, and to produce a supernatant, and recovering the plant-derived VLPs comprising the influenza HA from the supernatant, wherein the supernatant comprising the plant-derived VLPs has reduced plant protein contaminants and increased yield compared to a supernatant of a corresponding liquid extract produced by mechanical extraction.

2. The method of claim 1, wherein the cell wall degrading enzyme mixture does not include one or more of a lipase or a protease.

3. The method of claim 1 wherein in the step of obtaining (step a), the plant is transformed with a nucleic acid comprising a nucleotide sequence encoding the influenza hemagglutinin, and the plant or plant matter is harvested.

4. The method of claim 3, wherein the nucleic acid is introduced into the plant in a transient manner.

5. The method of claim 3, wherein the nucleic acid is stably integrated within a genome of the plant.

6. The method of claim 1 wherein in the step of obtaining (step a), the plant is grown and the plant or plant matter is harvested.

7. The method of claim 1 wherein the plant derived VLPs do not include neuraminidase or influenza M protein.

8. The method of claim 1 further comprising a step of d) purifying the plant derived VLPs from the supernatant.

9. The method of claim 8, wherein the step of purifying comprises filtering the supernatant fraction using depth filtration to produce a clarified extract, followed by chromatography of the clarified extract using a cation exchange resin.

10. A method of preparing plant-derived virus-like particles (VLPs) comprising a plant-derived lipid envelope and an influenza hemagglutinin (HA) with reduced plant protein contaminants and increased yield, the method comprising:

a. obtaining a plant, or plant matter comprising apoplast-localized VLPs, wherein the apoplast-localized VLPs comprising the influenza HA, wherein the plant matter consists of plant leaves, leaf pieces, shredded leaves or a combination thereof;

b. digesting the plant or plant matter using a cell wall degrading enzyme mixture comprising one or more than one cellulase and one or more than one pectinase, a first salt consisting of about 0.01% to about 0.05% sodium bisulfite, about 200 mM to about 600 mM of a second salt, about 0.1 M to about 0.8 M osmoticum, and a buffer or buffer system which maintains the pH in the range of about 5.2 to about 6.2, at a temperature of about 18° C. to about 22° C., with agitation, to produce a digested fraction, the digested fraction comprising a protoplast fraction, an apoplast fraction comprising one or more than one apoplastic protein complex that comprises the VLPs and plant debris, wherein the digestion and agitation disrupts substantially all of the protoplasts in the protoplast fraction; and c. separating the plant debris from the digested fraction using filtration with a mesh size of more than 250 μm, centrifuging to remove organelles, and to produce a supernatant, recovering the one or more than one apoplastic protein complex from the supernatant, wherein the supernatant comprising the one or more than one apoplastic protein complex has reduced plant protein contaminants and increased yield compared to a supernatant of a corresponding digested fraction produced by mechanical extraction.

11. The method of claim 10 wherein the cell wall degrading enzyme mixture does not include one or more of a lipase or a protease.

12. The method of claim 10 further comprising the step of d) purifying the plant derived VLPs from the one or more than one apoplastic protein complex.

13. The method of claim 12, wherein the step of purifying comprises filtering the supernatant using depth filtration to produce a clarified extract, followed by chromatography of the clarified extract using a cation exchange resin.

14. The method of claim 10 wherein in the step of obtaining (step a), the plant is transformed with a nucleic acid comprising a nucleotide sequence encoding the influenza hemagglutinin, and the plant or plant matter is harvested.

15. The method of claim 14, wherein the nucleic acid is introduced into the plant in a transient manner.

16. The method of claim 14, wherein the nucleic acid is stably integrated within a genome of the plant.

17. The method of claim 10 wherein in the step of obtaining (step a), the plant is grown and the plant or plant matter is harvested.

18. The method of claim 10 wherein the VLPs do not include neuraminidase or influenza M protein.

19. The method of claim 1, wherein the osmoticum is selected from the group consisting of mannitol, sorbitol, sugar alcohols and polyethylene glycol (PEG) of varying polymer lengths.

20. The method of claim 1, wherein the concentration of the osmoticum is from about 0.4 M to about 0.8 M.

21. The method of claim 10, wherein the osmoticum is selected from the group consisting of mannitol, sorbitol, sugar alcohols and polyethylene glycol (PEG) of varying polymer lengths.

22. The method of claim 10, wherein the concentration of the osmoticum is from about 0.4 M to about 0.8 M.

23. The method of claim 1, wherein the second salt comprises $Ca^{2+}$, $Mg^{2+}$, $Na^{+}$, $K^{+}$, NaCl, $CaCl_2$, $CuSO_4$ or $KNO_3$.

24. The method of claim 10, wherein the second salt comprises $Ca^{2+}$, $Mg^{2+}$, $Na^{+}$, $K^{+}$, NaCl, $CaCl_2$, $CuSO_4$ or $KNO_3$.

25. The method of claim 1, wherein the cell wall degrading enzyme mixture further comprises about 5 mM to about 200 mM EDTA or EGTA.

26. The method of claim 1, wherein the cell wall degrading enzyme mixture further comprises 0 to about 125 mM citrate.

27. The method of claim 10, wherein the cell wall degrading enzyme mixture further comprises about 5 mM to about 200 mM EDTA or EGTA.

28. The method of claim 10, wherein the cell wall degrading enzyme mixture further comprises 0 to about 125 mM citrate.

29. The method of claim 1, wherein the plant protein contaminants comprise Ribulose-1,5-bisphosphate carboxylase oxygenase (RubisCo).

30. The method of claim 1, wherein the mechanical extraction comprises grinding the plant or plant matter with a mortar and pestle.

31. The method of claim 1, wherein the yield is at least 2.5 times higher.

32. The method of claim 10, wherein the plant protein contaminants comprise Ribulose-1,5-bisphosphate carboxylase oxygenase (RubisCo).

33. The method of claim 10, wherein the mechanical extraction comprises grinding the plant or plant matter with a mortar and pestle.

34. The method of claim 10, wherein the yield is at least 2.5 times higher.

* * * * *

SEQUENCE LISTING

<160> NUMBER OF SEQ ID NOS: 14

<210> SEQ ID NO 1
<211> LENGTH: 3067
<212> TYPE: DNA
<213> ORGANISM: Artificial Sequence
<220> FEATURE:
<223> OTHER INFORMATION: Synthesized construct 685

<400> SEQUENCE: 1

```
ttaattaaga attcgagctc caccgcggaa acctcctcgg attccattgc ccagctatct      60
gtcactttat tgagaagata gtggaaaagg aaggtggctc ctacaaatgc catcattgcg     120
ataaaggaaa ggccatcgtt gaagatgcct ctgccgacag tggtcccaaa gatggacccc     180
cacccacgag gagcatcgtg gaaaagaag acgttccaac cacgtcttca aagcaagtgg     240
attgatgtga tatctccact gacgtaaggg atgacgcaca atcccactat ccttcgcaag     300
acccttcctc tatataagga agttcatttc atttggagag gtattaaaat cttaataggt     360
tttgataaaa gcgaacgtgg ggaaacccga accaaacctt cttctaaact ctctctcatc     420
tctcttaaag caaacttctc tcttgtcttt cttgcgtgag cgatcttcaa cgttgtcaga     480
tcgtgcttcg gcaccagtac aacgttttct ttcactgaag cgaaatcaaa gatctctttg     540
tggacacgta gtgcggcgcc attaaataac gtgtacttgt cctattcttg tcggtgtggt     600
cttgggaaaa gaaagcttgc tggaggctgc tgttcagccc catacattac ttgttacgat     660
tctgctgact ttcggcgggt gcaatatctc tacttctgct tgacgaggta ttgttgcctg     720
tacttctttc ttcttcttct tgctgattgg ttctataaga aatctagtat tttctttgaa     780
acagagtttt cccgtggttt tcgaacttgg agaaagattg ttaagcttct gtatattctg     840
cccaaatttg tcgggcccat ggagaaaata gtgcttcttc ttgcaatagt cagtcttgtt     900
aaaagtgatc agatttgcat tggttaccat gcaaacaatt caacagagca ggttgacaca     960
atcatggaaa agaacgttac tgttacacat gcccaagaca tactggaaaa gacacacaac    1020
gggaagctct gcgatctaga tggagtgaag cctctaattt taagagattg tagtgtagct    1080
ggatggctcc tcgggaaccc aatgtgtgac gaattcatca atgtaccgga atggtcttac    1140
atagtggaga aggccaatcc aaccaatgac ctctgttacc cagggagttt caacgactat    1200
gaagaactga aacacctatt gagcagaata aaccattttg agaaaattca aatcatcccc    1260
aaaagttctt ggtccgatca tgaagcctca tcaggagtta gctcagcatg tccatacctg    1320
ggaagtccct cctttttag aaatgtggta tggcttatca aaaagaacag tacataccca    1380
acaataaaga aaagctacaa taataccaac caagaggatc ttttggtact gtggggaatt    1440
caccatccta atgatgcggc agagcagaca aggctatatc aaaacccaac cacctatatt    1500
tccattggga catcaacact aaaccagaga ttggtaccaa aaatagctac tagatccaaa    1560
gtaaacgggc aaagtggaag gatggagttc ttctggacaa ttttaaaacc taatgatgca    1620
atcaacttcg agagtaatgg aaatttcatt gctccagaat atgcatacaa aattgtcaag    1680 aaagggact cagcaattat gaaagtgaa ttggaatatg gtaactgcaa caccaagtgt    1740
```

```
caaactccaa tgggggcgat aaactctagt atgccattcc acaacataca ccctctcacc    1800
atcggggaat gccccaaata tgtgaaatca aacagattag tccttgcaac agggctcaga    1860
aatagccctc aaagagagag cagaagaaaa aagagaggac tatttggagc tatagcaggt    1920
tttatagagg gaggatggca gggaatggta gatggttggt atgggtacca ccatagcaat    1980 gagcaggga gtgggtacgc tgcagacaaa gaatccactc aaaaggcaat agatggagtc    2040
accaataagg tcaactcaat cattgacaaa atgaacactc agtttgaggc cgttggaagg    2100
gaatttaata acttagaaag gagaatagag aatttaaaca agaagatgga agacgggttt    2160
ctagatgtct ggacttataa tgccgaactt ctggttctca tggaaaatga gagaactcta    2220
gactttcatg actcaaatgt taagaacctc tacgacaagg tccgactaca gcttagggat    2280
aatgcaaagg agctgggtaa cggttgtttc gagttctatc acaaatgtga taatgaatgt    2340
atggaaagta taagaaacgg aacgtacaac tatccgcagt attcagaaga agcaagatta    2400
aaaagagagg aaataagtgg ggtaaaattg gaatcaatag gaacttacca aatactgtca    2460
atttattcaa cagtggcgag ttccctagca ctggcaatca tgatggctgg tctatcttta    2520
tggatgtgct ccaatggatc gttacaatgc agaatttgca tttaaaggcc tattttcttt    2580
agtttgaatt tactgttatt cggtgtgcat ttctatgttt ggtgagcggt tttctgtgct    2640
cagagtgtgt ttatttttatg taatttaatt tctttgtgag ctcctgttta gcaggtcgtc    2700
ccttcagcaa ggacacaaaa agattttaat tttattaaaa aaaaaaaaa aaagaccgg    2760 gaattcgata tcaagcttat cgacctgcag atcgttcaaa catttggcaa taaagtttct    2820
taagattgaa tcctgttgcc ggtcttgcga tgattatcat ataatttctg ttgaattacg    2880
ttaagcatgt aataattaac atgtaatgca tgacgttatt tatgagatgg gttttatga    2940 ttagagtccc gcaattatac atttaatacg cgatagaaaa caaatatag cgcgcaaact    3000 aggataaatt atcgcgcgcg gtgtcatcta tgttactaga ttctagagtc tcaagcttcg    3060
gcgcgcc                                                             3067
```

<210> SEQ ID NO 2  
<211> LENGTH: 568  
<212> TYPE: PRT  
<213> ORGANISM: Artificial Sequence  
<220> FEATURE:  
<223> OTHER INFORMATION: Synthesized amino acid encoded by Seq Id No: 1

<400> SEQUENCE: 2

```
Met Glu Lys Ile Val Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Thr Asn Asp Leu Cys Tyr Pro Gly Ser Phe Asn
            100                 105                 110

Asp Tyr Glu Glu Leu Lys His Leu Leu Ser Arg Ile Asn His Phe Glu
        115                 120                 125
```

```
Lys Ile Gln Ile Ile Pro Lys Ser Ser Trp Ser Asp His Glu Ala Ser
    130                 135                 140
Ser Gly Val Ser Ser Ala Cys Pro Tyr Leu Gly Ser Pro Ser Phe Phe
145                 150                 155                 160
Arg Asn Val Val Trp Leu Ile Lys Lys Asn Ser Thr Tyr Pro Thr Ile
                165                 170                 175
Lys Lys Ser Tyr Asn Asn Thr Asn Gln Glu Asp Leu Leu Val Leu Trp
            180                 185                 190
Gly Ile His His Pro Asn Asp Ala Ala Glu Gln Thr Arg Leu Tyr Gln
        195                 200                 205
Asn Pro Thr Thr Tyr Ile Ser Ile Gly Thr Ser Thr Leu Asn Gln Arg
    210                 215                 220
Leu Val Pro Lys Ile Ala Thr Arg Ser Lys Val Asn Gly Gln Ser Gly
225                 230                 235                 240
Arg Met Glu Phe Phe Trp Thr Ile Leu Lys Pro Asn Asp Ala Ile Asn
                245                 250                 255
Phe Glu Ser Asn Gly Asn Phe Ile Ala Pro Glu Tyr Ala Tyr Lys Ile
            260                 265                 270
Val Lys Lys Gly Asp Ser Ala Ile Met Lys Ser Glu Leu Glu Tyr Gly
        275                 280                 285
Asn Cys Asn Thr Lys Cys Gln Thr Pro Met Gly Ala Ile Asn Ser Ser
    290                 295                 300
Met Pro Phe His Asn Ile His Pro Leu Thr Ile Gly Glu Cys Pro Lys
305                 310                 315                 320
Tyr Val Lys Ser Asn Arg Leu Val Leu Ala Thr Gly Leu Arg Asn Ser
                325                 330                 335
Pro Gln Arg Glu Ser Arg Arg Lys Lys Arg Gly Leu Phe Gly Ala Ile
            340                 345                 350
Ala Gly Phe Ile Glu Gly Gly Trp Gln Gly Met Val Asp Gly Trp Tyr
        355                 360                 365
Gly Tyr His His Ser Asn Glu Gln Gly Ser Gly Tyr Ala Ala Asp Lys
    370                 375                 380
Glu Ser Thr Gln Lys Ala Ile Asp Gly Val Thr Asn Lys Val Asn Ser
385                 390                 395                 400
Ile Ile Asp Lys Met Asn Thr Gln Phe Glu Ala Val Gly Arg Glu Phe
                405                 410                 415
Asn Asn Leu Glu Arg Arg Ile Glu Asn Leu Asn Lys Lys Met Glu Asp
            420                 425                 430
Gly Phe Leu Asp Val Trp Thr Tyr Asn Ala Glu Leu Leu Val Leu Met
        435                 440                 445
Glu Asn Glu Arg Thr Leu Asp Phe His Asp Ser Asn Val Lys Asn Leu
    450                 455                 460
Tyr Asp Lys Val Arg Leu Gln Leu Arg Asp Asn Ala Lys Glu Leu Gly
465                 470                 475                 480
Asn Gly Cys Phe Glu Phe Tyr His Lys Cys Asp Asn Glu Cys Met Glu
                485                 490                 495
Ser Ile Arg Asn Gly Thr Tyr Asn Tyr Pro Gln Tyr Ser Glu Glu Ala
            500                 505                 510
Arg Leu Lys Arg Glu Glu Ile Ser Gly Val Lys Leu Glu Ser Ile Gly
        515                 520                 525
Thr Tyr Gln Ile Leu Ser Ile Tyr Ser Thr Val Ala Ser Ser Leu Ala
    530                 535                 540
```

```
Leu Ala Ile Met Met Ala Gly Leu Ser Leu Trp Met Cys Ser Asn Gly
545                 550                 555                 560

Ser Leu Gln Cys Arg Ile Cys Ile
            565

<210> SEQ ID NO 3
<211> LENGTH: 24
<212> TYPE: DNA
<213> ORGANISM: Artificial Sequence
<220> FEATURE:
<223> OTHER INFORMATION: Synthesized oligonucleotide pBinPlus.2613c

<400> SEQUENCE: 3
aggaagggaa gaaagcgaaa ggag                                          24

<210> SEQ ID NO 4
<211> LENGTH: 56
<212> TYPE: DNA
<213> ORGANISM: Artificial Sequence
<220> FEATURE:
<223> OTHER INFORMATION: Synthesized oligonucleotide Mut-ATG115.r

<400> SEQUENCE: 4
gtgccgaagc acgatctgac aacgttgaag atcgctcacg caagaaagac aagaga       56

<210> SEQ ID NO 5
<211> LENGTH: 52
<212> TYPE: DNA
<213> ORGANISM: Artificial Sequence
<220> FEATURE:
<223> OTHER INFORMATION: Synthesized oligonucleotide Mut-ATG161.c

<400> SEQUENCE: 5
gttgtcagat cgtgcttcgg caccagtaca acgttttctt tcactgaagc ga           52

<210> SEQ ID NO 6
<211> LENGTH: 25
<212> TYPE: DNA
<213> ORGANISM: Artificial Sequence
<220> FEATURE:
<223> OTHER INFORMATION: Synthesized oligonucleotide LC-C5-1.110r

<400> SEQUENCE: 6
tctcctggag tcacagacag ggtgg                                         25

<210> SEQ ID NO 7
<211> LENGTH: 39
<212> TYPE: DNA
<213> ORGANISM: Artificial Sequence
<220> FEATURE:
<223> OTHER INFORMATION: Synthesized oligonucleotide ApaI-H5 (A-Indo).1c

<400> SEQUENCE: 7
tgtcgggccc atggagaaaa tagtgcttct tcttgcaat                          39

<210> SEQ ID NO 8
<211> LENGTH: 37
<212> TYPE: DNA
<213> ORGANISM: Artificial Sequence
<220> FEATURE:
<223> OTHER INFORMATION: Synthesized oligonucleotide H5
      (A-Indo)-StuI.1707r

<400> SEQUENCE: 8
aaataggcct ttaaatgcaa attctgcatt gtaacga                            37
```

<210> SEQ ID NO 9
<211> LENGTH: 3111
<212> TYPE: DNA
<213> ORGANISM: Artificial Sequence
<220> FEATURE:
<223> OTHER INFORMATION: Synthesized oligonucleotide contruct 660

<400> SEQUENCE: 9

| | | | | | |
|---|---|---|---|---|---|
| agaggtaccc | cgggctggta | tatttatatg | ttgtcaaata | actcaaaaac | cataaaagtt | 60 |
| taagttagca | agtgtgtaca | tttttacttg | aacaaaaata | ttcacctact | actgttataa | 120 |
| atcattatta | aacattagag | taaagaaata | tggatgataa | gaacaagagt | agtgatattt | 180 |
| tgacaacaat | tttgttgcaa | catttgagaa | aattttgttg | ttctctcttt | tcattggtca | 240 |
| aaaacaatag | agagagaaaa | aggaagaggg | agaataaaaa | cataatgtga | gtatgagaga | 300 |
| gaaagttgta | caaaagttgt | accaaaatag | ttgtacaaat | atcattgagg | aatttgacaa | 360 |
| aagctacaca | ataagggtt | aattgctgta | aataaataag | gatgacgcat | tagagagatg | 420 |
| taccattaga | gaattttttgg | caagtcatta | aaaagaaaga | ataaattatt | tttaaaatta | 480 |
| aaagttgagt | catttgatta | aacatgtgat | tatttaatga | attgatgaaa | gagttggatt | 540 |
| aaagttgtat | tagtaattag | aatttggtgt | caaatttaat | ttgacatttg | atctttttcct | 600 |
| atatattgcc | ccatagagtc | agttaactca | tttttatatt | tcatagatca | aataagagaa | 660 |
| ataacggtat | attaatccct | ccaaaaaaaa | aaacggtat | atttactaaa | aaatctaagc | 720 |
| cacgtaggag | gataacagga | tccccgtagg | aggataacat | ccaatccaac | caatcacaac | 780 |
| aatcctgatg | agataaccca | ctttaagccc | acgcatctgt | ggcacatcta | cattatctaa | 840 |
| atcacacatt | cttccacaca | tctgagccac | acaaaaacca | atccacatct | ttatcaccca | 900 |
| ttctataaaa | aatcacactt | tgtgagtcta | cactttgatt | cccttcaaac | acatacaaag | 960 |
| agaagagact | aattaattaa | ttaatcatct | tgagagaaaa | tggagaaaat | agtgcttctt | 1020 |
| cttgcaatag | tcagtcttgt | taaaagtgat | cagatttgca | ttggttacca | tgcaaacaat | 1080 |
| tcaacagagc | aggttgacac | aatcatggaa | aagaacgtta | ctgttacaca | tgcccaagac | 1140 |
| atactggaaa | agacacacaa | cgggaagctc | tgcgatctag | atggagtgaa | gcctctaatt | 1200 |
| ttaagagatt | gtagtgtagc | tggatggctc | ctcgggaacc | caatgtgtga | cgaattcatc | 1260 |
| aatgtaccgg | aatggtctta | catagtggag | aaggccaatc | caaccaatga | cctctgttac | 1320 |
| ccagggagtt | tcaacgacta | tgaagaactg | aaacacctat | tgagcagaat | aaaccatttt | 1380 |
| gagaaaattc | aaatcatccc | caaaagttct | tggtccgatc | atgaagcctc | atcaggagtt | 1440 |
| agctcagcat | gtccatacct | gggaagtccc | tccttttttta | gaaatgtggt | atggcttatc | 1500 |
| aaaaagaaca | gtacataccc | aacaataaag | aaaagctaca | ataataccaa | ccaagaggat | 1560 |
| cttttggtac | tgtggggaat | tcaccatcct | aatgatgcgg | cagagcagac | aaggctatat | 1620 |
| caaaacccaa | ccacctatat | ttccattggg | acatcaacac | taaaccagag | attggtacca | 1680 |
| aaaatagcta | ctagatccaa | agtaaacggg | caaagtggaa | ggatggagtt | cttctggaca | 1740 |
| attttaaaac | ctaatgatgc | aatcaacttc | gagagtaatg | gaaatttcat | tgctccagaa | 1800 |
| tatgcataca | aaattgtcaa | gaaggggac | tcagcaatta | tgaaaagtga | attggaatat | 1860 |
| ggtaactgca | acaccaagtg | tcaaactcca | atggggggcga | taaactctag | tatgccattc | 1920 |
| cacaacatac | accctctcac | catcgggaa | tgcccaaat | atgtgaaatc | aaacagatta | 1980 |
| gtccttgcaa | cagggctcag | aaatagccct | caaagagaga | gcagaagaaa | aaagagagga | 2040 |
| ctatttggag | ctatagcagg | ttttatagag | ggaggatggc | agggaatggt | agatggttgg | 2100 |

```
tatgggtacc accatagcaa tgagcagggg agtgggtacg ctgcagacaa agaatccact    2160
caaaaggcaa tagatggagt caccaataag gtcaactcaa tcattgacaa aatgaacact    2220
cagtttgagg ccgttggaag ggaatttaat aacttagaaa ggagaataga gaatttaaac    2280
aagaagatgg aagacgggtt tctagatgtc tggacttata atgccgaact tctggttctc    2340
atggaaaatg agagaactct agactttcat gactcaaatg ttaagaacct ctacgacaag    2400
gtccgactac agcttaggga taatgcaaag gagctgggta acggttgttt cgagttctat    2460
cacaaatgtg ataatgaatg tatggaaagt ataagaaacg gaacgtacaa ctatccgcag    2520
tattcagaag aagcaagatt aaaaagagag gaaataagtg gggtaaaatt ggaatcaata    2580
ggaacttacc aaatactgtc aatttattca acagtggcga gttccctagc actggcaatc    2640
atgatggctg gtctatcttt atggatgtgc tccaatggat cgttacaatg cagaatttgc    2700
atttaagagc tctaagttaa aatgcttctt cgtctcctat ttataatatg gtttgttatt    2760
gttaattttg ttcttgtaga agagcttaat taatcgttgt tgttatgaaa tactatttgt    2820
atgagatgaa ctggtgtaat gtaattcatt tacataagtg gagtcagaat cagaatgttt    2880
cctccataac taactagaca tgaagacctg ccgcgtacaa ttgtcttata tttgaacaac    2940
taaaattgaa catcttttgc cacaacttta taagtggtta atatagctca aatatatggt    3000
caagttcaat agattaataa tggaaatatc agttatcgaa attcattaac aatcaactta    3060
acgttattaa ctactaattt tatatcatcc cctttgataa atgatagtac a             3111
```

```
<210> SEQ ID NO 10
<211> LENGTH: 26
<212> TYPE: PRT
<213> ORGANISM: Medicago sativa

<400> SEQUENCE: 10

Met Ala Lys Asn Val Ala Ile Phe Gly Leu Leu Phe Ser Leu Leu Leu
1               5                   10                  15

Leu Val Pro Ser Gln Ile Phe Ala Glu Glu
            20                  25

<210> SEQ ID NO 11
<211> LENGTH: 25
<212> TYPE: DNA
<213> ORGANISM: Artificial sequence
<220> FEATURE:
<223> OTHER INFORMATION: Synthesized oligonucleotide Plasto-443c

<400> SEQUENCE: 11
gtattagtaa ttagaatttg gtgtc                                            25

<210> SEQ ID NO 12
<211> LENGTH: 34
<212> TYPE: DNA
<213> ORGANISM: Artificial sequence
<220> FEATURE:
<223> OTHER INFORMATION: Synthesized oligonucleotide supP19-plasto.r

<400> SEQUENCE: 12
ccttgtatag ctcgttccat tttctctcaa gatg                                  34

<210> SEQ ID NO 13
<211> LENGTH: 20
<212> TYPE: DNA
<213> ORGANISM: Artificial sequence
<220> FEATURE:
```

```
<223> OTHER INFORMATION: Synthesized oligonucleotide supP19-1c

<400> SEQUENCE: 13
atggaacgag ctatacaagg                                                   20

<210> SEQ ID NO 14
<211> LENGTH: 32
<212> TYPE: DNA
<213> ORGANISM: Artificial sequence
<220> FEATURE:
<223> OTHER INFORMATION: Synthesized oligonucleotide SupP19-SacI.r

<400> SEQUENCE: 14
agtcgagctc ttactcgctt tcttttcga ag                                      32
```